United States Patent
Bomati et al.

(10) Patent No.: US 9,677,057 B2
(45) Date of Patent: Jun. 13, 2017

(54) MODIFIED POLYMERASES FOR IMPROVED INCORPORATION OF NUCLEOTIDE ANALOGUES

(71) Applicant: Illumina, Inc., San Diego, CA (US)

(72) Inventors: Erin Bomati, Santee, CA (US); Michael Previte, Carlsbad, CA (US); Matthew William Kellinger, San Diego, CA (US); Cheng-Yao Chen, San Diego, CA (US); Molly He, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 14/869,792

(22) Filed: Sep. 29, 2015

(65) Prior Publication Data

US 2016/0090579 A1 Mar. 31, 2016

Related U.S. Application Data

(60) Provisional application No. 62/057,843, filed on Sep. 30, 2014.

(51) Int. Cl.
*C12N 9/12* (2006.01)
*C07H 21/04* (2006.01)
*C07K 1/00* (2006.01)
*C12Q 1/68* (2006.01)

(52) U.S. Cl.
CPC ......... *C12N 9/1252* (2013.01); *C12Q 1/6844* (2013.01); *C12Y 207/07007* (2013.01)

(58) Field of Classification Search
CPC ............ C12N 9/1252; C12Q 2521/101; C12Q 1/6844; C12Y 207/07007
USPC ............................ 435/194; 536/23.2; 530/350
See application file for complete search history.

(56) References Cited

U.S. PATENT DOCUMENTS

| | | | | |
|---|---|---|---|---|
| 5,882,904 A | * | 3/1999 | Riedl | C12N 9/1252 435/194 |
| 7,892,797 B2 | * | 2/2011 | Mitsis | C12P 19/34 435/6.14 |
| 8,283,149 B2 | | 10/2012 | Niu et al. | |
| 8,460,910 B2 | | 6/2013 | Smith et al. | |
| 8,623,628 B2 | | 1/2014 | Ost et al. | |
| 8,852,910 B2 | | 10/2014 | Smith et al. | |
| 9,273,352 B2 | | 3/2016 | Smith et al. | |
| 2006/0240439 A1 | | 10/2006 | Smith et al. | |
| 2006/0281109 A1 | | 12/2006 | Barr Ost et al. | |
| 2012/0020537 A1 | | 1/2012 | Garcia et al. | |
| 2015/0024463 A1 | | 1/2015 | Smith et al. | |
| 2016/0032377 A1 | | 2/2016 | Chen et al. | |
| 2016/0090579 A1 | | 3/2016 | Bomati et al. | |
| 2016/0115461 A1 | | 4/2016 | Smith et al. | |

FOREIGN PATENT DOCUMENTS

| | | |
|---|---|---|
| EP | 0 822 256 A2 | 2/1998 |
| WO | WO 2005/024010 A1 | 3/2005 |
| WO | WO 2007/076057 A2 | 7/2007 |
| WO | WO 2008/051530 A2 | 5/2008 |
| WO | WO 2014/142921 A1 | 9/2014 |
| WO | WO 2015/200693 A1 | 12/2015 |

OTHER PUBLICATIONS

Banerjee et al., Improving enzymes for bioanss conversion: A basic research perspective. Bioenerg. Res., 2010, vol. 3: 82-92.*
Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi.*
Devos et al., Practical limits of function prediction. Proteins: Structure, Function, and Genetics. 2000, vol. 41: 98-107.*
Guo et al., Protein tolerance to random amino acid change. PNAS., 2004, vol. 101 (25): 9205-9210.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
PCT Patent Application No. PCT/US2015/053021 filed Sep. 29, 2015; International Search Report / Written Opinion issued Dec. 8, 2015; 25 pages.
Hopfner et al., "Crystal structure of a thermostable type B DNA polymerase from *Thermococcus gorgonarius*", Mar. 30, 1999, PNAS 96(7):3600-3605.
Rodriquez et al., "Crystal Structure of a Pol Alpha Family DNA Polymerase from the Hyperthermophilic Archeaon *Thermococcus sp.* 9° N-7", Jun. 2, 2000, *Journal of Molecular Biology* 299(2):447-462.

* cited by examiner

*Primary Examiner* — Ganapathirama Raghu
(74) *Attorney, Agent, or Firm* — Mueting, Raasch & Gebhardt, P.A.

(57) ABSTRACT

Presented herein are polymerase enzymes for improved incorporation of nucleotide analogs, in particular nucleotides which are modified at the 3' sugar hydroxyl, as well as methods and kits using the same.

16 Claims, 5 Drawing Sheets

```
         400       410       420
Pol957   WDNIVYLDFRSAAISIIITHNVSPDTLNREGCK
9oN      WDNIVYLDFRSLYPSIIITHNVSPDTLNREGCK
TGO      WENIVYLDFRSLYPSIIITHNVSPDTLNREGCK
KOD1     WENIVYLDFRSLYPSIIITHNVSPDTLNREGCE
Pfu      WENIVYLDFRALYPSIIITHNVSPDTLNREGCK
Mm_S2    HEDIVSMDFLSLYPSIIMSHNLSPDTLNLEGCK
RB69     YKYVMSFDLTSLYPSIIRQVNISPETIAGTFKV
```

```
         480       490       500       510       520       530
Pol957   ..PLEKKLLDYRQRVIKILANSFYGYYGYAKARWYCKECAESVSAWGREYLEMVIRELEEKFG.
9oN      ..PLEKKLLDYRQRAIKILANSFYGYYGYAKARWYCKECAESVTAWGREYIEMVIRELEEKFG.
TGO      ..PIEKKLLDYRQRAIKILANSFYGYYGYAKARWYCKECAESVTAWGRQYIETTIRELEEKFG.
KOD1     ..PIERKLLDYRQRAIKILANSLYGYYGYAKARWYCKECAESVTAWGREYITMTIKELEEKYG.
Pfu      ..PIEKKLLDYRQRKAIKILANSFYGYYGYAKARWYCKECAESVTAWGRKYIELVWKELEEKFG.
Mm_S2    ..DEEYQILDYEQCRSIKVLANSHYGYLAFPMARWYSRDCAEITTHLGRQYIQKTIEE.AENFG.
RB69     EMLFRAQRTEVAGMTAQINRKLLINSLYGALGNVWFRYDLRNATAITTFGQMALQWIERKVNEYLNEVC
```

FIG. 2

```
                        SEQUENCE LISTING

<160> NUMBER OF SEQ ID NOS: 43

<210> SEQ ID NO 1
<211> LENGTH: 10
<212> TYPE: PRT
<213> ORGANISM: Artificial Sequence
<220> FEATURE:
<223> OTHER INFORMATION: Various including Thermococcus sp. or
      Pyrococcus sp.
<220> FEATURE:
<221> NAME/KEY: Variant
<222> LOCATION: (2)..(2)
<223> OTHER INFORMATION: X= any AA
<220> FEATURE:
<221> NAME/KEY: Variant
<222> LOCATION: (4)..(4)
<223> OTHER INFORMATION: X= any AA
<220> FEATURE:
<221> NAME/KEY: Variant
<222> LOCATION: (5)..(5)
<223> OTHER INFORMATION: X= any AA

<400> SEQUENCE: 1

Phe Xaa Ile Xaa Xaa Leu Tyr His Glu Gly
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Various including Thermococcus sp. or
      Pyrococcus sp.
<220> FEATURE:
<221> NAME/KEY: Variant
<222> LOCATION: (7)..(7)
<223> OTHER INFORMATION: X = any AA
<220> FEATURE:
<221> NAME/KEY: Variant
<222> LOCATION: (8)..(8)
<223> OTHER INFORMATION: X = any AA

<400> SEQUENCE: 2

His Glu Gly Glu Glu Phe Xaa Xaa Gly Pro Ile
1               5                   10

<210> SEQ ID NO 3
<211> LENGTH: 18
<212> TYPE: PRT
<213> ORGANISM: Artificial Sequence
<220> FEATURE:
<223> OTHER INFORMATION: Various including Thermococcus sp. or
      Pyrococcus sp.
<220> FEATURE:
<221> NAME/KEY: VARIANT
<222> LOCATION: (2)..(2)
<223> OTHER INFORMATION: X= any AA
<220> FEATURE:
<221> NAME/KEY: VARIANT
<222> LOCATION: (3)..(3)
<223> OTHER INFORMATION: X= any AA
<220> FEATURE:
<221> NAME/KEY: VARIANT
<222> LOCATION: (4)..(4)
<223> OTHER INFORMATION: X= any AA
<220> FEATURE:
<221> NAME/KEY: VARIANT
<222> LOCATION: (8)..(8)
<223> OTHER INFORMATION: X= any AA
<220> FEATURE:
<221> NAME/KEY: VARIANT
```

-continued

```
<222> LOCATION: (10)..(10)
<223> OTHER INFORMATION: X= any AA
<220> FEATURE:
<221> NAME/KEY: VARIANT
<222> LOCATION: (11)..(11)
<223> OTHER INFORMATION: X= any AA
<220> FEATURE:
<221> NAME/KEY: VARIANT
<222> LOCATION: (12)..(12)
<223> OTHER INFORMATION: X= any AA
<220> FEATURE:
<221> NAME/KEY: VARIANT
<222> LOCATION: (14)..(14)
<223> OTHER INFORMATION: X= any AA

<400> SEQUENCE: 3

Glu Xaa Xaa Xaa Leu Asp Tyr Xaa Gln Xaa Xaa Xaa Lys Xaa Leu Ala
1               5                   10                  15

Asn Ser

<210> SEQ ID NO 4
<211> LENGTH: 18
<212> TYPE: PRT
<213> ORGANISM: Artificial Sequence
<220> FEATURE:
<223> OTHER INFORMATION: Various including Thermococcus sp. or
      Pyrococcus sp.
<220> FEATURE:
<221> NAME/KEY: VARIANT
<222> LOCATION: (2)..(2)
<223> OTHER INFORMATION: X=K, R, Y
<220> FEATURE:
<221> NAME/KEY: VARIANT
<222> LOCATION: (3)..(3)
<223> OTHER INFORMATION: X=K, I, Q
<220> FEATURE:
<221> NAME/KEY: VARIANT
<222> LOCATION: (4)..(4)
<223> OTHER INFORMATION: X=L, I, M
<220> FEATURE:
<221> NAME/KEY: VARIANT
<222> LOCATION: (8)..(8)
<223> OTHER INFORMATION: X=R, E
<220> FEATURE:
<221> NAME/KEY: VARIANT
<222> LOCATION: (10)..(10)
<223> OTHER INFORMATION: X=R, K, I
<220> FEATURE:
<221> NAME/KEY: VARIANT
<222> LOCATION: (11)..(11)
<223> OTHER INFORMATION: X=A, K, L, V, S
<220> FEATURE:
<221> NAME/KEY: VARIANT
<222> LOCATION: (12)..(12)
<223> OTHER INFORMATION: X=I, V, L, N
<220> FEATURE:
<221> NAME/KEY: VARIANT
<222> LOCATION: (14)..(14)
<223> OTHER INFORMATION: X=I, V, L

<400> SEQUENCE: 4

Glu Xaa Xaa Xaa Leu Asp Tyr Xaa Gln Xaa Xaa Xaa Lys Xaa Leu Ala
1               5                   10                  15

Asn Ser

<210> SEQ ID NO 5
<211> LENGTH: 18
<212> TYPE: PRT
<213> ORGANISM: Artificial Sequence
<220> FEATURE:
<223> OTHER INFORMATION: Various including Thermococcus sp. or
      Pyrococcus sp.
<220> FEATURE:
```

```
<221> NAME/KEY: VARIANT
<222> LOCATION: (2)..(2)
<223> OTHER INFORMATION: X=R, K
<220> FEATURE:
<221> NAME/KEY: VARIANT
<222> LOCATION: (3)..(3)
<223> OTHER INFORMATION: X=K, I
<220> FEATURE:
<221> NAME/KEY: VARIANT
<222> LOCATION: (10)..(10)
<223> OTHER INFORMATION: X=R, K
<220> FEATURE:
<221> NAME/KEY: VARIANT
<222> LOCATION: (14)..(14)
<223> OTHER INFORMATION: X=I, L

<400> SEQUENCE: 5

Glu Xaa Xaa Leu Leu Asp Tyr Arg Gln Xaa Ala Ile Lys Xaa Leu Ala
1               5                   10                  15

Asn Ser

<210> SEQ ID NO 6
<211> LENGTH: 18
<212> TYPE: PRT
<213> ORGANISM: Artificial Sequence
<220> FEATURE:
<223> OTHER INFORMATION: Various including Thermococcus sp. or
      Pyrococcus sp.

<400> SEQUENCE: 6

Glu Lys Lys Leu Leu Asp Tyr Arg Gln Arg Ala Ile Lys Ile Leu Ala
1               5                   10                  15

Asn Ser

<210> SEQ ID NO 7
<211> LENGTH: 14
<212> TYPE: PRT
<213> ORGANISM: Artificial Sequence
<220> FEATURE:
<223> OTHER INFORMATION: Various including Thermococcus sp. or
      Pyrococcus sp.

<400> SEQUENCE: 7

Arg Gly Phe Phe Val Thr Lys Lys Lys Tyr Ala Val Ile Asp
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Various including Thermococcus sp. or
      Pyrococcus sp.
<220> FEATURE:
<221> NAME/KEY: Variant
<222> LOCATION: (5)..(5)
<223> OTHER INFORMATION: X = any AA

<400> SEQUENCE: 8

Gly Asp Val Glu Xaa Ala Val Arg Ile Val Lys Glu Val
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Various including Thermococcus sp. or
      Pyrococcus sp.
```

```
<220> FEATURE:
<221> NAME/KEY: Variant
<222> LOCATION: (1)..(1)
<223> OTHER INFORMATION: X = any AA
<220> FEATURE:
<221> NAME/KEY: Variant
<222> LOCATION: (5)..(5)
<223> OTHER INFORMATION: X = any AA
<220> FEATURE:
<221> NAME/KEY: Variant
<222> LOCATION: (6)..(6)
<223> OTHER INFORMATION: X = any AA
<220> FEATURE:
<221> NAME/KEY: Variant
<222> LOCATION: (7)..(7)
<223> OTHER INFORMATION: X = any AA
<220> FEATURE:
<221> NAME/KEY: Variant
<222> LOCATION: (9)..(9)
<223> OTHER INFORMATION: X = any AA

<400> SEQUENCE: 9

Xaa Arg Ala Ile Xaa Xaa Xaa Glu Xaa Asp Pro
1               5                   10

<210> SEQ ID NO 10
<211> LENGTH: 775
<212> TYPE: PRT
<213> ORGANISM: Thermococcus sp. 9N-7

<400> SEQUENCE: 10

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
        50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Asp Ile Glu Thr
        130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240
```

```
Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
        260                 265                 270

Tyr Thr Leu Glu Ala Val Tyr Glu Ala Val Phe Gly Lys Pro Lys Glu
    275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
```

```
                      660                 665                 670
Tyr Lys Ala Thr Gly Pro His Val Ala Val Ala Lys Arg Leu Ala Ala
                675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
                755                 760                 765

Leu Lys Val Lys Gly Lys Lys
            770                 775

<210> SEQ ID NO 11
<211> LENGTH: 775
<212> TYPE: PRT
<213> ORGANISM: Thermococcus sp. 9N-7
<220> FEATURE:
<221> NAME/KEY: Variant
<222> LOCATION: (144)..(144)
<223> OTHER INFORMATION: X=T, A, G, L
<220> FEATURE:
<221> NAME/KEY: Variant
<222> LOCATION: (153)..(153)
<223> OTHER INFORMATION: X= G, D
<220> FEATURE:
<221> NAME/KEY: Variant
<222> LOCATION: (476)..(476)
<223> OTHER INFORMATION: X= K, W
<220> FEATURE:
<221> NAME/KEY: Variant
<222> LOCATION: (478)..(478)
<223> OTHER INFORMATION: X= L, S, R, T
<220> FEATURE:
<221> NAME/KEY: Variant
<222> LOCATION: (590)..(590)
<223> OTHER INFORMATION: X= T, I, G
<220> FEATURE:
<221> NAME/KEY: Variant
<222> LOCATION: (639)..(639)
<223> OTHER INFORMATION: X= A, V, F
<220> FEATURE:
<221> NAME/KEY: Variant
<222> LOCATION: (718)..(718)
<223> OTHER INFORMATION: X= D, N

<400> SEQUENCE: 11

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
        50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110
```

```
Asp Ile Pro Phe Ala Lys Arg Tyr Leu Ile Asp Lys Gly Leu Ile Pro
            115                 120                 125
Met Glu Gly Asp Glu Glu Leu Thr Met Leu Ala Phe Asp Ile Glu Xaa
        130                 135                 140
Leu Tyr His Glu Gly Glu Glu Phe Xaa Thr Gly Pro Ile Leu Met Ile
145                 150                 155                 160
Ser Tyr Ala Asp Gly Ser Glu Ala Arg Val Ile Thr Trp Lys Lys Ile
                165                 170                 175
Asp Leu Pro Tyr Val Asp Val Val Ser Thr Glu Lys Glu Met Ile Lys
            180                 185                 190
Arg Phe Leu Arg Val Val Arg Glu Lys Asp Pro Asp Val Leu Ile Thr
        195                 200                 205
Tyr Asn Gly Asp Asn Phe Asp Phe Ala Tyr Leu Lys Lys Arg Cys Glu
    210                 215                 220
Glu Leu Gly Ile Lys Phe Thr Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
            260                 265                 270
Tyr Thr Leu Glu Ala Val Tyr Glu Ala Val Phe Gly Lys Pro Lys Glu
        275                 280                 285
Lys Val Tyr Ala Glu Glu Ile Ala Gln Ala Trp Glu Ser Gly Glu Gly
    290                 295                 300
Leu Glu Arg Val Ala Arg Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                325                 330                 335
Ile Gly Gln Ser Leu Trp Asp Val Ser Arg Ser Ser Thr Gly Asn Leu
            340                 345                 350
Val Glu Trp Phe Leu Leu Arg Lys Ala Tyr Lys Arg Asn Glu Leu Ala
        355                 360                 365
Pro Asn Lys Pro Asp Glu Arg Glu Leu Ala Arg Arg Gly Gly Tyr
    370                 375                 380
Ala Gly Gly Tyr Val Lys Glu Pro Glu Arg Gly Leu Trp Asp Asn Ile
385                 390                 395                 400
Val Tyr Leu Asp Phe Arg Ser Leu Tyr Pro Ser Ile Ile Thr His
                405                 410                 415
Asn Val Ser Pro Asp Thr Leu Asn Arg Glu Gly Cys Lys Glu Tyr Asp
            420                 425                 430
Val Ala Pro Glu Val Gly His Lys Phe Cys Lys Asp Phe Pro Gly Phe
        435                 440                 445
Ile Pro Ser Leu Leu Gly Asp Leu Leu Glu Glu Arg Gln Lys Ile Lys
    450                 455                 460
Arg Lys Met Lys Ala Thr Val Asp Pro Leu Glu Xaa Lys Xaa Leu Asp
465                 470                 475                 480
Tyr Arg Gln Arg Ala Ile Lys Ile Leu Ala Asn Ser Phe Tyr Gly Tyr
                485                 490                 495
Tyr Gly Tyr Ala Lys Ala Arg Trp Tyr Cys Lys Glu Cys Ala Glu Ser
            500                 505                 510
Val Thr Ala Trp Gly Arg Glu Tyr Ile Glu Met Val Ile Arg Glu Leu
        515                 520                 525
```

```
Glu Glu Lys Phe Gly Phe Lys Val Leu Tyr Ala Asp Thr Asp Gly Leu
        530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Xaa Lys Lys
                580                 585                 590

Lys Tyr Ala Val Ile Asp Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Xaa Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
                660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Xaa Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
        740                 745                 750

Glu Asp Leu Arg Tyr Gln Lys Thr Lys Gln Val Gly Leu Gly Ala Trp
        755                 760                 765

Leu Lys Val Lys Gly Lys Lys
        770                 775

<210> SEQ ID NO 12
<211> LENGTH: 775
<212> TYPE: PRT
<213> ORGANISM: Thermococcus sp. 9N-7
<220> FEATURE:
<221> NAME/KEY: Variant
<222> LOCATION: (144)..(144)
<223> OTHER INFORMATION: X= T, A
<220> FEATURE:
<221> NAME/KEY: Variant
<222> LOCATION: (153)..(153)
<223> OTHER INFORMATION: X= G, D
<220> FEATURE:
<221> NAME/KEY: Variant
<222> LOCATION: (408)..(408)
<223> OTHER INFORMATION: X= L, A
<220> FEATURE:
<221> NAME/KEY: Variant
<222> LOCATION: (409)..(409)
<223> OTHER INFORMATION: X= Y, A
<220> FEATURE:
<221> NAME/KEY: Variant
<222> LOCATION: (410)..(410)
<223> OTHER INFORMATION: X= P, V, A, I
<220> FEATURE:
<221> NAME/KEY: Variant
<222> LOCATION: (476)..(476)
<223> OTHER INFORMATION: X= K, W
<220> FEATURE:
<221> NAME/KEY: Variant
```

```
<222> LOCATION: (478)..(478)
<223> OTHER INFORMATION: X= L, S
<220> FEATURE:
<221> NAME/KEY: Variant
<222> LOCATION: (485)..(485)
<223> OTHER INFORMATION: X= A, L, V
<220> FEATURE:
<221> NAME/KEY: Variant
<222> LOCATION: (590)..(590)
<223> OTHER INFORMATION: X= T, I
<220> FEATURE:
<221> NAME/KEY: Variant
<222> LOCATION: (639)..(639)
<223> OTHER INFORMATION: X= A, V, F
<220> FEATURE:
<221> NAME/KEY: Variant
<222> LOCATION: (718)..(718)
<223> OTHER INFORMATION: X= D, N

<400> SEQUENCE: 12
```

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Asp Ile Glu Xaa
    130                 135                 140

Leu Tyr His Glu Gly Glu Glu Phe Xaa Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr

```
                    305                 310                 315                 320
                Glu Leu Gly Arg Glu Phe Phe Pro Met Glu Ala Gln Leu Ser Arg Leu
                                325                 330                 335

Ile Gly Gln Ser Leu Trp Asp Val Ser Arg Ser Thr Gly Asn Leu
                                340                 345                 350

Val Glu Trp Phe Leu Arg Lys Ala Tyr Lys Arg Asn Glu Leu Ala
                                355                 360                 365

Pro Asn Lys Pro Asp Glu Arg Glu Leu Ala Arg Arg Gly Gly Tyr
                                370                 375                 380

Ala Gly Gly Tyr Val Lys Glu Pro Glu Arg Gly Leu Trp Asp Asn Ile
                385                             390                 395                 400

Val Tyr Leu Asp Phe Arg Ser Xaa Xaa Xaa Ser Ile Ile Ile Thr His
                                405                 410                 415

Asn Val Ser Pro Asp Thr Leu Asn Arg Glu Gly Cys Lys Glu Tyr Asp
                                420                 425                 430

Val Ala Pro Glu Val Gly His Lys Phe Cys Lys Asp Phe Pro Gly Phe
                                435                 440                 445

Ile Pro Ser Leu Leu Gly Asp Leu Leu Glu Glu Arg Gln Lys Ile Lys
                                450                 455                 460

Arg Lys Met Lys Ala Thr Val Asp Pro Leu Glu Xaa Lys Xaa Leu Asp
                465                             470                 475                 480

Tyr Arg Gln Arg Xaa Ile Lys Ile Leu Ala Asn Ser Phe Tyr Gly Tyr
                                485                 490                 495

Tyr Gly Tyr Ala Lys Ala Arg Trp Tyr Cys Lys Glu Cys Ala Glu Ser
                                500                 505                 510

Val Thr Ala Trp Gly Arg Glu Tyr Ile Glu Met Val Ile Arg Glu Leu
                                515                 520                 525

Glu Glu Lys Phe Gly Phe Lys Val Leu Tyr Ala Asp Thr Asp Gly Leu
                                530                 535                 540

His Ala Thr Ile Pro Gly Ala Asp Ala Glu Thr Val Lys Lys Lys Ala
                545                             550                 555                 560

Lys Glu Phe Leu Lys Tyr Ile Asn Pro Lys Leu Pro Gly Leu Leu Glu
                                565                 570                 575

Leu Glu Tyr Glu Gly Phe Tyr Val Arg Gly Phe Phe Val Xaa Lys Lys
                                580                 585                 590

Lys Tyr Ala Val Ile Asp Glu Glu Gly Lys Ile Thr Thr Arg Gly Leu
                                595                 600                 605

Glu Ile Val Arg Arg Asp Trp Ser Glu Ile Ala Lys Glu Thr Gln Ala
                                610                 615                 620

Arg Val Leu Glu Ala Ile Leu Lys His Gly Asp Val Glu Glu Xaa Val
                625                             630                 635                 640

Arg Ile Val Lys Glu Val Thr Glu Lys Leu Ser Lys Tyr Glu Val Pro
                                645                 650                 655

Pro Glu Lys Leu Val Ile His Glu Gln Ile Thr Arg Asp Leu Arg Asp
                                660                 665                 670

Tyr Lys Ala Thr Gly Pro His Val Ala Val Ala Lys Arg Leu Ala Ala
                                675                 680                 685

Arg Gly Val Lys Ile Arg Pro Gly Thr Val Ile Ser Tyr Ile Val Leu
                                690                 695                 700

Lys Gly Ser Gly Arg Ile Gly Asp Arg Ala Ile Pro Ala Xaa Glu Phe
                705                             710                 715                 720

Asp Pro Thr Lys His Arg Tyr Asp Ala Glu Tyr Tyr Ile Glu Asn Gln
                                725                 730                 735
```

```
Val Leu Pro Ala Val Glu Arg Ile Leu Lys Ala Phe Gly Tyr Arg Lys
                740                 745                 750

Glu Asp Leu Arg Tyr Gln Lys Thr Lys Gln Val Gly Leu Gly Ala Trp
            755                 760                 765

Leu Lys Val Lys Gly Lys Lys
        770             775

<210> SEQ ID NO 13
<211> LENGTH: 775
<212> TYPE: PRT
<213> ORGANISM: Thermococcus sp. 9N-7

<400> SEQUENCE: 13

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
        290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
```

```
                        325                 330                 335
Ile Gly Gln Ser Leu Trp Asp Val Ser Arg Ser Thr Gly Asn Leu
                340                 345                 350
Val Glu Trp Phe Leu Leu Arg Lys Ala Tyr Lys Arg Asn Glu Leu Ala
                355                 360                 365
Pro Asn Lys Pro Asp Glu Arg Glu Leu Ala Arg Arg Gly Gly Tyr
            370                 375                 380
Ala Gly Gly Tyr Val Lys Glu Pro Arg Gly Leu Trp Asp Asn Ile
385                 390                 395                 400
Val Tyr Leu Asp Phe Arg Ser Leu Tyr Pro Ser Ile Ile Thr His
                405                 410                 415
Asn Val Ser Pro Asp Thr Leu Asn Arg Glu Gly Cys Lys Glu Tyr Asp
                420                 425                 430
Val Ala Pro Glu Val Gly His Lys Phe Cys Lys Asp Phe Pro Gly Phe
                435                 440                 445
Ile Pro Ser Leu Leu Gly Asp Leu Leu Glu Glu Arg Gln Lys Ile Lys
            450                 455                 460
Arg Lys Met Lys Ala Thr Val Asp Pro Leu Glu Lys Lys Leu Leu Asp
465                 470                 475                 480
Tyr Arg Gln Arg Ala Ile Lys Ile Leu Ala Asn Ser Phe Tyr Gly Tyr
                485                 490                 495
Tyr Gly Tyr Ala Lys Ala Arg Trp Tyr Cys Lys Glu Cys Ala Glu Ser
                500                 505                 510
Val Thr Ala Trp Gly Arg Glu Tyr Ile Glu Met Val Ile Arg Glu Leu
            515                 520                 525
Glu Glu Lys Phe Gly Phe Lys Val Leu Tyr Ala Asp Thr Asp Gly Leu
            530                 535                 540
His Ala Thr Ile Pro Gly Ala Asp Ala Glu Thr Val Lys Lys Lys Ala
545                 550                 555                 560
Lys Glu Phe Leu Lys Tyr Ile Asn Pro Lys Leu Pro Gly Leu Leu Glu
                565                 570                 575
Leu Glu Tyr Glu Gly Phe Tyr Val Arg Gly Phe Phe Val Thr Lys Lys
                580                 585                 590
Lys Tyr Ala Val Ile Asp Glu Glu Gly Lys Ile Thr Thr Arg Gly Leu
                595                 600                 605
Glu Ile Val Arg Arg Asp Trp Ser Glu Ile Ala Lys Glu Thr Gln Ala
            610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Arg Asp
            660                 665                 670
Tyr Lys Ala Thr Gly Pro His Val Ala Val Ala Lys Arg Leu Ala Ala
                675                 680                 685
Arg Gly Val Lys Ile Arg Pro Gly Thr Val Ile Ser Tyr Ile Val Leu
            690                 695                 700
Lys Gly Ser Gly Arg Ile Gly Asp Arg Ala Ile Pro Ala Asp Glu Phe
705                 710                 715                 720
Asp Pro Thr Lys His Arg Tyr Asp Ala Glu Tyr Tyr Ile Glu Asn Gln
                725                 730                 735
Val Leu Pro Ala Val Glu Arg Ile Leu Lys Ala Phe Gly Tyr Arg Lys
            740                 745                 750
```

-continued

```
Glu Asp Leu Arg Tyr Gln Lys Thr Lys Gln Val Gly Leu Gly Ala Trp
        755                 760                 765

Leu Lys Val Lys Gly Lys Lys
    770             775

<210> SEQ ID NO 14
<211> LENGTH: 775
<212> TYPE: PRT
<213> ORGANISM: Thermococcus sp. 9N-7
<220> FEATURE:
<221> NAME/KEY: Variant
<222> LOCATION: (144)..(144)
<223> OTHER INFORMATION: X= T, A
<220> FEATURE:
<221> NAME/KEY: Variant
<222> LOCATION: (153)..(153)
<223> OTHER INFORMATION: X= G, D
<220> FEATURE:
<221> NAME/KEY: Variant
<222> LOCATION: (476)..(476)
<223> OTHER INFORMATION: X= K, W
<220> FEATURE:
<221> NAME/KEY: Variant
<222> LOCATION: (478)..(478)
<223> OTHER INFORMATION: X= L, S
<220> FEATURE:
<221> NAME/KEY: Variant
<222> LOCATION: (590)..(590)
<223> OTHER INFORMATION: X= T, I
<220> FEATURE:
<221> NAME/KEY: Variant
<222> LOCATION: (639)..(639)
<223> OTHER INFORMATION: X= A, V, F
<220> FEATURE:
<221> NAME/KEY: Variant
<222> LOCATION: (718)..(718)
<223> OTHER INFORMATION: X= D, N

<400> SEQUENCE: 14

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Xaa
    130                 135                 140

Leu Tyr His Glu Gly Glu Glu Phe Xaa Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Ser Thr Lys Glu Met Ile Lys
            180                 185                 190
```

```
Arg Phe Leu Arg Val Val Arg Glu Lys Asp Pro Asp Val Leu Ile Thr
            195                 200                 205
Tyr Asn Gly Asp Asn Phe Asp Phe Ala Tyr Leu Lys Lys Arg Cys Glu
        210                 215                 220
Glu Leu Gly Ile Lys Phe Thr Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
            260                 265                 270
Tyr Thr Leu Glu Ala Val Tyr Glu Ala Val Phe Gly Lys Pro Lys Glu
        275                 280                 285
Lys Val Tyr Ala Glu Glu Ile Ala Gln Ala Trp Glu Ser Gly Glu Gly
290                 295                 300
Leu Glu Arg Val Ala Arg Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                325                 330                 335
Ile Gly Gln Ser Leu Trp Asp Val Ser Arg Ser Ser Thr Gly Asn Leu
            340                 345                 350
Val Glu Trp Phe Leu Leu Arg Lys Ala Tyr Lys Arg Asn Glu Leu Ala
        355                 360                 365
Pro Asn Lys Pro Asp Glu Arg Glu Leu Ala Arg Arg Gly Gly Tyr
370                 375                 380
Ala Gly Gly Tyr Val Lys Glu Pro Glu Arg Gly Leu Trp Asp Asn Ile
385                 390                 395                 400
Val Tyr Leu Asp Phe Arg Ser Leu Tyr Pro Ser Ile Ile Thr His
                405                 410                 415
Asn Val Ser Pro Asp Thr Leu Asn Arg Glu Gly Cys Lys Glu Tyr Asp
            420                 425                 430
Val Ala Pro Glu Val Gly His Lys Phe Cys Lys Asp Phe Pro Gly Phe
        435                 440                 445
Ile Pro Ser Leu Leu Gly Asp Leu Leu Glu Glu Arg Gln Lys Ile Lys
450                 455                 460
Arg Lys Met Lys Ala Thr Val Asp Pro Leu Glu Xaa Lys Xaa Leu Asp
465                 470                 475                 480
Tyr Arg Gln Arg Ala Ile Lys Ile Leu Ala Asn Ser Phe Tyr Gly Tyr
                485                 490                 495
Tyr Gly Tyr Ala Lys Ala Arg Trp Tyr Cys Lys Glu Cys Ala Glu Ser
            500                 505                 510
Val Thr Ala Trp Gly Arg Glu Tyr Ile Glu Met Val Ile Arg Glu Leu
        515                 520                 525
Glu Glu Lys Phe Gly Phe Lys Val Leu Tyr Ala Asp Thr Asp Gly Leu
530                 535                 540
His Ala Thr Ile Pro Gly Ala Asp Ala Glu Thr Val Lys Lys Lys Ala
545                 550                 555                 560
Lys Glu Phe Leu Lys Tyr Ile Asn Pro Lys Leu Pro Gly Leu Leu Glu
                565                 570                 575
Leu Glu Tyr Glu Gly Phe Tyr Val Arg Gly Phe Val Xaa Lys Lys
            580                 585                 590
Lys Tyr Ala Val Ile Asp Glu Glu Gly Lys Ile Thr Thr Arg Gly Leu
        595                 600                 605
Glu Ile Val Arg Arg Asp Trp Ser Glu Ile Ala Lys Glu Thr Gln Ala
```

```
                610             615             620
Arg Val Leu Glu Ala Ile Leu Lys His Gly Asp Val Glu Glu Xaa Val
625             630             635             640

Arg Ile Val Lys Glu Val Thr Glu Lys Leu Ser Lys Tyr Glu Val Pro
            645             650             655

Pro Glu Lys Leu Val Ile His Glu Gln Ile Thr Arg Asp Leu Arg Asp
        660             665             670

Tyr Lys Ala Thr Gly Pro His Val Ala Val Ala Lys Arg Leu Ala Ala
    675             680             685

Arg Gly Val Lys Ile Arg Pro Gly Thr Val Ile Ser Tyr Ile Val Leu
690             695             700

Lys Gly Ser Gly Arg Ile Gly Asp Arg Ala Ile Pro Ala Xaa Glu Phe
705             710             715             720

Asp Pro Thr Lys His Arg Tyr Asp Ala Glu Tyr Tyr Ile Glu Asn Gln
            725             730             735

Val Leu Pro Ala Val Glu Arg Ile Leu Lys Ala Phe Gly Tyr Arg Lys
        740             745             750

Glu Asp Leu Arg Tyr Gln Lys Thr Lys Gln Val Gly Leu Gly Ala Trp
    755             760             765

Leu Lys Val Lys Gly Lys Lys
770             775

<210> SEQ ID NO 15
<211> LENGTH: 775
<212> TYPE: PRT
<213> ORGANISM: Thermococcus sp. 9N-7
<220> FEATURE:
<221> NAME/KEY: Variant
<222> LOCATION: (144)..(144)
<223> OTHER INFORMATION: X= T, A
<220> FEATURE:
<221> NAME/KEY: Variant
<222> LOCATION: (153)..(153)
<223> OTHER INFORMATION: X= G, D
<220> FEATURE:
<221> NAME/KEY: Variant
<222> LOCATION: (408)..(408)
<223> OTHER INFORMATION: X= L, A
<220> FEATURE:
<221> NAME/KEY: Variant
<222> LOCATION: (409)..(409)
<223> OTHER INFORMATION: X= Y, A
<220> FEATURE:
<221> NAME/KEY: Variant
<222> LOCATION: (410)..(410)
<223> OTHER INFORMATION: X= P, V, A, I
<220> FEATURE:
<221> NAME/KEY: Variant
<222> LOCATION: (476)..(476)
<223> OTHER INFORMATION: X= K, W
<220> FEATURE:
<221> NAME/KEY: Variant
<222> LOCATION: (478)..(478)
<223> OTHER INFORMATION: X= L, S
<220> FEATURE:
<221> NAME/KEY: Variant
<222> LOCATION: (485)..(485)
<223> OTHER INFORMATION: X= A, L, V
<220> FEATURE:
<221> NAME/KEY: Variant
<222> LOCATION: (590)..(590)
<223> OTHER INFORMATION: X= T, I
<220> FEATURE:
<221> NAME/KEY: Variant
<222> LOCATION: (639)..(639)
<223> OTHER INFORMATION: X= A, V, F
<220> FEATURE:
<221> NAME/KEY: Variant
```

```
<222> LOCATION: (718)..(718)
<223> OTHER INFORMATION: X= D, N

<400> SEQUENCE: 15

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
            85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Xaa
130                 135                 140

Leu Tyr His Glu Gly Glu Glu Phe Xaa Thr Gly Pro Ile Leu Met Ile
145                 150                 155                 160

Ser Tyr Ala Asp Gly Ser Glu Ala Arg Val Ile Thr Trp Lys Lys Ile
            165                 170                 175

Asp Leu Pro Tyr Val Asp Val Ser Thr Glu Lys Glu Met Ile Lys
        180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Cys Glu
        210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Ser Thr Gly Asn Leu
        340                 345                 350

Val Glu Trp Phe Leu Leu Arg Lys Ala Tyr Lys Arg Asn Glu Leu Ala
    355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400
```

Val Tyr Leu Asp Phe Arg Ser Xaa Xaa Xaa Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Xaa Lys Xaa Leu Asp
465                 470                 475                 480

Tyr Arg Gln Arg Xaa Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Xaa Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Xaa Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
    675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Xaa Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775

<210> SEQ ID NO 16
<211> LENGTH: 775
<212> TYPE: PRT
<213> ORGANISM: Thermococcus sp. 9N-7

<400> SEQUENCE: 16

```
Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ala Ser Ile Ile Ile Thr His
                405                 410                 415
```

```
Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775

<210> SEQ ID NO 17
<211> LENGTH: 775
<212> TYPE: PRT
<213> ORGANISM: Thermococcus sp. 9N-7
<220> FEATURE:
<221> NAME/KEY: Variant
<222> LOCATION: (144)..(144)
<223> OTHER INFORMATION: X= T, A
```

```
<220> FEATURE:
<221> NAME/KEY: Variant
<222> LOCATION: (153)..(153)
<223> OTHER INFORMATION: X= G, D
<220> FEATURE:
<221> NAME/KEY: Variant
<222> LOCATION: (476)..(476)
<223> OTHER INFORMATION: X= K, W
<220> FEATURE:
<221> NAME/KEY: Variant
<222> LOCATION: (478)..(478)
<223> OTHER INFORMATION: X= L, S
<220> FEATURE:
<221> NAME/KEY: Variant
<222> LOCATION: (590)..(590)
<223> OTHER INFORMATION: X= T, I
<220> FEATURE:
<221> NAME/KEY: Variant
<222> LOCATION: (639)..(639)
<223> OTHER INFORMATION: X= A, V, F
<220> FEATURE:
<221> NAME/KEY: Variant
<222> LOCATION: (718)..(718)
<223> OTHER INFORMATION: X= D, N

<400> SEQUENCE: 17
```

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Xaa
    130                 135                 140

Leu Tyr His Glu Gly Glu Glu Phe Xaa Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu

```
            275                 280                 285
Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
                340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
            370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ala Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Arg Lys Met Lys Ala Thr Val Asp Pro Leu Glu Xaa Lys Xaa Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
                500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Xaa Lys Lys
                580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
            610                 615                 620

Arg Val Leu Glu Ala Ile Leu Lys His Gly Asp Val Glu Glu Xaa Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
690                 695                 700
```

-continued

```
Lys Gly Ser Gly Arg Ile Gly Asp Arg Ala Ile Pro Ala Xaa Glu Phe
705                 710                 715                 720

Asp Pro Thr Lys His Arg Tyr Asp Ala Glu Tyr Tyr Ile Glu Asn Gln
            725                 730                 735

Val Leu Pro Ala Val Glu Arg Ile Leu Lys Ala Phe Gly Tyr Arg Lys
        740                 745                 750

Glu Asp Leu Arg Tyr Gln Lys Thr Lys Gln Val Gly Leu Gly Ala Trp
            755                 760                 765

Leu Lys Val Lys Gly Lys Lys
770                 775

<210> SEQ ID NO 18
<211> LENGTH: 775
<212> TYPE: PRT
<213> ORGANISM: Pyrococcus furiosus

<400> SEQUENCE: 18

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
```

```
              290                 295                 300
Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Phe Leu Leu Arg Lys Ala Tyr Glu Arg Asn Glu Val Ala
            355                 360                 365

Pro Asn Lys Pro Ser Glu Glu Glu Tyr Gln Arg Arg Leu Arg Glu Ser
        370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
                420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
        450                 455                 460

Lys Thr Lys Met Lys Glu Thr Gln Asp Pro Ile Glu Lys Ile Leu Leu
465                 470                 475                 480

Asp Tyr Arg Gln Lys Leu Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
                580                 585                 590

Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
        610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
        690                 695                 700

Leu Arg Gly Asp Gly Pro Ile Ser Asn Arg Ala Ile Leu Ala Glu Glu
705                 710                 715                 720
```

-continued

```
Tyr Asp Pro Lys Lys His Lys Tyr Asp Ala Glu Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
            755                 760                 765

Trp Leu Asn Ile Lys Lys Ser
            770                 775

<210> SEQ ID NO 19
<211> LENGTH: 775
<212> TYPE: PRT
<213> ORGANISM: Pyrococcus furiosus
<220> FEATURE:
<221> NAME/KEY: Variant
<222> LOCATION: (144)..(144)
<223> OTHER INFORMATION: X= T, A
<220> FEATURE:
<221> NAME/KEY: Variant
<222> LOCATION: (153)..(153)
<223> OTHER INFORMATION: X= G, D
<220> FEATURE:
<221> NAME/KEY: Variant
<222> LOCATION: (477)..(477)
<223> OTHER INFORMATION: X= K, W
<220> FEATURE:
<221> NAME/KEY: Variant
<222> LOCATION: (479)..(479)
<223> OTHER INFORMATION: X= L, S
<220> FEATURE:
<221> NAME/KEY: Variant
<222> LOCATION: (591)..(591)
<223> OTHER INFORMATION: X= T, I
<220> FEATURE:
<221> NAME/KEY: Variant
<222> LOCATION: (640)..(640)
<223> OTHER INFORMATION: X= A, V, F
<220> FEATURE:
<221> NAME/KEY: Variant
<222> LOCATION: (719)..(719)
<223> OTHER INFORMATION: X= E, N

<400> SEQUENCE: 19

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Ala Ile Ala Xaa
    130                 135                 140

Leu Tyr His Glu Gly Glu Glu Phe Xaa Lys Gly Pro Ile Ile Met Ile
145                 150                 155                 160
```

```
Ser Tyr Ala Asp Glu Asn Glu Ala Lys Val Ile Thr Trp Lys Asn Ile
            165                 170                 175
Asp Leu Pro Tyr Val Glu Val Ser Ser Glu Arg Glu Met Ile Lys
        180                 185                 190
Arg Phe Leu Arg Ile Ile Arg Glu Lys Asp Pro Asp Ile Ile Val Thr
            195                 200                 205
Tyr Asn Gly Asp Ser Phe Asp Phe Pro Tyr Leu Ala Lys Arg Ala Glu
    210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
                260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Ser Gly Glu Asn
    290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
        355                 360                 365
Pro Asn Lys Pro Ser Glu Glu Glu Tyr Gln Arg Arg Leu Arg Glu Ser
    370                 375                 380
Tyr Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Thr
                405                 410                 415
His Asn Val Ser Pro Asp Thr Leu Asn Leu Glu Gly Cys Lys Asn Tyr
            420                 425                 430
Asp Ile Ala Pro Gln Val Gly His Lys Phe Cys Lys Asp Ile Pro Gly
        435                 440                 445
Phe Ile Pro Ser Leu Leu Gly His Leu Leu Glu Glu Arg Gln Lys Ile
    450                 455                 460
Lys Thr Lys Met Lys Glu Thr Gln Asp Pro Ile Glu Xaa Ile Xaa Leu
465                 470                 475                 480
Asp Tyr Arg Gln Lys Leu Ile Lys Leu Leu Ala Asn Ser Phe Tyr Gly
                485                 490                 495
Tyr Tyr Gly Tyr Ala Lys Ala Arg Trp Tyr Cys Lys Glu Cys Ala Glu
            500                 505                 510
Ser Val Thr Ala Trp Gly Arg Lys Tyr Ile Glu Leu Val Trp Lys Glu
        515                 520                 525
Leu Glu Glu Lys Phe Gly Phe Lys Val Leu Tyr Ile Asp Thr Asp Gly
    530                 535                 540
Leu Tyr Ala Thr Ile Pro Gly Gly Glu Ser Glu Ile Lys Lys Lys
545                 550                 555                 560
Ala Leu Glu Phe Val Lys Tyr Ile Asn Ser Lys Leu Pro Gly Leu Leu
                565                 570                 575
Glu Leu Glu Tyr Glu Gly Phe Tyr Lys Arg Gly Phe Phe Val Xaa Lys
```

-continued

```
                580                 585                 590
Lys Arg Tyr Ala Val Ile Asp Glu Glu Gly Lys Val Ile Thr Arg Gly
            595                 600                 605
Leu Glu Ile Val Arg Arg Asp Trp Ser Glu Ile Ala Lys Glu Thr Gln
        610                 615                 620
Ala Arg Val Leu Glu Thr Ile Leu Lys His Gly Asp Val Glu Glu Xaa
625                 630                 635                 640
Val Arg Ile Val Lys Glu Val Ile Gln Lys Leu Ala Asn Tyr Glu Ile
                645                 650                 655
Pro Pro Glu Lys Leu Ala Ile Tyr Glu Gln Ile Thr Arg Pro Leu His
            660                 665                 670
Glu Tyr Lys Ala Ile Gly Pro His Val Ala Val Ala Lys Lys Leu Ala
        675                 680                 685
Ala Lys Gly Val Lys Ile Lys Pro Gly Met Val Ile Gly Tyr Ile Val
    690                 695                 700
Leu Arg Gly Asp Gly Pro Ile Ser Asn Arg Ala Ile Leu Ala Xaa Glu
705                 710                 715                 720
Tyr Asp Pro Lys Lys His Lys Tyr Asp Ala Glu Tyr Tyr Ile Glu Asn
                725                 730                 735
Gln Val Leu Pro Ala Val Leu Arg Ile Leu Glu Gly Phe Gly Tyr Arg
            740                 745                 750
Lys Glu Asp Leu Arg Tyr Gln Lys Thr Arg Gln Val Gly Leu Thr Ser
        755                 760                 765
Trp Leu Asn Ile Lys Lys Ser
    770                 775

<210> SEQ ID NO 20
<211> LENGTH: 775
<212> TYPE: PRT
<213> ORGANISM: Pyrococcus furiosus
<220> FEATURE:
<221> NAME/KEY: Variant
<222> LOCATION: (144)..(144)
<223> OTHER INFORMATION: X= T, A
<220> FEATURE:
<221> NAME/KEY: Variant
<222> LOCATION: (153)..(153)
<223> OTHER INFORMATION: X= G, D
<220> FEATURE:
<221> NAME/KEY: Variant
<222> LOCATION: (409)..(409)
<223> OTHER INFORMATION: X= L, A
<220> FEATURE:
<221> NAME/KEY: Variant
<222> LOCATION: (410)..(410)
<223> OTHER INFORMATION: X= Y, A
<220> FEATURE:
<221> NAME/KEY: Variant
<222> LOCATION: (411)..(411)
<223> OTHER INFORMATION: X= P, V, A, I
<220> FEATURE:
<221> NAME/KEY: Variant
<222> LOCATION: (477)..(477)
<223> OTHER INFORMATION: X= K, W
<220> FEATURE:
<221> NAME/KEY: Variant
<222> LOCATION: (479)..(479)
<223> OTHER INFORMATION: X= L, S
<220> FEATURE:
<221> NAME/KEY: Variant
<222> LOCATION: (591)..(591)
<223> OTHER INFORMATION: X= T, I
<220> FEATURE:
<221> NAME/KEY: Variant
<222> LOCATION: (640)..(640)
<223> OTHER INFORMATION: X= A, V, F
```

-continued

```
<220> FEATURE:
<221> NAME/KEY: Variant
<222> LOCATION: (719)..(719)
<223> OTHER INFORMATION: X= E, N

<400> SEQUENCE: 20
```

| | | | | | | | | | | | | | | |
|---|---|---|---|---|---|---|---|---|---|---|---|---|---|---|
| Met | Ile | Leu | Asp | Val | Asp | Tyr | Ile | Thr | Glu | Glu | Gly | Lys | Pro | Val | Ile |
| 1 | | | | 5 | | | | | 10 | | | | | 15 |

Arg Leu Phe Lys Lys Glu Asn Gly Lys Phe Lys Ile Glu His Asp Arg
             20                  25                  30

Thr Phe Arg Pro Tyr Ile Tyr Ala Leu Leu Arg Asp Asp Ser Lys Ile
         35                  40                  45

Glu Glu Val Lys Lys Ile Thr Gly Glu Arg His Gly Lys Ile Val Arg
50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
             85                  90                  95

Arg Glu Lys Val Arg Glu His Pro Ala Val Val Asp Ile Phe Glu Tyr
             100                 105                 110

Asp Ile Pro Phe Ala Lys Arg Tyr Leu Ile Asp Lys Gly Leu Ile Pro
         115                 120                 125

Met Glu Gly Glu Glu Glu Leu Lys Ile Leu Ala Phe Ala Ile Ala Xaa
130                 135                 140

Leu Tyr His Glu Gly Glu Glu Phe Xaa Lys Gly Pro Ile Ile Met Ile
145                 150                 155                 160

Ser Tyr Ala Asp Glu Asn Glu Ala Lys Val Ile Thr Trp Lys Asn Ile
             165                 170                 175

Asp Leu Pro Tyr Val Glu Val Ser Ser Glu Arg Glu Met Ile Lys
             180                 185                 190

Arg Phe Leu Arg Ile Ile Arg Glu Lys Asp Pro Asp Ile Ile Val Thr
         195                 200                 205

Tyr Asn Gly Asp Ser Phe Asp Phe Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
             245                 250                 255

His Phe Asp Leu Tyr His Val Ile Thr Arg Thr Ile Asn Leu Pro Thr
             260                 265                 270

Tyr Thr Leu Glu Ala Val Tyr Glu Ala Ile Phe Gly Lys Pro Lys Glu
         275                 280                 285

Lys Val Tyr Ala Asp Glu Ile Ala Lys Ala Trp Glu Ser Gly Glu Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
             325                 330                 335

Val Gly Gln Pro Leu Trp Asp Val Ser Arg Ser Ser Thr Gly Asn Leu
         340                 345                 350

Val Glu Trp Phe Leu Leu Arg Lys Ala Tyr Glu Arg Asn Glu Val Ala
             355                 360                 365

Pro Asn Lys Pro Ser Glu Glu Glu Tyr Gln Arg Arg Leu Arg Glu Ser
370                 375                 380

```
Tyr Thr Gly Gly Phe Val Lys Glu Pro Glu Lys Gly Leu Trp Glu Asn
385                 390                 395                 400

Ile Val Tyr Leu Asp Phe Arg Ala Xaa Xaa Xaa Ser Ile Ile Ile Thr
            405                 410                 415

His Asn Val Ser Pro Asp Thr Leu Asn Leu Glu Gly Cys Lys Asn Tyr
        420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
        450                 455                 460

Lys Thr Lys Met Lys Glu Thr Gln Asp Pro Ile Glu Xaa Ile Xaa Leu
465                 470                 475                 480

Asp Tyr Arg Gln Lys Leu Ile Lys Leu Leu Ala Asn Ser Phe Tyr Gly
            485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Xaa Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
610                 615                 620

Ala Arg Val Leu Glu Thr Ile Leu Lys His Gly Asp Val Glu Glu Xaa
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Leu Ala
        675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Xaa Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
        770                 775

<210> SEQ ID NO 21
<211> LENGTH: 774
<212> TYPE: PRT
```

<213> ORGANISM: Thermococcus kodakaraensis

<400> SEQUENCE: 21

```
Met Ile Leu Asp Thr Asp Tyr Ile Thr Glu Asp Gly Lys Pro Val Ile
1               5                   10                  15
Arg Ile Phe Lys Lys Glu Asn Gly Glu Phe Lys Ile Glu Tyr Asp Arg
            20                  25                  30
Thr Phe Glu Pro Tyr Phe Tyr Ala Leu Leu Lys Asp Asp Ser Ala Ile
        35                  40                  45
Glu Glu Val Lys Lys Ile Thr Ala Glu Arg His Gly Thr Val Val Thr
    50                  55                  60
Val Lys Arg Val Glu Lys Val Gln Lys Lys Phe Leu Gly Arg Pro Val
65                  70                  75                  80
Glu Val Trp Lys Leu Tyr Phe Thr His Pro Gln Asp Val Pro Ala Ile
                85                  90                  95
Arg Asp Lys Ile Arg Glu His Pro Ala Val Ile Asp Ile Tyr Glu Tyr
            100                 105                 110
Asp Ile Pro Phe Ala Lys Arg Tyr Leu Ile Asp Lys Gly Leu Val Pro
        115                 120                 125
Met Glu Gly Asp Glu Glu Leu Lys Met Leu Ala Phe Ala Ile Ala Thr
    130                 135                 140
Leu Tyr His Glu Gly Glu Glu Phe Ala Glu Gly Pro Ile Leu Met Ile
145                 150                 155                 160
Ser Tyr Ala Asp Glu Glu Gly Ala Arg Val Ile Thr Trp Lys Asn Val
                165                 170                 175
Asp Leu Pro Tyr Val Asp Val Val Ser Thr Glu Arg Glu Met Ile Lys
            180                 185                 190
Arg Phe Leu Arg Val Val Lys Glu Lys Asp Pro Asp Val Leu Ile Thr
        195                 200                 205
Tyr Asn Gly Asp Asn Phe Asp Phe Ala Tyr Leu Lys Lys Arg Cys Glu
    210                 215                 220
Lys Leu Gly Ile Asn Phe Ala Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
            260                 265                 270
Tyr Thr Leu Glu Ala Val Tyr Glu Ala Val Phe Gly Gln Pro Lys Glu
        275                 280                 285
Lys Val Tyr Ala Glu Glu Ile Thr Thr Ala Trp Glu Thr Gly Glu Asn
    290                 295                 300
Leu Glu Arg Val Ala Arg Tyr Ser Met Glu Asp Ala Lys Val Thr Tyr
305                 310                 315                 320
Glu Leu Gly Lys Glu Phe Leu Pro Met Glu Ala Gln Leu Ser Arg Leu
                325                 330                 335
Ile Gly Gln Ser Leu Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Lys Glu Leu Ala Arg Arg Gln Ser Tyr
    370                 375                 380
Glu Gly Gly Tyr Val Lys Glu Pro Glu Arg Gly Leu Trp Glu Asn Ile
385                 390                 395                 400
```

```
Val Tyr Leu Asp Phe Arg Ser Leu Tyr Pro Ser Ile Ile Ile Thr His
                    405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys
        450                 455                 460

Lys Lys Met Lys Ala Thr Ile Asp Pro Ile Glu Arg Lys Leu Leu Asp
465                 470                 475                 480

Tyr Arg Gln Arg Leu Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
            515                 520                 525

Glu Glu Lys Tyr Gly Phe Lys Val Ile Tyr Ser Asp Thr Asp Gly Phe
        530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770

<210> SEQ ID NO 22
<211> LENGTH: 774
<212> TYPE: PRT
<213> ORGANISM: Thermococcus kodakaraensis
<220> FEATURE:
<221> NAME/KEY: Variant
```

```
<222> LOCATION: (144)..(144)
<223> OTHER INFORMATION: X= T, A
<220> FEATURE:
<221> NAME/KEY: Variant
<222> LOCATION: (153)..(153)
<223> OTHER INFORMATION: X= A, D
<220> FEATURE:
<221> NAME/KEY: Variant
<222> LOCATION: (476)..(476)
<223> OTHER INFORMATION: X= R, W
<220> FEATURE:
<221> NAME/KEY: Variant
<222> LOCATION: (478)..(478)
<223> OTHER INFORMATION: X= L, S
<220> FEATURE:
<221> NAME/KEY: Variant
<222> LOCATION: (590)..(590)
<223> OTHER INFORMATION: X= T, I
<220> FEATURE:
<221> NAME/KEY: Variant
<222> LOCATION: (639)..(639)
<223> OTHER INFORMATION: X= A, V, F
<220> FEATURE:
<221> NAME/KEY: Variant
<222> LOCATION: (718)..(718)
<223> OTHER INFORMATION: X= D, N

<400> SEQUENCE: 22

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Ala Ile Ala Xaa
    130                 135                 140

Leu Tyr His Glu Gly Glu Glu Phe Xaa Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270
```

```
Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Xaa Lys Xaa Leu Asp
465                 470                 475                 480

Tyr Arg Gln Arg Leu Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Xaa Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Xaa Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685
```

```
Arg Gly Val Lys Ile Arg Pro Gly Thr Val Ile Ser Tyr Ile Val Leu
    690                 695                 700
Lys Gly Ser Gly Arg Ile Gly Asp Arg Ala Ile Pro Phe Xaa Glu Phe
705                 710                 715                 720
Asp Pro Thr Lys His Lys Tyr Asp Ala Glu Tyr Tyr Ile Glu Asn Gln
                725                 730                 735
Val Leu Pro Ala Val Glu Arg Ile Leu Arg Ala Phe Gly Tyr Arg Lys
            740                 745                 750
Glu Asp Leu Arg Tyr Gln Lys Thr Arg Gln Val Gly Leu Ser Ala Trp
        755                 760                 765
Leu Lys Pro Lys Gly Thr
    770

<210> SEQ ID NO 23
<211> LENGTH: 774
<212> TYPE: PRT
<213> ORGANISM: Thermococcus kodakaraensis
<220> FEATURE:
<221> NAME/KEY: Variant
<222> LOCATION: (144)..(144)
<223> OTHER INFORMATION: X= T, A
<220> FEATURE:
<221> NAME/KEY: Variant
<222> LOCATION: (153)..(153)
<223> OTHER INFORMATION: X= A, D
<220> FEATURE:
<221> NAME/KEY: Variant
<222> LOCATION: (408)..(408)
<223> OTHER INFORMATION: X= L, A
<220> FEATURE:
<221> NAME/KEY: Variant
<222> LOCATION: (409)..(409)
<223> OTHER INFORMATION: X= Y, A
<220> FEATURE:
<221> NAME/KEY: Variant
<222> LOCATION: (410)..(410)
<223> OTHER INFORMATION: X= P, V, A, I
<220> FEATURE:
<221> NAME/KEY: Variant
<222> LOCATION: (476)..(476)
<223> OTHER INFORMATION: X= R, W
<220> FEATURE:
<221> NAME/KEY: Variant
<222> LOCATION: (478)..(478)
<223> OTHER INFORMATION: X= L, S
<220> FEATURE:
<221> NAME/KEY: Variant
<222> LOCATION: (590)..(590)
<223> OTHER INFORMATION: X= T, I
<220> FEATURE:
<221> NAME/KEY: Variant
<222> LOCATION: (639)..(639)
<223> OTHER INFORMATION: X= A, V, F
<220> FEATURE:
<221> NAME/KEY: Variant
<222> LOCATION: (718)..(718)
<223> OTHER INFORMATION: X= D, N

<400> SEQUENCE: 23

Met Ile Leu Asp Thr Asp Tyr Ile Thr Glu Asp Gly Lys Pro Val Ile
1               5                   10                  15
Arg Ile Phe Lys Lys Glu Asn Gly Glu Phe Lys Ile Glu Tyr Asp Arg
            20                  25                  30
Thr Phe Glu Pro Tyr Phe Tyr Ala Leu Leu Lys Asp Asp Ser Ala Ile
        35                  40                  45
Glu Glu Val Lys Lys Ile Thr Ala Glu Arg His Gly Thr Val Val Thr
    50                  55                  60
Val Lys Arg Val Glu Lys Val Gln Lys Lys Phe Leu Gly Arg Pro Val
```

-continued

```
                65                  70                  75                  80
Glu Val Trp Lys Leu Tyr Phe Thr His Pro Gln Asp Val Pro Ala Ile
                            85                  90                  95
Arg Asp Lys Ile Arg Glu His Pro Ala Val Ile Asp Ile Tyr Glu Tyr
                100                 105                 110
Asp Ile Pro Phe Ala Lys Arg Tyr Leu Ile Asp Lys Gly Leu Val Pro
                115                 120                 125
Met Glu Gly Asp Glu Glu Leu Lys Met Leu Ala Phe Ala Ile Ala Xaa
            130                 135                 140
Leu Tyr His Glu Gly Glu Phe Xaa Glu Gly Pro Ile Leu Met Ile
145                 150                 155                 160
Ser Tyr Ala Asp Glu Glu Gly Ala Arg Val Ile Thr Trp Lys Asn Val
                165                 170                 175
Asp Leu Pro Tyr Val Asp Val Ser Thr Glu Arg Glu Met Ile Lys
                180                 185                 190
Arg Phe Leu Arg Val Val Lys Glu Lys Asp Pro Asp Val Leu Ile Thr
                195                 200                 205
Tyr Asn Gly Asp Asn Phe Asp Phe Ala Tyr Leu Lys Lys Arg Cys Glu
                210                 215                 220
Lys Leu Gly Ile Asn Phe Ala Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
                260                 265                 270
Tyr Thr Leu Glu Ala Val Tyr Glu Ala Val Phe Gly Gln Pro Lys Glu
                275                 280                 285
Lys Val Tyr Ala Glu Glu Ile Thr Thr Ala Trp Glu Thr Gly Glu Asn
                290                 295                 300
Leu Glu Arg Val Ala Arg Tyr Ser Met Glu Asp Ala Lys Val Thr Tyr
305                 310                 315                 320
Glu Leu Gly Lys Glu Phe Leu Pro Met Glu Ala Gln Leu Ser Arg Leu
                325                 330                 335
Ile Gly Gln Ser Leu Trp Asp Val Ser Arg Ser Ser Thr Gly Asn Leu
                340                 345                 350
Val Glu Trp Phe Leu Leu Arg Lys Ala Tyr Glu Arg Asn Glu Leu Ala
                355                 360                 365
Pro Asn Lys Pro Asp Glu Lys Glu Leu Ala Arg Arg Gln Ser Tyr
                370                 375                 380
Glu Gly Gly Tyr Val Lys Glu Pro Glu Arg Gly Leu Trp Glu Asn Ile
385                 390                 395                 400
Val Tyr Leu Asp Phe Arg Ser Xaa Xaa Xaa Ser Ile Ile Ile Thr His
                405                 410                 415
Asn Val Ser Pro Asp Thr Leu Asn Arg Glu Gly Cys Lys Glu Tyr Asp
                420                 425                 430
Val Ala Pro Gln Val Gly His Arg Phe Cys Lys Asp Phe Pro Gly Phe
                435                 440                 445
Ile Pro Ser Leu Leu Gly Asp Leu Leu Glu Glu Arg Gln Lys Ile Lys
                450                 455                 460
Lys Lys Met Lys Ala Thr Ile Asp Pro Ile Glu Xaa Lys Xaa Leu Asp
465                 470                 475                 480
Tyr Arg Gln Arg Leu Ile Lys Ile Leu Ala Asn Ser Tyr Tyr Gly Tyr
                485                 490                 495
```

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
            515                 520                 525

Glu Glu Lys Tyr Gly Phe Lys Val Ile Tyr Ser Asp Thr Asp Gly Phe
        530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Xaa Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
            610                 615                 620

Arg Val Leu Glu Ala Leu Leu Lys Asp Gly Asp Val Glu Lys Xaa Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
                660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Phe Xaa Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
            755                 760                 765

Leu Lys Pro Lys Gly Thr
    770

<210> SEQ ID NO 24
<211> LENGTH: 784
<212> TYPE: PRT
<213> ORGANISM: Methanococcus maripaludis

<400> SEQUENCE: 24

Met Glu Ser Leu Ile Asp Leu Asp Tyr Asn Ser Asp Asp Leu Cys Ile
1               5                   10                  15

Tyr Leu Tyr Leu Ile Asn Ser Ile Ile Lys Glu Lys Asp Phe Lys Pro
            20                  25                  30

Tyr Phe Tyr Val Asn Ser Thr Asp Lys Glu Gln Ile Leu Glu Phe Leu
        35                  40                  45

Lys Asp Tyr Glu Lys Lys His Lys Leu Asp Ser Glu Ile Ser Lys Met
    50                  55                  60

Ile Glu Asn Ile Glu Thr Val Lys Lys Ile Val Phe Asp Glu Asn Tyr
65                  70                  75                  80

Gln Glu Lys Glu Leu Ser Lys Val Thr Val Lys Tyr Pro Asn Asn Val

```
            85                  90                  95
Lys Thr Val Arg Glu Ile Leu Met Glu Phe Glu Arg Leu Tyr Glu Tyr
            100                 105                 110

Asp Ile Pro Phe Val Arg Arg Tyr Leu Ile Asp Asn Ser Val Ile Pro
            115                 120                 125

Thr Ser Thr Trp Asp Phe Glu Asn Asn Lys Lys Ile Asp Asn Lys Ile
            130                 135                 140

Pro Asp Phe Lys Thr Val Ser Phe Ala Ile Ala Val Tyr Cys Asn Lys
145                 150                 155                 160

Glu Pro Asn Pro Lys Lys Asp Pro Ile Ile Met Ala Ser Phe Ser Ser
            165                 170                 175

Lys Asp Phe Asn Thr Val Val Ser Thr Lys Lys Phe Asp His Glu Lys
            180                 185                 190

Leu Glu Tyr Val Lys Asp Glu Lys Glu Leu Ile Lys Arg Ile Ile Glu
            195                 200                 205

Ile Leu Lys Glu Tyr Asp Ile Ile Tyr Thr Tyr Asn Gly Asp Asn Phe
            210                 215                 220

Asp Phe Pro Tyr Leu Lys Lys Arg Ala Glu Ser Phe Gly Leu Glu Leu
225                 230                 235                 240

Lys Leu Gly Lys Asn Asp Glu Lys Ile Lys Ile Thr Lys Gly Gly Met
            245                 250                 255

Asn Ser Lys Ser Tyr Ile Pro Gly Arg Val His Ile Asp Leu Tyr Pro
            260                 265                 270

Ile Ala Arg Arg Leu Leu Asn Leu Thr Lys Tyr Arg Leu Glu Asn Val
            275                 280                 285

Thr Glu Ala Leu Phe Asp Val Lys Lys Val Asp Val Gly His Glu Asn
            290                 295                 300

Ile Pro Lys Met Trp Asp Asn Leu Asp Glu Thr Leu Val Glu Tyr Ser
305                 310                 315                 320

His Gln Asp Ala Tyr Tyr Thr Gln Arg Ile Gly Glu Gln Phe Leu Pro
            325                 330                 335

Leu Glu Ile Met Phe Ser Arg Val Val Asn Gln Ser Leu Tyr Asp Ile
            340                 345                 350

Asn Arg Met Ser Ser Ser Gln Met Val Glu Tyr Leu Leu Leu Lys Asn
            355                 360                 365

Ser Tyr Lys Met Gly Val Ile Ala Pro Asn Arg Pro Ser Gly Lys Glu
            370                 375                 380

Tyr Gln Lys Arg Ile Arg Ser Ser Tyr Glu Gly Gly Tyr Val Lys Glu
385                 390                 395                 400

Pro Leu Lys Gly Ile His Glu Asp Ile Val Ser Met Asp Phe Leu Ser
            405                 410                 415

Leu Tyr Pro Ser Ile Ile Met Ser His Asn Leu Ser Pro Glu Thr Ile
            420                 425                 430

Asp Cys Thr Cys Cys Ser Asp Glu Glu Asn Gly Glu Asn Glu Glu Ile
            435                 440                 445

Leu Gly His Lys Phe Cys Lys Lys Ser Ile Gly Ile Ile Pro Lys Thr
            450                 455                 460

Leu Met Asp Leu Ile Asn Arg Arg Lys Val Lys Val Leu Arg
465                 470                 475                 480

Glu Lys Ala Glu Lys Gly Glu Phe Asp Glu Glu Tyr Gln Ile Leu Asp
            485                 490                 495

Tyr Glu Gln Arg Leu Ile Lys Val Leu Ala Asn Ser His Tyr Gly Tyr
            500                 505                 510
```

-continued

```
Leu Ala Phe Pro Met Ala Arg Trp Tyr Ser Arg Asp Cys Ala Glu Ile
            515                 520                 525

Thr Thr His Leu Gly Arg Gln Tyr Ile Gln Lys Thr Ile Glu Glu Ala
    530                 535                 540

Glu Asn Phe Gly Phe Lys Val Ile Tyr Ala Asp Thr Asp Gly Phe Tyr
545                 550                 555                 560

Ser Lys Trp Ala Asp Asp Lys Glu Lys Leu Ser Lys Tyr Glu Leu Leu
                565                 570                 575

Glu Lys Thr Arg Glu Phe Leu Lys Asn Ile Asn Asn Thr Leu Pro Gly
            580                 585                 590

Glu Met Glu Leu Glu Phe Glu Gly Tyr Phe Lys Arg Gly Ile Phe Val
        595                 600                 605

Thr Lys Lys Lys Tyr Ala Leu Ile Asp Glu Asn Glu Lys Ile Thr Val
    610                 615                 620

Lys Gly Leu Glu Val Val Arg Arg Asp Trp Ser Asn Val Ser Lys Asn
625                 630                 635                 640

Thr Gln Lys Asn Val Leu Asn Ala Leu Leu Lys Gly Ser Val Glu
                645                 650                 655

Asn Ala Lys Lys Val Ile Gln Asp Thr Ile Lys Glu Leu Lys Asp Gly
            660                 665                 670

Lys Val Asn Asn Glu Asp Leu Leu Ile His Thr Gln Leu Thr Lys Arg
        675                 680                 685

Ile Glu Asp Tyr Lys Thr Thr Ala Pro His Val Glu Val Ala Lys Lys
    690                 695                 700

Ile Leu Lys Ser Gly Asn Arg Val Asn Thr Gly Asp Val Ile Ser Tyr
705                 710                 715                 720

Ile Ile Thr Ser Gly Asn Lys Ser Ile Ser Glu Arg Ala Glu Ile Leu
                725                 730                 735

Glu Asn Ala Lys Asn Tyr Asp Thr Asn Tyr Tyr Ile Glu Asn Gln Ile
            740                 745                 750

Leu Pro Pro Val Ile Arg Leu Met Glu Ala Leu Gly Ile Thr Lys Asp
        755                 760                 765

Glu Leu Lys Asp Ser Lys Lys Gln Tyr Thr Leu His His Phe Leu Lys
    770                 775                 780
```

<210> SEQ ID NO 25
<211> LENGTH: 784
<212> TYPE: PRT
<213> ORGANISM: Methanococcus maripaludis
<220> FEATURE:
<221> NAME/KEY: Variant
<222> LOCATION: (156)..(156)
<223> OTHER INFORMATION: X= V, A
<220> FEATURE:
<221> NAME/KEY: Variant
<222> LOCATION: (165)..(165)
<223> OTHER INFORMATION: X= K, D
<220> FEATURE:
<221> NAME/KEY: Variant
<222> LOCATION: (492)..(492)
<223> OTHER INFORMATION: X= Y, W
<220> FEATURE:
<221> NAME/KEY: Variant
<222> LOCATION: (494)..(494)
<223> OTHER INFORMATION: X= I, S
<220> FEATURE:
<221> NAME/KEY: Variant
<222> LOCATION: (609)..(609)
<223> OTHER INFORMATION: X= T, I
<220> FEATURE:
<221> NAME/KEY: Variant

<222> LOCATION: (658)..(658)
<223> OTHER INFORMATION: X= A, V, F

<400> SEQUENCE: 25

```
Met Glu Ser Leu Ile Asp Leu Asp Tyr Asn Ser Asp Leu Cys Ile
1               5                   10                  15

Tyr Leu Tyr Leu Ile Asn Ser Ile Ile Lys Glu Lys Asp Phe Lys Pro
                20                  25                  30

Tyr Phe Tyr Val Asn Ser Thr Asp Lys Glu Gln Ile Leu Glu Phe Leu
            35                  40                  45

Lys Asp Tyr Glu Lys Lys His Lys Leu Asp Ser Glu Ile Ser Lys Met
        50                  55                  60

Ile Glu Asn Ile Glu Thr Val Lys Lys Ile Val Phe Asp Glu Asn Tyr
65                  70                  75                  80

Gln Glu Lys Glu Leu Ser Lys Val Thr Val Lys Tyr Pro Asn Asn Val
                85                  90                  95

Lys Thr Val Arg Glu Ile Leu Met Glu Phe Glu Arg Leu Tyr Glu Tyr
            100                 105                 110

Asp Ile Pro Phe Val Arg Arg Tyr Leu Ile Asp Asn Ser Val Ile Pro
        115                 120                 125

Thr Ser Thr Trp Asp Phe Glu Asn Asn Lys Lys Ile Asp Asn Lys Ile
130                 135                 140

Pro Asp Phe Lys Thr Val Ser Phe Ala Ile Ala Xaa Tyr Cys Asn Lys
145                 150                 155                 160

Glu Pro Asn Pro Xaa Lys Asp Pro Ile Ile Met Ala Ser Phe Ser Ser
                165                 170                 175

Lys Asp Phe Asn Thr Val Val Ser Thr Lys Lys Phe Asp His Glu Lys
            180                 185                 190

Leu Glu Tyr Val Lys Asp Glu Lys Glu Leu Ile Lys Arg Ile Ile Glu
        195                 200                 205

Ile Leu Lys Glu Tyr Asp Ile Ile Tyr Thr Tyr Asn Gly Asp Asn Phe
210                 215                 220

Asp Phe Pro Tyr Leu Lys Lys Arg Ala Glu Ser Phe Gly Leu Glu Leu
225                 230                 235                 240

Lys Leu Gly Lys Asn Asp Glu Lys Ile Lys Ile Thr Lys Gly Gly Met
                245                 250                 255

Asn Ser Lys Ser Tyr Ile Pro Gly Arg Val His Ile Asp Leu Tyr Pro
            260                 265                 270

Ile Ala Arg Arg Leu Leu Asn Leu Thr Lys Tyr Arg Leu Glu Asn Val
        275                 280                 285

Thr Glu Ala Leu Phe Asp Val Lys Lys Val Asp Val Gly His Glu Asn
290                 295                 300

Ile Pro Lys Met Trp Asp Asn Leu Asp Glu Thr Leu Val Glu Tyr Ser
305                 310                 315                 320

His Gln Asp Ala Tyr Tyr Thr Gln Arg Ile Gly Glu Gln Phe Leu Pro
                325                 330                 335

Leu Glu Ile Met Phe Ser Arg Val Val Asn Gln Ser Leu Tyr Asp Ile
            340                 345                 350

Asn Arg Met Ser Ser Ser Gln Met Val Glu Tyr Leu Leu Leu Lys Asn
        355                 360                 365

Ser Tyr Lys Met Gly Val Ile Ala Pro Asn Arg Pro Ser Gly Lys Glu
370                 375                 380

Tyr Gln Lys Arg Ile Arg Ser Ser Tyr Glu Gly Gly Tyr Val Lys Glu
385                 390                 395                 400
```

```
Pro Leu Lys Gly Ile His Glu Asp Ile Val Ser Met Asp Phe Leu Ser
                405                 410                 415

Leu Tyr Pro Ser Ile Ile Met Ser His Asn Leu Ser Pro Glu Thr Ile
            420                 425                 430

Asp Cys Thr Cys Cys Ser Asp Glu Glu Asn Gly Glu Asn Glu Glu Ile
        435                 440                 445

Leu Gly His Lys Phe Cys Lys Lys Ser Ile Gly Ile Ile Pro Lys Thr
    450                 455                 460

Leu Met Asp Leu Ile Asn Arg Arg Lys Lys Val Lys Val Leu Arg
465                 470                 475                 480

Glu Lys Ala Glu Lys Gly Glu Phe Asp Glu Glu Xaa Gln Xaa Leu Asp
                485                 490                 495

Tyr Glu Gln Arg Leu Ile Lys Val Leu Ala Asn Ser His Tyr Gly Tyr
            500                 505                 510

Leu Ala Phe Pro Met Ala Arg Trp Tyr Ser Arg Asp Cys Ala Glu Ile
        515                 520                 525

Thr Thr His Leu Gly Arg Gln Tyr Ile Gln Lys Thr Ile Glu Glu Ala
    530                 535                 540

Glu Asn Phe Gly Phe Lys Val Ile Tyr Ala Asp Thr Asp Gly Phe Tyr
545                 550                 555                 560

Ser Lys Trp Ala Asp Asp Lys Glu Lys Leu Ser Lys Tyr Glu Leu Leu
                565                 570                 575

Glu Lys Thr Arg Glu Phe Leu Lys Asn Ile Asn Asn Thr Leu Pro Gly
            580                 585                 590

Glu Met Glu Leu Glu Phe Glu Gly Tyr Phe Lys Arg Gly Ile Phe Val
        595                 600                 605

Xaa Lys Lys Lys Tyr Ala Leu Ile Asp Glu Asn Glu Lys Ile Thr Val
    610                 615                 620

Lys Gly Leu Glu Val Val Arg Arg Asp Trp Ser Asn Val Ser Lys Asn
625                 630                 635                 640

Thr Gln Lys Asn Val Leu Asn Ala Leu Leu Lys Glu Gly Ser Val Glu
                645                 650                 655

Asn Xaa Lys Lys Val Ile Gln Asp Thr Ile Lys Glu Leu Lys Asp Gly
            660                 665                 670

Lys Val Asn Asn Glu Asp Leu Leu Ile His Thr Gln Leu Thr Lys Arg
        675                 680                 685

Ile Glu Asp Tyr Lys Thr Thr Ala Pro His Val Glu Val Ala Lys Lys
    690                 695                 700

Ile Leu Lys Ser Gly Asn Arg Val Asn Thr Gly Asp Val Ile Ser Tyr
705                 710                 715                 720

Ile Ile Thr Ser Gly Asn Lys Ser Ile Ser Glu Arg Ala Glu Ile Leu
                725                 730                 735

Glu Asn Ala Lys Asn Tyr Asp Thr Asn Tyr Tyr Ile Glu Asn Gln Ile
            740                 745                 750

Leu Pro Pro Val Ile Arg Leu Met Glu Ala Leu Gly Ile Thr Lys Asp
        755                 760                 765

Glu Leu Lys Asp Ser Lys Lys Gln Tyr Thr Leu His His Phe Leu Lys
    770                 775                 780

<210> SEQ ID NO 26
<211> LENGTH: 784
<212> TYPE: PRT
<213> ORGANISM: Methanococcus maripaludis
<220> FEATURE:
```

```
<221> NAME/KEY: Variant
<222> LOCATION: (156)..(156)
<223> OTHER INFORMATION: X= V, A
<220> FEATURE:
<221> NAME/KEY: Variant
<222> LOCATION: (165)..(165)
<223> OTHER INFORMATION: X= K, D
<220> FEATURE:
<221> NAME/KEY: Variant
<222> LOCATION: (417)..(417)
<223> OTHER INFORMATION: X= L, A
<220> FEATURE:
<221> NAME/KEY: Variant
<222> LOCATION: (418)..(418)
<223> OTHER INFORMATION: X= Y, A
<220> FEATURE:
<221> NAME/KEY: Variant
<222> LOCATION: (419)..(419)
<223> OTHER INFORMATION: X= P, V, A, I
<220> FEATURE:
<221> NAME/KEY: Variant
<222> LOCATION: (492)..(492)
<223> OTHER INFORMATION: X= Y, W
<220> FEATURE:
<221> NAME/KEY: Variant
<222> LOCATION: (494)..(494)
<223> OTHER INFORMATION: X= I, S
<220> FEATURE:
<221> NAME/KEY: Variant
<222> LOCATION: (609)..(609)
<223> OTHER INFORMATION: X= T, I
<220> FEATURE:
<221> NAME/KEY: Variant
<222> LOCATION: (658)..(658)
<223> OTHER INFORMATION: X= A, V, F

<400> SEQUENCE: 26

Met Glu Ser Leu Ile Asp Leu Asp Tyr Asn Ser Asp Leu Cys Ile
1               5                   10                  15

Tyr Leu Tyr Leu Ile Asn Ser Ile Ile Lys Glu Lys Asp Phe Lys Pro
            20                  25                  30

Tyr Phe Tyr Val Asn Ser Thr Asp Lys Glu Gln Ile Leu Glu Phe Leu
        35                  40                  45

Lys Asp Tyr Glu Lys Lys His Lys Leu Asp Ser Glu Ile Ser Lys Met
50                  55                  60

Ile Glu Asn Ile Glu Thr Val Lys Lys Ile Val Phe Asp Glu Asn Tyr
65                  70                  75                  80

Gln Glu Lys Glu Leu Ser Lys Val Thr Val Lys Tyr Pro Asn Asn Val
                85                  90                  95

Lys Thr Val Arg Glu Ile Leu Met Glu Phe Glu Arg Leu Tyr Glu Tyr
            100                 105                 110

Asp Ile Pro Phe Val Arg Arg Tyr Leu Ile Asp Asn Ser Val Ile Pro
        115                 120                 125

Thr Ser Thr Trp Asp Phe Glu Asn Asn Lys Lys Ile Asp Asn Lys Ile
130                 135                 140

Pro Asp Phe Lys Thr Val Ser Phe Ala Ile Ala Xaa Tyr Cys Asn Lys
145                 150                 155                 160

Glu Pro Asn Pro Xaa Lys Asp Pro Ile Ile Met Ala Ser Phe Ser Ser
                165                 170                 175

Lys Asp Phe Asn Thr Val Val Ser Thr Lys Lys Phe Asp His Glu Lys
            180                 185                 190

Leu Glu Tyr Val Lys Asp Glu Lys Glu Leu Ile Lys Arg Ile Ile Glu
        195                 200                 205

Ile Leu Lys Glu Tyr Asp Ile Ile Tyr Thr Tyr Asn Gly Asp Asn Phe
210                 215                 220
```

```
Asp Phe Pro Tyr Leu Lys Lys Arg Ala Glu Ser Phe Gly Leu Glu Leu
225                 230                 235                 240

Lys Leu Gly Lys Asn Asp Glu Lys Ile Lys Ile Thr Lys Gly Gly Met
                245                 250                 255

Asn Ser Lys Ser Tyr Ile Pro Gly Arg Val His Ile Asp Leu Tyr Pro
            260                 265                 270

Ile Ala Arg Arg Leu Leu Asn Leu Thr Lys Tyr Arg Leu Glu Asn Val
        275                 280                 285

Thr Glu Ala Leu Phe Asp Val Lys Lys Val Asp Val Gly His Glu Asn
290                 295                 300

Ile Pro Lys Met Trp Asp Asn Leu Asp Glu Thr Leu Val Glu Tyr Ser
305                 310                 315                 320

His Gln Asp Ala Tyr Tyr Thr Gln Arg Ile Gly Glu Gln Phe Leu Pro
            325                 330                 335

Leu Glu Ile Met Phe Ser Arg Val Val Asn Gln Ser Leu Tyr Asp Ile
            340                 345                 350

Asn Arg Met Ser Ser Ser Gln Met Val Glu Tyr Leu Leu Leu Lys Asn
        355                 360                 365

Ser Tyr Lys Met Gly Val Ile Ala Pro Asn Arg Pro Ser Gly Lys Glu
370                 375                 380

Tyr Gln Lys Arg Ile Arg Ser Ser Tyr Glu Gly Gly Tyr Val Lys Glu
385                 390                 395                 400

Pro Leu Lys Gly Ile His Glu Asp Ile Val Ser Met Asp Phe Leu Ser
            405                 410                 415

Xaa Xaa Xaa Ser Ile Ile Met Ser His Asn Leu Ser Pro Glu Thr Ile
            420                 425                 430

Asp Cys Thr Cys Cys Ser Asp Glu Glu Asn Gly Glu Asn Gly Glu Ile
            435                 440                 445

Leu Gly His Lys Phe Cys Lys Lys Ser Ile Gly Ile Ile Pro Lys Thr
450                 455                 460

Leu Met Asp Leu Ile Asn Arg Arg Lys Lys Val Lys Lys Val Leu Arg
465                 470                 475                 480

Glu Lys Ala Glu Lys Gly Glu Phe Asp Glu Xaa Gln Xaa Leu Asp
                485                 490                 495

Tyr Glu Gln Arg Leu Ile Lys Val Leu Ala Asn Ser His Tyr Gly Tyr
            500                 505                 510

Leu Ala Phe Pro Met Ala Arg Trp Tyr Ser Arg Asp Cys Ala Glu Ile
            515                 520                 525

Thr Thr His Leu Gly Arg Gln Tyr Ile Gln Lys Thr Ile Glu Glu Ala
            530                 535                 540

Glu Asn Phe Gly Phe Lys Val Ile Tyr Ala Asp Thr Asp Gly Phe Tyr
545                 550                 555                 560

Ser Lys Trp Ala Asp Asp Lys Glu Lys Leu Ser Lys Tyr Glu Leu Leu
                565                 570                 575

Glu Lys Thr Arg Glu Phe Leu Lys Asn Ile Asn Asn Thr Leu Pro Gly
            580                 585                 590

Glu Met Glu Leu Glu Phe Glu Gly Tyr Phe Lys Arg Gly Ile Phe Val
            595                 600                 605

Xaa Lys Lys Lys Tyr Ala Leu Ile Asp Glu Asn Glu Lys Ile Thr Val
            610                 615                 620

Lys Gly Leu Glu Val Val Arg Arg Asp Trp Ser Asn Val Ser Lys Asn
625                 630                 635                 640
```

```
Thr Gln Lys Asn Val Leu Asn Ala Leu Leu Lys Glu Gly Ser Val Glu
                645                 650                 655

Asn Xaa Lys Lys Val Ile Gln Asp Thr Ile Lys Glu Leu Lys Asp Gly
        660                 665                 670

Lys Val Asn Asn Glu Asp Leu Leu Ile His Thr Gln Leu Thr Lys Arg
            675                 680                 685

Ile Glu Asp Tyr Lys Thr Thr Ala Pro His Val Glu Val Ala Lys Lys
        690                 695                 700

Ile Leu Lys Ser Gly Asn Arg Val Asn Thr Gly Asp Val Ile Ser Tyr
705                 710                 715                 720

Ile Ile Thr Ser Gly Asn Lys Ser Ile Ser Glu Arg Ala Glu Ile Leu
                725                 730                 735

Glu Asn Ala Lys Asn Tyr Asp Thr Asn Tyr Tyr Ile Glu Asn Gln Ile
            740                 745                 750

Leu Pro Pro Val Ile Arg Leu Met Glu Ala Leu Gly Ile Thr Lys Asp
        755                 760                 765

Glu Leu Lys Asp Ser Lys Lys Gln Tyr Thr Leu His His Phe Leu Lys
        770                 775                 780

<210> SEQ ID NO 27
<211> LENGTH: 775
<212> TYPE: PRT
<213> ORGANISM: Thermococcus sp. 9N-7

<400> SEQUENCE: 27

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
        50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240
```

-continued

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
            290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Arg Gly Gly Tyr
            370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
            405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
            485                 490                 495

Tyr Gly Tyr Ala Lys Ala Arg Trp Tyr Cys Lys Glu Cys Ala Glu Ser
            500                 505                 510

Val Ser Ala Trp Gly Arg Glu Tyr Leu Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
            565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
            610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
            645                 650                 655

```
Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775

<210> SEQ ID NO 28
<211> LENGTH: 775
<212> TYPE: PRT
<213> ORGANISM: Thermococcus sp. 9N-7
<220> FEATURE:
<221> NAME/KEY: Variant
<222> LOCATION: (144)..(144)
<223> OTHER INFORMATION: X=T, A
<220> FEATURE:
<221> NAME/KEY: Variant
<222> LOCATION: (153)..(153)
<223> OTHER INFORMATION: X= G, D
<220> FEATURE:
<221> NAME/KEY: Variant
<222> LOCATION: (476)..(476)
<223> OTHER INFORMATION: X= K, W
<220> FEATURE:
<221> NAME/KEY: Variant
<222> LOCATION: (478)..(478)
<223> OTHER INFORMATION: X= L, S
<220> FEATURE:
<221> NAME/KEY: Variant
<222> LOCATION: (590)..(590)
<223> OTHER INFORMATION: X= T, I
<220> FEATURE:
<221> NAME/KEY: Variant
<222> LOCATION: (639)..(639)
<223> OTHER INFORMATION: X= A, V, F
<220> FEATURE:
<221> NAME/KEY: Variant
<222> LOCATION: (718)..(718)
<223> OTHER INFORMATION: X= D, N

<400> SEQUENCE: 28

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
```

```
                100                 105                 110
Asp Ile Pro Phe Ala Lys Arg Tyr Leu Ile Asp Lys Gly Leu Ile Pro
            115                 120                 125

Ala Glu Gly Asp Glu Glu Leu Thr Met Leu Ala Phe Ala Ile Ala Xaa
130                 135                 140

Leu Tyr His Glu Gly Glu Phe Xaa Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Xaa Lys Xaa Leu Asp
465                 470                 475                 480

Tyr Arg Gln Arg Val Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Ser Ala Trp Gly Arg Glu Tyr Leu Glu Met Val Ile Arg Glu Leu
        515                 520                 525
```

```
Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
            565                 570                 575

Leu Glu Tyr Glu Gly Phe Tyr Val Arg Gly Phe Phe Val Xaa Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
            610                 615                 620

Arg Val Leu Glu Ala Ile Leu Lys His Gly Asp Val Glu Glu Xaa Val
625                 630                 635                 640

Arg Ile Val Lys Glu Val Thr Glu Lys Leu Ser Lys Tyr Glu Val Pro
            645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Xaa Glu Phe
705                 710                 715                 720

Asp Pro Thr Lys His Arg Tyr Asp Ala Glu Tyr Tyr Ile Glu Asn Gln
            725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
            770                 775

<210> SEQ ID NO 29
<211> LENGTH: 775
<212> TYPE: PRT
<213> ORGANISM: Thermococcus sp. 9N-7

<400> SEQUENCE: 29

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
```

-continued

```
            115                 120                 125
Ala Glu Gly Asp Glu Glu Leu Thr Met Leu Ala Phe Ala Ile Ala Thr
            130                 135                 140
Leu Tyr His Glu Gly Glu Glu Phe Gly Thr Gly Pro Ile Leu Met Ile
145                 150                 155                 160
Ser Tyr Ala Asp Gly Ser Glu Ala Arg Val Ile Thr Trp Lys Lys Ile
                165                 170                 175
Asp Leu Pro Tyr Val Asp Val Val Ser Thr Glu Lys Glu Met Ile Lys
                180                 185                 190
Arg Phe Leu Arg Val Val Arg Glu Lys Asp Pro Asp Val Leu Ile Thr
                195                 200                 205
Tyr Asn Gly Asp Asn Phe Asp Phe Ala Tyr Leu Lys Lys Arg Ser Glu
                210                 215                 220
Glu Leu Gly Ile Lys Phe Thr Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
                260                 265                 270
Tyr Thr Leu Glu Ala Val Tyr Glu Ala Val Phe Gly Lys Pro Lys Glu
                275                 280                 285
Lys Val Tyr Ala Glu Glu Ile Ala Gln Ala Trp Glu Ser Gly Glu Gly
290                 295                 300
Leu Glu Arg Val Ala Arg Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                325                 330                 335
Ile Gly Gln Ser Leu Trp Asp Val Ser Arg Ser Ser Thr Gly Asn Leu
                340                 345                 350
Val Glu Trp Phe Leu Leu Arg Lys Ala Tyr Lys Arg Asn Glu Leu Ala
                355                 360                 365
Pro Asn Lys Pro Asp Glu Arg Glu Leu Ala Arg Arg Gly Gly Tyr
                370                 375                 380
Ala Gly Gly Tyr Val Lys Glu Pro Glu Arg Gly Leu Trp Asp Asn Ile
385                 390                 395                 400
Val Tyr Leu Asp Phe Arg Ser Ala Ala Ile Ser Ile Ile Thr His
                405                 410                 415
Asn Val Ser Pro Asp Thr Leu Asn Arg Glu Gly Cys Lys Glu Tyr Asp
                420                 425                 430
Val Ala Pro Glu Val Gly His Lys Phe Cys Lys Asp Phe Pro Gly Phe
                435                 440                 445
Ile Pro Ser Leu Leu Gly Asp Leu Leu Glu Glu Arg Gln Lys Ile Lys
                450                 455                 460
Arg Lys Met Lys Ala Thr Val Asp Pro Leu Glu Lys Lys Leu Leu Asp
465                 470                 475                 480
Tyr Arg Gln Arg Val Ile Lys Ile Leu Ala Asn Ser Phe Tyr Gly Tyr
                485                 490                 495
Tyr Gly Tyr Ala Lys Ala Arg Trp Tyr Cys Lys Glu Cys Ala Glu Ser
                500                 505                 510
Val Ala Ala Trp Gly Arg Glu Tyr Leu Glu Met Val Ile Arg Glu Leu
                515                 520                 525
Glu Glu Lys Phe Gly Phe Lys Val Leu Tyr Ala Asp Thr Asp Gly Leu
                530                 535                 540
```

```
His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
            565                 570                 575

Leu Glu Tyr Glu Gly Phe Tyr Val Arg Gly Phe Phe Val Thr Lys Lys
        580                 585                 590

Lys Tyr Ala Val Ile Asp Glu Glu Gly Lys Ile Thr Thr Arg Gly Leu
    595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
770                 775

<210> SEQ ID NO 30
<211> LENGTH: 775
<212> TYPE: PRT
<213> ORGANISM: Thermococcus sp. 9N-7
<220> FEATURE:
<221> NAME/KEY: Variant
<222> LOCATION: (144)..(144)
<223> OTHER INFORMATION: X= T, A
<220> FEATURE:
<221> NAME/KEY: Variant
<222> LOCATION: (153)..(153)
<223> OTHER INFORMATION: X= G, D
<220> FEATURE:
<221> NAME/KEY: Variant
<222> LOCATION: (476)..(476)
<223> OTHER INFORMATION: X= K, W
<220> FEATURE:
<221> NAME/KEY: Variant
<222> LOCATION: (478)..(478)
<223> OTHER INFORMATION: X= L, S
<220> FEATURE:
<221> NAME/KEY: Variant
<222> LOCATION: (590)..(590)
<223> OTHER INFORMATION: X= T, I
<220> FEATURE:
<221> NAME/KEY: Variant
<222> LOCATION: (639)..(639)
<223> OTHER INFORMATION: X= A, V, F
<220> FEATURE:
<221> NAME/KEY: Variant
<222> LOCATION: (718)..(718)
<223> OTHER INFORMATION: X= D, N
```

<400> SEQUENCE: 30

| | | | | | | | | | | | | | | |
|---|---|---|---|---|---|---|---|---|---|---|---|---|---|---|
|Met|Ile|Leu|Asp|Thr|Asp|Tyr|Ile|Thr|Glu|Asn|Gly|Lys|Pro|Val|Ile|
|1| | | |5| | | | |10| | | | |15| |

Arg Val Phe Lys Lys Glu Asn Gly Glu Phe Lys Ile Glu Tyr Asp Arg
                   20                   25                 30

Thr Phe Glu Pro Tyr Phe Tyr Ala Leu Leu Lys Asp Asp Ser Ala Ile
       35                  40                   45

Glu Asp Val Lys Lys Val Thr Ala Lys Arg His Gly Thr Val Val Lys
50                   55                   60

Val Lys Arg Ala Glu Lys Val Gln Lys Lys Phe Leu Gly Arg Pro Ile
65               70                 75             80

Glu Val Trp Lys Leu Tyr Phe Asn His Pro Gln Asp Val Pro Ala Ile
             85                 90                 95

Arg Asp Arg Ile Arg Ala His Pro Ala Val Val Asp Ile Tyr Glu Tyr
             100                105              110

Asp Ile Pro Phe Ala Lys Arg Tyr Leu Ile Asp Lys Gly Leu Ile Pro
       115                 120              125

Ala Glu Gly Asp Glu Glu Leu Thr Met Leu Ala Phe Ala Ile Ala Xaa
130                  135                140

Leu Tyr His Glu Gly Glu Glu Phe Xaa Thr Gly Pro Ile Leu Met Ile
145                  150                155              160

Ser Tyr Ala Asp Gly Ser Glu Ala Arg Val Ile Thr Trp Lys Lys Ile
             165                170              175

Asp Leu Pro Tyr Val Asp Val Val Ser Thr Glu Lys Glu Met Ile Lys
       180                 185              190

Arg Phe Leu Arg Val Val Arg Glu Lys Asp Pro Asp Val Leu Ile Thr
             195                200              205

Tyr Asn Gly Asp Asn Phe Asp Phe Ala Tyr Leu Lys Lys Arg Ser Glu
210                  215                220

Glu Leu Gly Ile Lys Phe Thr Leu Gly Arg Asp Gly Ser Glu Pro Lys
225                  230                235              240

Ile Gln Arg Met Gly Asp Arg Phe Ala Val Glu Val Lys Gly Arg Ile
             245                250              255

His Phe Asp Leu Tyr Pro Val Ile Arg Arg Thr Ile Asn Leu Pro Thr
       260                 265              270

Tyr Thr Leu Glu Ala Val Tyr Glu Ala Val Phe Gly Lys Pro Lys Glu
         275                280              285

Lys Val Tyr Ala Glu Glu Ile Ala Gln Ala Trp Glu Ser Gly Glu Gly
290                  295                300

Leu Glu Arg Val Ala Arg Tyr Ser Met Glu Asp Ala Lys Val Thr Tyr
305                  310                315              320

Glu Leu Gly Arg Glu Phe Phe Pro Met Glu Ala Gln Leu Ser Arg Leu
             325                330              335

Ile Gly Gln Ser Leu Trp Asp Val Ser Arg Ser Ser Thr Gly Asn Leu
             340                345              350

Val Glu Trp Phe Leu Leu Arg Lys Ala Tyr Lys Arg Asn Glu Leu Ala
         355                360              365

Pro Asn Lys Pro Asp Glu Arg Glu Leu Ala Arg Arg Gly Gly Tyr
       370                 375              380

Ala Gly Gly Tyr Val Lys Glu Pro Glu Arg Gly Leu Trp Asp Asn Ile
385                  390                395              400

Val Tyr Leu Asp Phe Arg Ser Ala Ala Ile Ser Ile Ile Ile Thr His

```
            405                 410                 415
Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Arg Lys Met Lys Ala Thr Val Asp Pro Leu Glu Xaa Lys Xaa Leu Asp
465                 470                 475                 480

Tyr Arg Gln Arg Val Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Ala Ala Trp Gly Arg Glu Tyr Leu Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Xaa Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Xaa Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Ala Xaa Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
770                 775

<210> SEQ ID NO 31
<211> LENGTH: 775
<212> TYPE: PRT
<213> ORGANISM: Thermococcus sp. 9N-7

<400> SEQUENCE: 31
```

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
            85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Ala Glu Gly Asp Glu Leu Thr Met Leu Ala Phe Ala Ile Ala Thr
    130                 135                 140

Leu Tyr His Glu Gly Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
            165                 170                 175

Asp Leu Pro Tyr Val Asp Val Ser Thr Glu Lys Glu Met Ile Lys
            180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
    275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
            405                 410                 415

Asn Val Ser Pro Asp Thr Leu Asn Arg Glu Gly Cys Lys Glu Tyr Asp

```
                420             425             430
Val Ala Pro Glu Val Gly His Lys Phe Cys Lys Asp Phe Pro Gly Phe
            435             440             445
Ile Pro Ser Leu Leu Gly Asp Leu Leu Glu Glu Arg Gln Lys Ile Lys
            450             455             460
Arg Lys Met Lys Ala Thr Val Asp Pro Leu Glu Lys Met Leu Leu Asp
465             470             475             480
Tyr Arg Gln Arg Val Ile Lys Ile Leu Ala Asn Ser Phe Tyr Gly Tyr
                485             490             495
Tyr Gly Tyr Ala Lys Ala Arg Trp Tyr Cys Lys Glu Cys Ala Glu Ser
                500             505             510
Val Ser Ala Trp Gly Arg Glu Tyr Leu Glu Met Val Ile Arg Glu Leu
                515             520             525
Glu Glu Lys Phe Gly Phe Lys Val Leu Tyr Ala Asp Thr Asp Gly Leu
                530             535             540
His Ala Thr Ile Pro Gly Ala Asp Ala Glu Thr Val Lys Lys Lys Ala
545             550             555             560
Lys Glu Phe Leu Lys Tyr Ile Asn Pro Lys Leu Pro Gly Leu Leu Glu
                565             570             575
Leu Glu Tyr Glu Gly Phe Tyr Val Arg Gly Phe Phe Val Thr Lys Lys
                580             585             590
Lys Tyr Ala Val Ile Asp Glu Glu Gly Lys Ile Thr Thr Arg Gly Leu
                595             600             605
Glu Ile Val Arg Arg Asp Trp Ser Glu Ile Ala Lys Glu Thr Gln Ala
                610             615             620
Arg Val Leu Glu Ala Ile Leu Lys His Gly Asp Val Glu Glu Ala Val
625             630             635             640
Arg Ile Val Lys Glu Val Thr Glu Lys Leu Ser Lys Tyr Glu Val Pro
                645             650             655
Pro Glu Lys Leu Val Ile His Glu Gln Ile Thr Arg Asp Leu Arg Asp
                660             665             670
Tyr Lys Ala Thr Gly Pro His Val Ala Val Ala Lys Arg Leu Ala Ala
                675             680             685
Arg Gly Val Lys Ile Arg Pro Gly Thr Val Ile Ser Tyr Ile Val Leu
                690             695             700
Lys Gly Ser Gly Arg Ile Gly Asp Arg Ala Ile Pro Ala Asp Glu Phe
705             710             715             720
Asp Pro Thr Lys His Arg Tyr Asp Ala Glu Tyr Tyr Ile Glu Asn Gln
                725             730             735
Val Leu Pro Ala Val Glu Arg Ile Leu Lys Ala Phe Gly Tyr Arg Lys
                740             745             750
Glu Asp Leu Arg Tyr Gln Lys Thr Lys Gln Val Gly Leu Gly Ala Trp
                755             760             765
Leu Lys Val Lys Gly Lys Lys
            770             775

<210> SEQ ID NO 32
<211> LENGTH: 775
<212> TYPE: PRT
<213> ORGANISM: Thermococcus sp. 9N-7
<220> FEATURE:
<221> NAME/KEY: Variant
<222> LOCATION: (144)..(144)
<223> OTHER INFORMATION: X= T, A
<220> FEATURE:
<221> NAME/KEY: Variant
```

```
<222> LOCATION: (153)..(153)
<223> OTHER INFORMATION: X= G, D
<220> FEATURE:
<221> NAME/KEY: Variant
<222> LOCATION: (476)..(476)
<223> OTHER INFORMATION: X= K, W
<220> FEATURE:
<221> NAME/KEY: Variant
<222> LOCATION: (478)..(478)
<223> OTHER INFORMATION: X= L, S
<220> FEATURE:
<221> NAME/KEY: Variant
<222> LOCATION: (590)..(590)
<223> OTHER INFORMATION: X= T, I
<220> FEATURE:
<221> NAME/KEY: Variant
<222> LOCATION: (639)..(639)
<223> OTHER INFORMATION: X= A, V, F
<220> FEATURE:
<221> NAME/KEY: Variant
<222> LOCATION: (718)..(718)
<223> OTHER INFORMATION: X= D, N

<400> SEQUENCE: 32

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Xaa
    130                 135                 140

Leu Tyr His Glu Gly Glu Glu Phe Xaa Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285
```

```
Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Xaa Met Xaa Leu Asp
465                 470                 475                 480

Tyr Arg Gln Arg Val Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Ser Ala Trp Gly Arg Glu Tyr Leu Glu Met Val Ile Arg Glu Leu
        515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Xaa Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Xaa Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Xaa Glu Phe
```

```
                705                 710                 715                 720
Asp Pro Thr Lys His Arg Tyr Asp Ala Glu Tyr Tyr Ile Glu Asn Gln
                    725                 730                 735

Val Leu Pro Ala Val Glu Arg Ile Leu Lys Ala Phe Gly Tyr Arg Lys
                    740                 745                 750

Glu Asp Leu Arg Tyr Gln Lys Thr Lys Gln Val Gly Leu Gly Ala Trp
                    755                 760                 765

Leu Lys Val Lys Gly Lys Lys
                    770                 775

<210> SEQ ID NO 33
<211> LENGTH: 775
<212> TYPE: PRT
<213> ORGANISM: Thermococcus sp. 9N-7

<400> SEQUENCE: 33

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
                35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
                100                 105                 110

Asp Ile Pro Phe Ala Lys Arg Tyr Leu Ile Asp Lys Gly Leu Ile Pro
                115                 120                 125

Ala Glu Gly Asp Glu Glu Leu Thr Met Leu Ala Phe Ala Ile Ala Ala
                130                 135                 140

Leu Tyr His Glu Gly Glu Glu Phe Asp Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
                180                 185                 190

Arg Phe Leu Arg Val Val Arg Glu Lys Asp Pro Asp Val Leu Ile Thr
                195                 200                 205

Tyr Asn Gly Asp Asn Phe Asp Phe Ala Tyr Leu Lys Lys Arg Ser Glu
                210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Lys Pro Lys Glu
                275                 280                 285

Lys Val Tyr Ala Glu Glu Ile Ala Gln Ala Trp Glu Ser Gly Glu Gly
                290                 295                 300
```

```
Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
            405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Ser Ala Trp Gly Arg Glu Tyr Leu Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Ile Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Val Val
625                 630                 635                 640

Arg Ile Val Lys Glu Val Thr Glu Lys Leu Ser Lys Tyr Glu Val Pro
            645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Ala Asn Glu Phe
705                 710                 715                 720

Asp Pro Thr Lys His Arg Tyr Asp Ala Glu Tyr Tyr Ile Glu Asn Gln
```

-continued

```
                725                 730                 735
Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
            770                 775

<210> SEQ ID NO 34
<211> LENGTH: 775
<212> TYPE: PRT
<213> ORGANISM: Thermococcus sp. 9N-7

<400> SEQUENCE: 34

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
        50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Ala
    130                 135                 140

Leu Tyr His Glu Gly Glu Glu Phe Asp Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320
```

```
Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Thr Gly Asn Leu
    340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Ile Thr His
                405                 410                 415

Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
                435                 440                 445

Ile Pro Ser Leu Leu Gly Asp Leu Leu Glu Glu Arg Gln Lys Ile Lys
                450                 455                 460

Arg Lys Met Lys Ala Thr Val Asp Pro Leu Glu Lys Met Leu Leu Asp
465                 470                 475                 480

Tyr Arg Gln Arg Val Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
                500                 505                 510

Val Ser Ala Trp Gly Arg Glu Tyr Leu Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Ile Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Val Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
                660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asn Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
```

```
            740                 745                 750
Glu Asp Leu Arg Tyr Gln Lys Thr Lys Gln Val Gly Leu Gly Ala Trp
        755                 760                 765

Leu Lys Val Lys Gly Lys Lys
        770                 775

<210> SEQ ID NO 35
<211> LENGTH: 775
<212> TYPE: PRT
<213> ORGANISM: Thermococcus sp. 9N-7

<400> SEQUENCE: 35

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335
```

```
Ile Gly Gln Ser Leu Trp Asp Val Ser Arg Ser Ser Thr Gly Asn Leu
                340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
        370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Trp Met Leu Leu Asp
465                 470                 475                 480

Tyr Arg Gln Arg Val Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Ser Ala Trp Gly Arg Glu Tyr Leu Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
```

```
              755                 760                 765
Leu Lys Val Lys Gly Lys Lys
    770                 775

<210> SEQ ID NO 36
<211> LENGTH: 775
<212> TYPE: PRT
<213> ORGANISM: Thermococcus sp. 9N-7

<400> SEQUENCE: 36

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350
```

Val Glu Trp Phe Leu Leu Arg Lys Ala Tyr Lys Arg Asn Glu Leu Ala
355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
            405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Met Ser Leu Asp
465                 470                 475                 480

Tyr Arg Gln Arg Val Ile Lys Ile Leu Ala Asn Ser Phe Tyr Gly Tyr
            485                 490                 495

Tyr Gly Tyr Ala Lys Ala Arg Trp Tyr Cys Lys Glu Cys Ala Glu Ser
            500                 505                 510

Val Ser Ala Trp Gly Arg Glu Tyr Leu Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
            565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
            645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
            725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys

```
            770                 775

<210> SEQ ID NO 37
<211> LENGTH: 775
<212> TYPE: PRT
<213> ORGANISM: Thermococcus sp. 9N-7

<400> SEQUENCE: 37

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365
```

```
Pro Asn Lys Pro Asp Glu Arg Glu Leu Ala Arg Arg Gly Gly Tyr
    370             375                 380
Ala Gly Gly Tyr Val Lys Glu Pro Glu Arg Gly Leu Trp Asp Asn Ile
385                 390                 395                 400
Val Tyr Leu Asp Phe Arg Ser Ala Ala Ile Ser Ile Ile Thr His
                405                 410                 415
Asn Val Ser Pro Asp Thr Leu Asn Arg Glu Gly Cys Lys Glu Tyr Asp
                420                 425                 430
Val Ala Pro Glu Val Gly His Lys Phe Cys Lys Asp Phe Pro Gly Phe
            435                 440                 445
Ile Pro Ser Leu Leu Gly Asp Leu Leu Glu Glu Arg Gln Lys Ile Lys
450                 455                 460
Arg Lys Met Lys Ala Thr Val Asp Pro Leu Glu Trp Met Ser Leu Asp
465                 470                 475                 480
Tyr Arg Gln Arg Val Ile Lys Ile Leu Ala Asn Ser Phe Tyr Gly Tyr
                485                 490                 495
Tyr Gly Tyr Ala Lys Ala Arg Trp Tyr Cys Lys Glu Cys Ala Glu Ser
                500                 505                 510
Val Ser Ala Trp Gly Arg Glu Tyr Leu Glu Met Val Ile Arg Glu Leu
            515                 520                 525
Glu Glu Lys Phe Gly Phe Lys Val Leu Tyr Ala Asp Thr Asp Gly Leu
530                 535                 540
His Ala Thr Ile Pro Gly Ala Asp Ala Glu Thr Val Lys Lys Lys Ala
545                 550                 555                 560
Lys Glu Phe Leu Lys Tyr Ile Asn Pro Lys Leu Pro Gly Leu Leu Glu
                565                 570                 575
Leu Glu Tyr Glu Gly Phe Tyr Val Arg Gly Phe Phe Val Ile Lys Lys
                580                 585                 590
Lys Tyr Ala Val Ile Asp Glu Glu Gly Lys Ile Thr Thr Arg Gly Leu
            595                 600                 605
Glu Ile Val Arg Arg Asp Trp Ser Glu Ile Ala Lys Glu Thr Gln Ala
610                 615                 620
Arg Val Leu Glu Ala Ile Leu Lys His Gly Asp Val Glu Glu Phe Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Arg Asp
                660                 665                 670
Tyr Lys Ala Thr Gly Pro His Val Ala Val Ala Lys Arg Leu Ala Ala
            675                 680                 685
Arg Gly Val Lys Ile Arg Pro Gly Thr Val Ile Ser Tyr Ile Val Leu
690                 695                 700
Lys Gly Ser Gly Arg Ile Gly Asp Arg Ala Ile Pro Ala Asp Glu Phe
705                 710                 715                 720
Asp Pro Thr Lys His Arg Tyr Asp Ala Glu Tyr Tyr Ile Glu Asn Gln
                725                 730                 735
Val Leu Pro Ala Val Glu Arg Ile Leu Lys Ala Phe Gly Tyr Arg Lys
                740                 745                 750
Glu Asp Leu Arg Tyr Gln Lys Thr Lys Gln Val Gly Leu Gly Ala Trp
            755                 760                 765
Leu Lys Val Lys Gly Lys Lys
770                 775
```

```
<210> SEQ ID NO 38
<211> LENGTH: 775
<212> TYPE: PRT
<213> ORGANISM: Thermococcus sp. 9N-7

<400> SEQUENCE: 38

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380
```

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Ile Thr His
            405                 410                 415

Asn Val Ser Pro Asp Thr Leu Asn Arg Glu Gly Cys Lys Glu Tyr Asp
        420                 425                 430

Val Ala Pro Glu Val Gly His Lys Phe Cys Lys Asp Phe Pro Gly Phe
    435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Trp Met Leu Leu Asp
465                 470                 475                 480

Tyr Arg Gln Arg Val Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Ser Ala Trp Gly Arg Glu Tyr Leu Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Ile Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
770                 775

<210> SEQ ID NO 39
<211> LENGTH: 775
<212> TYPE: PRT

<213> ORGANISM: Thermococcus sp. 9N-7

<400> SEQUENCE: 39

```
Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400
```

Val Tyr Leu Asp Phe Arg Ser Ala Ala Ile Ser Ile Ile Thr His
            405                 410                 415

Asn Val Ser Pro Asp Thr Leu Asn Arg Glu Gly Cys Lys Glu Tyr Asp
        420                 425                 430

Val Ala Pro Glu Val Gly His Lys Phe Cys Lys Asp Phe Pro Gly Phe
    435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Met Leu Leu Asp
465                 470                 475                 480

Tyr Arg Gln Arg Val Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Ser Ala Trp Gly Arg Glu Tyr Leu Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Ile Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775

<210> SEQ ID NO 40
<211> LENGTH: 775
<212> TYPE: PRT
<213> ORGANISM: Thermococcus sp. 9N-7

<400> SEQUENCE: 40

-continued

```
Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Ser Thr Glu Lys Glu Met Ile Lys
            180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
        370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Ile Thr His
                405                 410                 415
```

-continued

```
Asn Val Ser Pro Asp Thr Leu Asn Arg Glu Gly Cys Lys Glu Tyr Asp
            420                 425                 430
Val Ala Pro Glu Val Gly His Lys Phe Cys Lys Asp Phe Pro Gly Phe
        435                 440                 445
Ile Pro Ser Leu Leu Gly Asp Leu Leu Glu Glu Arg Gln Lys Ile Lys
    450                 455                 460
Arg Lys Met Lys Ala Thr Val Asp Pro Leu Glu Trp Met Ser Leu Asp
465                 470                 475                 480
Tyr Arg Gln Arg Val Ile Lys Ile Leu Ala Asn Ser Phe Tyr Gly Tyr
                485                 490                 495
Tyr Gly Tyr Ala Lys Ala Arg Trp Tyr Cys Lys Glu Cys Ala Glu Ser
            500                 505                 510
Val Ser Ala Trp Gly Arg Glu Tyr Leu Glu Met Val Ile Arg Glu Leu
        515                 520                 525
Glu Glu Lys Phe Gly Phe Lys Val Leu Tyr Ala Asp Thr Asp Gly Leu
    530                 535                 540
His Ala Thr Ile Pro Gly Ala Asp Ala Glu Thr Val Lys Lys Lys Ala
545                 550                 555                 560
Lys Glu Phe Leu Lys Tyr Ile Asn Pro Lys Leu Pro Gly Leu Leu Glu
                565                 570                 575
Leu Glu Tyr Glu Gly Phe Tyr Val Arg Gly Phe Phe Val Thr Lys Lys
            580                 585                 590
Lys Tyr Ala Val Ile Asp Glu Glu Gly Lys Ile Thr Thr Arg Gly Leu
        595                 600                 605
Glu Ile Val Arg Arg Asp Trp Ser Glu Ile Ala Lys Glu Thr Gln Ala
    610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Arg Asp
            660                 665                 670
Tyr Lys Ala Thr Gly Pro His Val Ala Val Ala Lys Arg Leu Ala Ala
        675                 680                 685
Arg Gly Val Lys Ile Arg Pro Gly Thr Val Ile Ser Tyr Ile Val Leu
    690                 695                 700
Lys Gly Ser Gly Arg Ile Gly Asp Arg Ala Ile Pro Ala Asp Glu Phe
705                 710                 715                 720
Asp Pro Thr Lys His Arg Tyr Asp Ala Glu Tyr Tyr Ile Glu Asn Gln
                725                 730                 735
Val Leu Pro Ala Val Glu Arg Ile Leu Lys Ala Phe Gly Tyr Arg Lys
            740                 745                 750
Glu Asp Leu Arg Tyr Gln Lys Thr Lys Gln Val Gly Leu Gly Ala Trp
        755                 760                 765
Leu Lys Val Lys Gly Lys Lys
    770                 775
```

<210> SEQ ID NO 41
<211> LENGTH: 903
<212> TYPE: PRT
<213> ORGANISM: Enterobacteria phage RB69

<400> SEQUENCE: 41

```
Met Lys Glu Phe Tyr Leu Thr Val Glu Gln Ile Gly Asp Ser Ile Phe
1               5                   10                  15
```

```
Glu Arg Tyr Ile Asp Ser Asn Gly Arg Glu Arg Thr Arg Glu Val Glu
            20                  25                  30

Tyr Lys Pro Ser Leu Phe Ala His Cys Pro Glu Ser Gln Ala Thr Lys
        35                  40                  45

Tyr Phe Asp Ile Tyr Gly Lys Pro Cys Thr Arg Lys Leu Phe Ala Asn
    50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
        115                 120                 125

Ala Lys His Pro Ile Asp Ala Ile Thr His Tyr Asp Ser Ile Asp Asp
    130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
        195                 200                 205

Thr Pro Val Ile Leu Thr Gly Trp Asn Val Glu Ser Phe Asp Ile Pro
    210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                245                 250                 255

Tyr Gly Ser Arg Glu Ile Ile Thr Leu Phe Gly Ile Ser Val Leu Asp
            260                 265                 270

Tyr Ile Asp Leu Tyr Lys Lys Phe Ser Phe Thr Asn Gln Pro Ser Tyr
        275                 280                 285

Ser Leu Asp Tyr Ile Ser Glu Phe Glu Leu Asn Val Gly Lys Leu Lys
    290                 295                 300

Tyr Asp Gly Pro Ile Ser Lys Leu Arg Glu Ser Asn His Gln Arg Tyr
305                 310                 315                 320

Ile Ser Tyr Asn Ile Ile Asp Val Tyr Arg Val Leu Gln Ile Asp Ala
                325                 330                 335

Lys Arg Gln Phe Ile Asn Leu Ser Leu Asp Met Gly Tyr Tyr Ala Lys
            340                 345                 350

Ile Gln Ile Gln Ser Val Phe Ser Pro Ile Lys Thr Trp Asp Ala Ile
        355                 360                 365

Ile Phe Asn Ser Leu Lys Glu Gln Asn Lys Val Ile Pro Gln Gly Arg
    370                 375                 380

Ser His Pro Val Gln Pro Tyr Pro Gly Ala Phe Val Lys Glu Pro Ile
385                 390                 395                 400

Pro Asn Arg Tyr Lys Tyr Val Met Ser Phe Asp Leu Thr Ser Leu Tyr
                405                 410                 415

Pro Ser Ile Ile Arg Gln Val Asn Ile Ser Pro Glu Thr Ile Ala Gly
            420                 425                 430
```

```
Thr Phe Lys Val Ala Pro Leu His Asp Tyr Ile Asn Ala Val Ala Glu
            435                 440                 445

Arg Pro Ser Asp Val Tyr Ser Cys Ser Pro Asn Gly Met Met Tyr Tyr
        450                 455                 460

Lys Asp Arg Asp Gly Val Val Pro Thr Glu Ile Thr Lys Val Phe Asn
465                 470                 475                 480

Gln Arg Lys Glu His Lys Gly Tyr Met Leu Ala Ala Gln Arg Asn Gly
                485                 490                 495

Glu Ile Ile Lys Glu Ala Leu His Asn Pro Asn Leu Ser Val Asp Glu
            500                 505                 510

Pro Leu Asp Val Asp Tyr Arg Phe Asp Phe Ser Asp Glu Ile Lys Glu
        515                 520                 525

Lys Ile Lys Lys Leu Ser Ala Lys Ser Leu Asn Glu Met Leu Phe Arg
530                 535                 540

Ala Gln Arg Thr Glu Val Ala Gly Met Thr Ala Gln Ile Asn Arg Lys
545                 550                 555                 560

Leu Leu Ile Asn Ser Leu Tyr Gly Ala Leu Gly Asn Val Trp Phe Arg
                565                 570                 575

Tyr Tyr Asp Leu Arg Asn Ala Thr Ala Ile Thr Thr Phe Gly Gln Met
            580                 585                 590

Ala Leu Gln Trp Ile Glu Arg Lys Val Asn Glu Tyr Leu Asn Glu Val
        595                 600                 605

Cys Gly Thr Glu Gly Glu Ala Phe Val Leu Tyr Gly Asp Thr Asp Ser
        610                 615                 620

Ile Tyr Val Ser Ala Asp Lys Ile Ile Asp Lys Val Gly Glu Ser Lys
625                 630                 635                 640

Phe Arg Asp Thr Asn His Trp Val Asp Phe Leu Asp Lys Phe Ala Arg
                645                 650                 655

Glu Arg Met Glu Pro Ala Ile Asp Arg Gly Phe Arg Glu Met Cys Glu
            660                 665                 670

Tyr Met Asn Asn Lys Gln His Leu Met Phe Met Asp Arg Glu Ala Ile
        675                 680                 685

Ala Gly Pro Pro Leu Gly Ser Lys Gly Ile Gly Gly Phe Trp Thr Gly
        690                 695                 700

Lys Lys Arg Tyr Ala Leu Asn Val Trp Asp Met Glu Gly Thr Arg Tyr
705                 710                 715                 720

Ala Glu Pro Lys Leu Lys Ile Met Gly Leu Glu Thr Gln Lys Ser Ser
                725                 730                 735

Thr Pro Lys Ala Val Gln Lys Ala Leu Lys Glu Cys Ile Arg Arg Met
            740                 745                 750

Leu Gln Glu Gly Glu Glu Ser Leu Gln Glu Tyr Phe Lys Glu Phe Glu
        755                 760                 765

Lys Glu Phe Arg Gln Leu Asn Tyr Ile Ser Ile Ala Ser Val Ser Ser
770                 775                 780

Ala Asn Asn Ile Ala Lys Tyr Asp Val Gly Gly Phe Pro Gly Pro Lys
785                 790                 795                 800

Cys Pro Phe His Ile Arg Gly Ile Leu Thr Tyr Asn Arg Ala Ile Lys
                805                 810                 815

Gly Asn Ile Asp Ala Pro Gln Val Glu Gly Glu Lys Val Tyr Val
            820                 825                 830

Leu Pro Leu Arg Glu Gly Asn Pro Phe Gly Asp Lys Cys Ile Ala Trp
        835                 840                 845

Pro Ser Gly Thr Glu Ile Thr Asp Leu Ile Lys Asp Asp Val Leu His
```

```
                850                 855                 860
Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Lys Ala Ser
                    885                 890                 895

Leu Phe Asp Met Phe Asp Phe
            900

<210> SEQ ID NO 42
<211> LENGTH: 773
<212> TYPE: PRT
<213> ORGANISM: Thermococcus gorgonarius

<400> SEQUENCE: 42

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
                20                  25                  30

Asn Phe Glu Pro Tyr Ile Tyr Ala Leu Leu Lys Asp Asp Ser Ala Ile
            35                  40                  45

Glu Asp Val Lys Lys Ile Thr Ala Glu Arg His Gly Thr Thr Val Arg
50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
290                 295                 300

Leu Glu Arg Val Ala Arg Tyr Ser Met Glu Asp Ala Lys Val Thr Tyr
305                 310                 315                 320
```

```
Glu Leu Gly Lys Glu Phe Pro Met Glu Ala Gln Leu Ser Arg Leu
                325                 330                 335

Val Gly Gln Ser Leu Trp Asp Val Ser Arg Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
```

```
                          740                 745                 750
Glu Asp Leu Arg Tyr Gln Lys Thr Arg Gln Val Gly Leu Gly Ala Trp
            755                 760                 765
Leu Lys Pro Lys Thr
        770

<210> SEQ ID NO 43
<211> LENGTH: 775
<212> TYPE: PRT
<213> ORGANISM: artificial
<220> FEATURE:
<223> OTHER INFORMATION: 9N polymerase T514S/I521L mutant

<400> SEQUENCE: 43

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
```

```
              325                 330                 335
Ile Gly Gln Ser Leu Trp Asp Val Ser Arg Ser Thr Gly Asn Leu
            340                 345                 350
Val Glu Trp Phe Leu Leu Arg Lys Ala Tyr Lys Arg Asn Glu Leu Ala
            355                 360                 365
Pro Asn Lys Pro Asp Glu Arg Glu Leu Ala Arg Arg Gly Gly Tyr
            370                 375                 380
Ala Gly Gly Tyr Val Lys Glu Pro Arg Gly Leu Trp Asp Asn Ile
385                 390                 395                 400
Val Tyr Leu Asp Phe Arg Ser Leu Tyr Pro Ser Ile Ile Thr His
                    405                 410                 415
Asn Val Ser Pro Asp Thr Leu Asn Arg Glu Gly Cys Lys Glu Tyr Asp
                420                 425                 430
Val Ala Pro Glu Val Gly His Lys Phe Cys Lys Asp Phe Pro Gly Phe
                435                 440                 445
Ile Pro Ser Leu Leu Gly Asp Leu Leu Glu Glu Arg Gln Lys Ile Lys
            450                 455                 460
Arg Lys Met Lys Ala Thr Val Asp Pro Leu Glu Lys Lys Leu Leu Asp
465                 470                 475                 480
Tyr Arg Gln Arg Ala Ile Lys Ile Leu Ala Asn Ser Phe Tyr Gly Tyr
                    485                 490                 495
Tyr Gly Tyr Ala Lys Ala Arg Trp Tyr Cys Lys Glu Cys Ala Glu Ser
                500                 505                 510
Val Ser Ala Trp Gly Arg Glu Tyr Leu Glu Met Val Ile Arg Glu Leu
                515                 520                 525
Glu Glu Lys Phe Gly Phe Lys Val Leu Tyr Ala Asp Thr Asp Gly Leu
            530                 535                 540
His Ala Thr Ile Pro Gly Ala Asp Ala Glu Thr Val Lys Lys Lys Ala
545                 550                 555                 560
Lys Glu Phe Leu Lys Tyr Ile Asn Pro Lys Leu Pro Gly Leu Leu Glu
                    565                 570                 575
Leu Glu Tyr Glu Gly Phe Tyr Val Arg Gly Phe Phe Val Thr Lys Lys
                580                 585                 590
Lys Tyr Ala Val Ile Asp Glu Glu Gly Lys Ile Thr Thr Arg Gly Leu
                595                 600                 605
Glu Ile Val Arg Arg Asp Trp Ser Glu Ile Ala Lys Glu Thr Gln Ala
            610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                    645                 650                 655
Pro Glu Lys Leu Val Ile His Glu Gln Ile Thr Arg Asp Leu Arg Asp
                660                 665                 670
Tyr Lys Ala Thr Gly Pro His Val Ala Val Lys Arg Leu Ala Ala
                675                 680                 685
Arg Gly Val Lys Ile Arg Pro Gly Thr Val Ile Ser Tyr Ile Val Leu
            690                 695                 700
Lys Gly Ser Gly Arg Ile Gly Asp Arg Ala Ile Pro Ala Asp Glu Phe
705                 710                 715                 720
Asp Pro Thr Lys His Arg Tyr Asp Ala Glu Tyr Tyr Ile Glu Asn Gln
                    725                 730                 735
Val Leu Pro Ala Val Glu Arg Ile Leu Lys Ala Phe Gly Tyr Arg Lys
                740                 745                 750
```

```
Glu Asp Leu Arg Tyr Gln Lys Thr Lys Gln Val Gly Leu Gly Ala Trp
        755                 760                 765

Leu Lys Val Lys Gly Lys Lys
    770             775
```

MODIFIED POLYMERASES FOR IMPROVED INCORPORATION OF NUCLEOTIDE ANALOGUES

BACKGROUND

DNA polymerases are relied upon by all organisms to replicate and maintain their genomes. They allow high fidelity replication of DNA by detecting complementarity between bases as well as recognizing additional structural features of the base. There remains a need for modified polymerases with improved incorporation of nucleotide analogues, in particular nucleotides which are modified at the 3' sugar hydroxyl.

SEQUENCE LISTING

The present application is being filed along with a Sequence Listing in electronic format. The Sequence Listing is provided as a file entitled SequenceListingUpdated.txt created Oct. 21, 2016, which is 234 Kb in size. The information in the electronic format of the Sequence Listing is incorporated herein by reference in its entirety.

BRIEF SUMMARY

Presented herein are polymerase enzymes for improved incorporation of nucleotide analogues, in particular nucleotides which are modified at the 3' sugar hydroxyl such that the substituent is larger in size than the naturally occurring 3' hydroxyl group. The present inventors have surprisingly identified certain altered polymerases which exhibit improved incorporation of the desired analogues and have a number of other associated advantages.

In certain embodiments, the altered polymerase an amino acid sequence that is at least 60%, 70%, 80%, 90%, 95%, 99% identical to SEQ ID NO: 10, which recombinant DNA polymerase comprises at least one amino acid substitution mutation at one or more positions functionally equivalent to Thr144, Gly153, Lys476, Leu478, Thr590, Ala639 or Asp718 in the 9° N DNA polymerase amino acid sequence. The wild type 9° N DNA polymerase amino acid sequence is set forth in SEQ ID NO: 10.

In certain embodiments, the substitution mutation at position Thr144 comprises a mutation to a nonpolar amino acid, for example, a mutation homologous to Thr144Ala, Thr144Gly, or Thr144Leu. In certain embodiments, the substitution mutation at position Gly153 comprises a mutation to a polar amino acid for example, a mutation homologous to Gly153Asp. In certain embodiments, the substitution mutation at position Lys476 comprises a mutation to a hydrophobic amino acid, for example, a mutation homologous to Lys476Trp. In certain embodiments, the substitution mutation at position Leu478 comprises a mutation to a polar amino acid, for example, a mutation homologous to Leu478Ser, Leu478Arg, or Leu478Thr. In certain embodiments, the substitution mutation at position Thr590 comprises a mutation to a non-polar amino acid, for example, a mutation homologous to Thr590Ile, or Thr590Gly. In certain embodiments, the substitution mutation at position Ala639 comprises, for example, a mutation homologous to Ala639Val, or Ala639Phe. In certain embodiments, the substitution mutation at position Asp718 comprises a mutation to an uncharged amino acid, for example, a mutation homologous to Asp718Asn.

In some embodiments, the polymerase is a DNA polymerase. For example, the DNA polymerase can be a family B type DNA polymerase. The polymerase can be, for example, a family B archael DNA polymerase, human DNA polymerase-α, T4, RB69, and phi29 phage DNA polymerases. In certain embodiments, the family B archael DNA polymerase is from a genus selected from the group consisting of *Thermococcus, Pyrococcus*, and *Methanococcus*. For example, the polymerase can be selected from the group consisting of Vent, Deep Vent, 9° N, and Pfu polymerase. In certain embodiments, the family B archael DNA polymerase is 9° N polymerase.

In some embodiments, in addition to the above mutations, the altered polymerase can further comprise substitution mutations at positions functionally equivalent to Leu408 and/or Tyr409 and/or Pro410 in the 9° N DNA polymerase amino acid sequence. For example, the substitution mutations can comprise substitution mutations homologous to Leu408Ala and/or Tyr409Ala and/or Pro410Ile in the 9° N DNA polymerase amino acid sequence.

In some embodiments, the altered polymerase comprises reduced exonuclease activity as compared to a wild type polymerase. For example, in certain embodiments, the altered polymerase comprises substitution mutations at positions functionally equivalent to Asp141 and/or Glu143 in the 9° N DNA polymerase amino acid sequence.

In certain embodiments, the altered polymerase further comprises substitution mutations at positions functionally equivalent to Ala485 in the 9° N DNA polymerase amino acid sequence. For example, in some embodiments, the polymerase comprises a substitution mutation functionally equivalent to Ala485Leu or Ala485Val in the 9° N polymerase amino acid sequence.

In certain embodiments, the altered polymerase further comprises a substitution mutation to a different amino acid at the position functionally equivalent to Cys223 in the 9° N DNA polymerase amino acid sequence. For example, in certain embodiments, the altered polymerase comprises a substitution mutation functionally equivalent to Cys223Ser in the 9° N polymerase amino acid sequence.

In certain embodiments, the at least one substitution mutation comprises a mutation to the position equivalent to Thr514, Lys477 and/or Ile521. For example, in certain embodiments, the altered polymerase comprises a substitution mutation functionally equivalent to Thr514Ala, Thr514Ser, Lys477Met and/or Ile521Leu in the 9° N polymerase amino acid sequence.

In certain embodiments, the altered polymerase can comprise an additional substitution mutation to remove an internal methionine. For example, in some embodiments, the altered polymerase comprises a substitution mutation to a different amino acid at the position functionally equivalent to Met129 in the 9° N DNA polymerase amino acid sequence. In certain embodiments, the altered polymerase comprises a substitution mutation functionally equivalent to Met129Ala in the 9° N polymerase amino acid sequence.

Also presented herein is an altered polymerase comprising a substitution mutation to the semi-conserved domain comprising the amino acid sequence of SEQ ID NO: 1 wherein the substitution mutation comprises a mutation selected from a substitution at position 5 to any residue other than Thr or Val. In some embodiments, the mutation comprises a substitution at position 5 to Ala, Gly or Leu.

Also presented herein is an altered polymerase comprising a substitution mutation to the semi-conserved domain comprising the amino acid sequence of SEQ ID NO: 2 wherein the substitution mutation comprises a mutation selected from a substitution at position 7 to any residue other than Gly, Ala or Lys. In some embodiments, the mutation comprises a substitution at position 7 to Asp.

Also presented herein is an altered polymerase comprising a substitution mutation to the semi-conserved domain comprising the amino acid sequence of any of SEQ ID NOs: 3-6 wherein the substitution mutation comprises a mutation selected from a substitution at position 2 to any residue other than Lys, Arg, Tyr or Glu. In some embodiments, the mutation comprises a substitution at position 2 to Trp.

Also presented herein is an altered polymerase comprising a substitution mutation to the semi-conserved domain comprising the amino acid sequence of any of SEQ ID NOs: 3-6 wherein the substitution mutation comprises a mutation selected from a substitution at position 4 to any residue other than Leu, Ile or Ala. In some embodiments, the mutation comprises a substitution at position 4 to Ser, Arg or Thr.

Also presented herein is an altered polymerase comprising a substitution mutation to the semi-conserved domain comprising the amino acid sequence of SEQ ID NO: 7 wherein the substitution mutation comprises a mutation selected from a substitution at position 6 to any residue other than Thr. In some embodiments, the mutation comprises a substitution at position 6 to Ile or Gly.

Also presented herein is an altered polymerase comprising a substitution mutation to the semi-conserved domain comprising the amino acid sequence of SEQ ID NO: 8 wherein the substitution mutation comprises a mutation selected from a substitution at position 6 to any residue other than Ala. In some embodiments, the mutation comprises a substitution at position 6 to Val or Phe.

Also presented herein is an altered polymerase comprising a substitution mutation to the semi-conserved domain comprising the amino acid sequence of SEQ ID NO: 9 wherein the substitution mutation comprises a mutation selected from a substitution at position 7 to any residue other than Asp or Glu. In some embodiments, the mutation comprises a substitution at position 7 to Asn.

In some embodiments, in addition to the above mutations, the altered polymerase can further comprise substitution mutations at positions functionally equivalent to Leu408 and/or Tyr409 and/or Pro410 in the 9° N DNA polymerase amino acid sequence. For example, the substitution mutations can comprise substitution mutations homologous to Leu408Ala and/or Tyr409Ala and/or Pro410Ile in the 9° N DNA polymerase amino acid sequence.

In some embodiments, the altered polymerase comprises reduced exonuclease activity as compared to a wild type polymerase. For example, in certain embodiments, the altered polymerase comprises substitution mutations at positions functionally equivalent to Asp141 and/or Glu143 in the 9° N DNA polymerase amino acid sequence.

In certain embodiments, the altered polymerase further comprises substitution mutations at positions functionally equivalent to Ala485 in the 9° N DNA polymerase amino acid sequence. For example, in some embodiments, the polymerase comprises a substitution mutation functionally equivalent to Ala485Leu or Ala485Val in the 9° N polymerase amino acid sequence.

In certain embodiments, the altered polymerase further comprises a substitution mutation to a different amino acid at the position functionally equivalent to Cys223 in the 9° N DNA polymerase amino acid sequence. For example, in certain embodiments, the altered polymerase comprises a substitution mutation functionally equivalent to Cys223Ser in the 9° N polymerase amino acid sequence.

In certain embodiments, the at least one substitution mutation comprises a mutation to the position equivalent to Thr514, Lys477 and/or Ile521. For example, in certain embodiments, the altered polymerase comprises a substitution mutation functionally equivalent to Thr514Ala, Thr514Ser, Lys477Met and/or Ile521Leu in the 9° N polymerase amino acid sequence.

In certain embodiments, the altered polymerase can comprise an additional substitution mutation to remove an internal methionine. For example, in some embodiments, the altered polymerase comprises a substitution mutation to a different amino acid at the position functionally equivalent to Met129 in the 9° N DNA polymerase amino acid sequence. In certain embodiments, the altered polymerase comprises a substitution mutation functionally equivalent to Met129Ala in the 9° N polymerase amino acid sequence.

Also presented herein is an altered polymerase comprising the amino acid sequence of any one of SEQ ID NOs: 11-12, 14-15, 17, 19-20, 22-23, 25-26, 28, 30 and 32-40.

Also presented herein is a nucleic acid molecule encoding an altered polymerase as defined in any the above embodiments. Also presented herein is an expression vector comprising the nucleic acid molecule described above. Also presented herein is a host cell comprising the vector described above.

Also presented herein is a method for incorporating modified nucleotides into DNA comprising allowing the following components to interact: (i) an altered polymerase according to any of the above embodiments, (ii) a DNA template; and (iii) a nucleotide solution. In certain embodiments, the DNA template comprises a clustered array.

Also provided herein is a kit for performing a nucleotide incorporation reaction comprising: a polymerase as defined in any of the above embodiments and a nucleotide solution. In certain embodiments, the nucleotide solution comprises labelled nucleotides. In certain embodiments, the nucleotides comprise synthetic nucleotides. In certain embodiments, the nucleotides comprise modified nucleotides. In certain embodiments, the modified nucleotides have been modified at the 3' sugar hydroxyl such that the substituent is larger in size than the naturally occurring 3' hydroxyl group. In certain embodiments, the modified nucleotides comprise a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure

wherein Z is any of —C(R')$_2$—O—R", —C(R')$_2$—N(R")$_2$, —C(R')$_2$—N(H)R", —C(R')$_2$—S—R" and —C(R')$_2$—F, wherein each R" is or is part of a removable protecting group;

each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; or (R')$_2$ represents an alkylidene group of formula =C(R''')$_2$ wherein each R''' may be the same or different and is selected from the group comprising hydrogen and halogen atoms and alkyl groups; and wherein the molecule may be reacted to yield an intermediate in which each R" is exchanged for H or, where Z is —C(R')$_2$—F, the F is exchanged for OH, SH or NH$_2$, preferably OH, which intermediate dissociates under aqueous conditions to afford a molecule with a free 3'OH;

with the proviso that where Z is —C(R')$_2$—S—R", both R' groups are not H.

In certain embodiments, R' of the modified nucleotide or nucleoside is an alkyl or substituted alkyl. In certain embodiments, —Z of the modified nucleotide or nucleoside is of formula —C(R')$_2$—N$_3$. In certain embodiments, Z is an azidomethyl group.

In certain embodiments, the modified nucleotides are fluorescently labelled to allow their detection. In certain embodiments, the modified nucleotides comprise a nucleotide or nucleoside having a base attached to a detectable label via a cleavable linker. In certain embodiments, the detectable label comprises a fluorescent label. In certain embodiments, the kit further comprises one or more DNA template molecules and/or primers.

The details of one or more embodiments are set forth in the accompanying drawings and the description below. Other features, objects, and advantages will be apparent from the description and drawings, and from the claims.

BRIEF DESCRIPTION OF THE DRAWINGS

Figure 1:
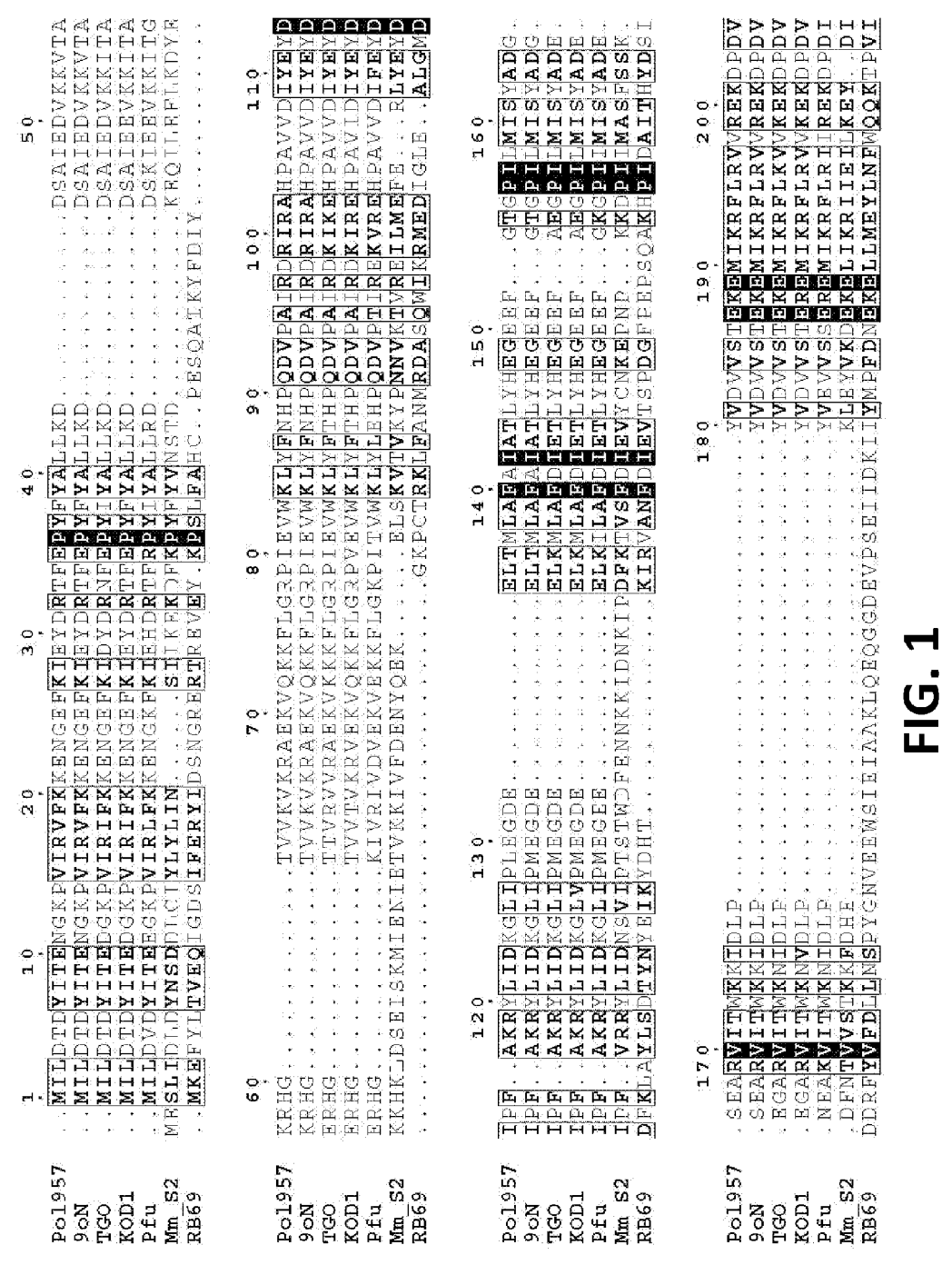
Figure 1:
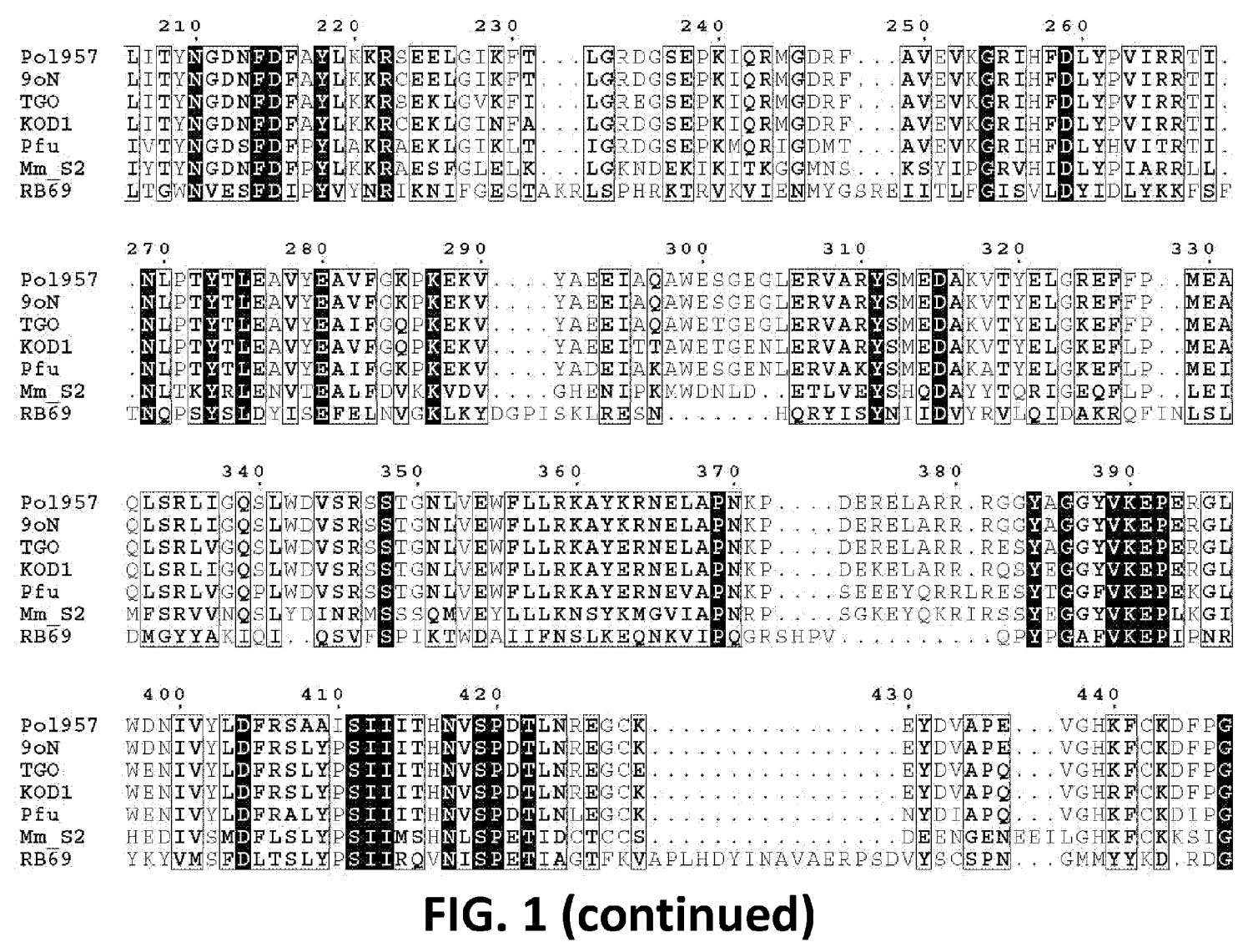
Figure 1:
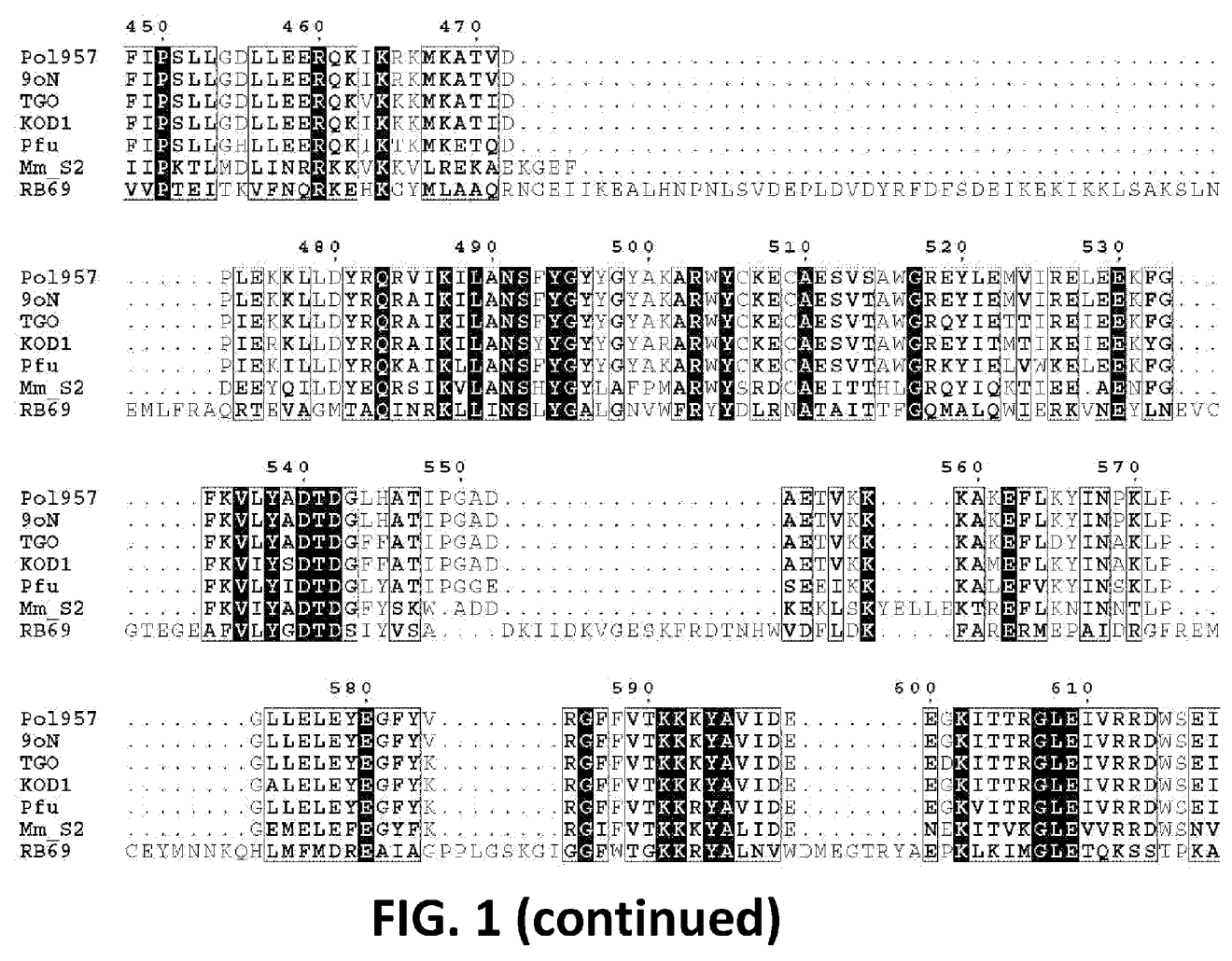
Figure 1:
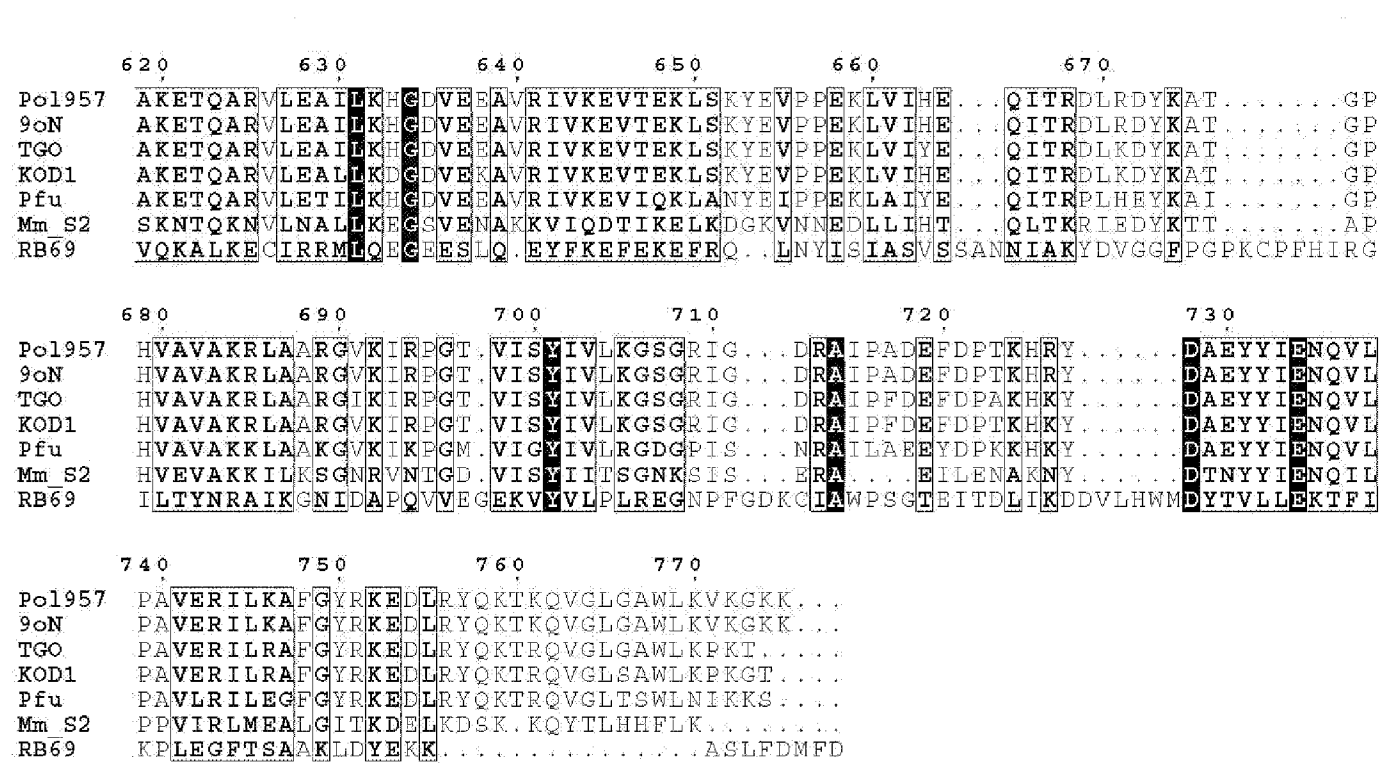

FIG. 1 is a schematic showing alignment of polymerase amino acid sequences from *Thermococcus* sp. 9° N-7 (9° N) (SEQ ID NO:10), 9° N polymerase T514S/I521L mutant (Pol957) (SEQ ID NO:43), *Thermococcus gorgonarius* (TGO) (SEQ ID NO:42), *Thermococcus kodakaraensis* (KOD 1) (SEQ ID NO:21), *Pyrococcus furiosus* (Pfu) (SEQ ID NO:18), *Methanococcus maripaludis* (MMS2) (SEQ ID NO:24) and RB69 phage DNA polymerase (SEQ ID NO:41). The numbering shown represents the numbering of amino acid residues in 9° N polymerase.

FIG. 2 is a schematic showing two highlighted portions of the alignment shown in FIG. 1. *Thermococcus* sp. 9° N-7 (9° N) (amino acids 397-533 of SEQ ID NO:10), 9° N polymerase T514S/I521L mutant (Pol957) (amino acids 397-533 of SEQ ID NO:43), *Thermococcus gorgonarius* (TGO) (amino acids 397-533 of SEQ ID NO:42), *Thermococcus kodakaraensis* (KOD 1) (amino acids 397-533 of SEQ ID NO:21), *Pyrococcus furiosus* (Pfu) (amino acids 397-533 of SEQ ID NO:18), *Methanococcus maripaludis* (MMS2) (amino acids 406-548 of SEQ ID NO:24) and RB69 phage DNA polymerase (amino acids 404-609 of SEQ ID NO:41).

DETAILED DESCRIPTION

Presented herein are polymerase enzymes for improved incorporation of nucleotide analogues, in particular nucleotides which are modified at the 3' sugar hydroxyl such that the substituent is larger in size than the naturally occurring 3' hydroxyl group. The present inventors have surprisingly identified certain altered polymerases which exhibit improved incorporation of the desired analogues and have a number of other associated advantages, including reduced error rate, reduced phasing and/or prephasing, and improved quality metrics in sequencing by synthesis reactions.

As described in greater detail hereinbelow, the inventors have surprisingly found that one or more mutations to one or more residues in the polymerase result in profound increases in turnover rate and reduction in pyrophosphorolysis. These altered polymerases have improved performance in DNA sequencing by synthesis (SBS) and result in reduced phasing and/or pre-phasing, and overall improved quality metrics in sequencing by synthesis reactions.

Phasing and pre-phasing are terms known to those of skill in the art and re used to describe the loss of synchrony in the readout of the sequence copies of a cluster. Phasing and pre-phasing cause the extracted intensities for a specific cycle to consist of the signal of the current cycle as well as noise from the preceding and following cycles. Thus, as used herein, the term "phasing" refers to a phenomenon in SBS that is caused by incomplete incorporation of a nucleotide in some portion of DNA strands within clusters by polymerases at a given sequencing cycle, and is thus a measure of the rate at which single molecules within a cluster loose sync with each other. Phasing can be measured during detection of cluster signal at each cycle, and can be reported as a percentage of detectable signal from a cluster that is out of synchrony with the signal in the cluster. As an example, a cluster is detected by a "green" fluorophore signal during cycle N. In the subsequent cycle (cycle N+1), 99.9% of the cluster signal is detected in the "red" channel and 0.1% of the signal remains from the previous cycle and is detected in the "green" channel. This result would indicate that phasing is occurring, and can be reported as a numerical value, such as a phasing value of 0.1, indicating that 0.1% of the molecules in the cluster are falling behind at each cycle.

The term "pre-phasing" as used herein refers to a phenomenon in SBS that is caused by the incorporation of nucleotides without effective 3' terminators, causing the incorporation event to go 1 cycle ahead. As the number of cycles increases, the fraction of sequences per cluster affected by phasing increases, hampering the identification of the correct base. Pre-phasing can be detected by a sequencing instrument and reported as a numerical value, such as a pre-phasing value of 0.1, indicating that 0.1% of the molecules in the cluster are running ahead at each cycle.

Detection of phasing and pre-phasing can be performed and reported according to any suitable methodology as is known in the art, for example, as described in U.S. 2012/0020537, which is incorporated by reference in its entirety. For example, as described in the Examples below, phasing is detected and reported routinely during SBS sequencing runs on sequencing instrument such as HiSeq, Genome Analyzer, NextSeq or MiSeq sequencing platforms from Illumina, Inc. (San Diego, Calif.) or any other suitable instrument known in the art.

Phasing can be caused, for example, by a polymerase which performs the reverse reaction of nucleotide incorporation, as is known to happen under conditions conducive to pyrophosphorolysis. Accordingly, the discovery of altered polymerases which decrease the incidence of phasing and/or pre-phasing is surprising and provides a great advantage in SBS applications. For example, the altered polymerases provide faster SBS cycle time, lower phasing and pre-phasing values, and longer sequencing read length. The characterization of phasing and pre-phasing for altered polymerases as provided herein is set forth in the Example section below.

The fidelity with which a sequenced library matches the original genome sequence can vary depending on the frequency of base mutation occurring at any stage from the extraction of the nucleic acid to its sequencing on a sequencing platform. This frequency places an upper limit on the probability of a sequenced base being correct. In some embodiments, the quality score is presented as a numerical value. For example, the quality score can be quoted as QXX where the XX is the score and it means that that particular call has a probability of error of $10^{-XX/10}$. Thus, as an example, Q30 equates to an error rate of 1 in 1000, or 0.1% and Q40 equates to an error rate of 1 in 10,000 or 0.01%. Put another way, if a mutation occurs one in a thousand times, then the maximum confidence (probability) that any base is correct is one in a $10^3$, i.e., a max of Q30.

In certain embodiments, the substitution mutation comprises a mutation to a residue having a non-polar side chain. Amino acids having non-polar side chains are well-known in the art and include, for example: alanine, cysteine, glycine, isoleucine, leucine, methionine, phenylalanine, proline, tryptophan, tyrosine and valine.

In certain embodiments, the substitution mutation comprises a mutation to a residue having a polar side chain. Amino acids having polar side chains are well-known in the art and include, for example: arginine, asparagine, aspartic acid, glutamine, glutamic acid, histidine, lysine, serine and threonine.

In certain embodiments, the substitution mutation comprises a mutation to a residue having a hydrophobic side chain. Amino acids having hydrophobic side chains are well-known in the art and include, for example: glycine, alanine, valine, leucine, isoleucine, proline, phenylalanine, methionine, and tryptophan.

In certain embodiments, the substitution mutation comprises a mutation to a residue having an uncharged side chain. Amino acids having uncharged side chains are well-known in the art and include, for example: glycine, serine, cysteine, asparagine, glutamine, tyrosine, and threonine.

Also presented herein is an altered polymerase comprising a substitution mutation to a semi-conserved domain of the polymerase. As used herein, the term "semi-conserved domain" refers to a portion of polymerase that is fully conserved, or at least partially conserved among various species. It has been surprisingly discovered that mutation of one or more residues in a semi-conserved domain affects the polymerase activity in the presence of 3' blocked nucleotides, resulting in profoundly improved performance in DNA sequencing by synthesis and result in reduced phasing errors, as described in the Example section below.

An alignment showing the conservation among various polymerases in the semi-conserved domains is set forth in FIGS. 1 and 2. The polymerase sequences shown in FIGS. 1 and 2 were obtained from Genbank database accession numbers Q56366 (9° N DNA polymerase), NP_577941 (Pfu), YP_182414 (KOD1), NP_987500 (MMS2), AAP75958 (RB69), P56689 (TGo).

In some embodiments, the semi-conserved domain comprises amino acids having the sequence set forth in SEQ ID NO: 1. SEQ ID NO: 1 sets forth residues in the semi-conserved domain that are conserved among various polymerases, and corresponds to residues 140-149 of the 9° N DNA polymerase amino acid sequence, which is set forth herein as SEQ ID NO: 10. Accordingly, in some embodiments of the altered polymerases presented herein comprising a substitution mutation to a semi-conserved domain of the polymerase, the substitution mutation comprises a mutation at position 5 of SEQ ID NO: 1 to any residue other than other than Thr or Val. In certain embodiments, the altered polymerase comprises a mutation to a non-polar residue at position 5 of SEQ ID NO: 1. In certain embodiments, the altered polymerase comprises a mutation to Ala, Gly or Leu at position 5 of SEQ ID NO: 1.

In some embodiments, the semi-conserved domain comprises amino acids having the sequence set forth in SEQ ID NO: 2. SEQ ID NO: 2 sets forth residues in the semi-conserved domain that are conserved among various polymerases, and corresponds to residues 147-157 of the 9° N DNA polymerase amino acid sequence, which is set forth herein as SEQ ID NO: 10. Accordingly, in some embodiments of the altered polymerases presented herein comprising a substitution mutation to a semi-conserved domain of the polymerase, the substitution mutation comprises a mutation at position 7 of SEQ ID NO: 2 to any residue other than other than Gly, Ala or Lys. In certain embodiments, the altered polymerase comprises a mutation to a polar residue at position 7 of SEQ ID NO: 2. In certain embodiments, the altered polymerase comprises a mutation to Asp at position 7 of SEQ ID NO: 2.

In some embodiments, the semi-conserved domain comprises amino acids having the sequence set forth in any of SEQ ID NOs: 3-6. SEQ ID NOs: 3-6 set forth residues in the semi-conserved domain that are conserved among various polymerases, and corresponds to residues 475-492 of the 9° N DNA polymerase amino acid sequence, which is set forth herein as SEQ ID NO: 10. Accordingly, in some embodiments of the altered polymerases presented herein comprising a substitution mutation to a semi-conserved domain of the polymerase, the substitution mutation comprises a mutation at position 2 of any of SEQ ID NOs: 3-6 to any residue other than other than Lys, Arg, Tyr or Glu. In certain embodiments, the altered polymerase comprises a mutation to a hydrophobic residue at position 2 of any of SEQ ID NOs: 3-6. In certain embodiments, the altered polymerase comprises a mutation to Trp at position 2 of any of SEQ ID NOs: 3-6.

In some embodiments of the altered polymerases presented herein comprising a substitution mutation to a semi-conserved domain of the polymerase, the substitution mutation comprises a mutation at position 4 of any of SEQ ID NOs: 3-6 to any residue other than other than Leu, Ile or Ala. In certain embodiments, the altered polymerase comprises a mutation to a polar residue at position 4 of any of SEQ ID NOs: 3-6. In certain embodiments, the altered polymerase comprises a mutation to Ser, Arg or Thr at position 4 of any of SEQ ID NOs: 3-6.

In some embodiments, the semi-conserved domain comprises amino acids having the sequence set forth in SEQ ID NO: 7. SEQ ID NO: 7 sets forth residues in the semi-conserved domain that are conserved among various polymerases, and corresponds to residues 585-598 of the 9° N DNA polymerase amino acid sequence, which is set forth herein as SEQ ID NO: 10. Accordingly, in some embodiments of the altered polymerases presented herein comprising a substitution mutation to a semi-conserved domain of the polymerase, the substitution mutation comprises a mutation at position 6 of SEQ ID NO: 7 to any residue other than other than Thr. In certain embodiments, the altered polymerase comprises a mutation to a non-polar residue at position 6 of SEQ ID NO: 7. In certain embodiments, the altered polymerase comprises a mutation to Ile or Gly at position 6 of SEQ ID NO: 7.

In some embodiments, the semi-conserved domain comprises amino acids having the sequence set forth in SEQ ID NO: 8. SEQ ID NO: 8 sets forth residues in the semi-conserved domain that are conserved among various polymerases, and corresponds to residues 634-646 of the 9° N DNA polymerase amino acid sequence, which is set forth herein as SEQ ID NO: 10. Accordingly, in some embodiments of the altered polymerases presented herein comprising a substitution mutation to a semi-conserved domain of the polymerase, the substitution mutation comprises a mutation at position 6 of SEQ ID NO: 8 to any residue other than other than Ala or Gln. In certain embodiments, the altered polymerase comprises a mutation to Val or Phe at position 6 of SEQ ID NO: 8.

In some embodiments, the semi-conserved domain comprises amino acids having the sequence set forth in SEQ ID NO: 9. SEQ ID NO: 9 sets forth residues in the semi-conserved domain that are conserved among various polymerases, and corresponds to residues 712-722 of the 9° N DNA polymerase amino acid sequence, which is set forth herein as SEQ ID NO: 10. Accordingly, in some embodiments of the altered polymerases presented herein comprising a substitution mutation to a semi-conserved domain of the polymerase, the substitution mutation comprises a mutation at position 7 of SEQ ID NO: 9 to any residue other than other than Asp, Glu or Gly. In certain embodiments, the altered polymerase comprises a mutation to an uncharged residue at position 7 of SEQ ID NO: 9. In certain embodiments, the altered polymerase comprises a mutation to Asn at position 7 of SEQ ID NO: 9.

In some embodiments, the polymerase is a DNA polymerase. In certain embodiments, the DNA polymerase is a family B type DNA polymerase. The polymerase can be, for example, a family B archael DNA polymerase, human DNA polymerase-α, and phage polymerases. Any phage polymerase can be used in the embodiments presented herein, including, for example phage polymerases such as T4, RB69, and phi29 phage DNA polymerases.

Family B archael DNA polymerases are well known in the art as exemplified by the disclosure of U.S. Pat. No. 8,283,149, which is incorporated by reference in its entirety. In certain embodiments the archael DNA polymerase is from hyperthermophilic archea, which means that the polymerases are often thermostable. Accordingly, in a further preferred embodiment the polymerase is selected from Vent, Deep Vent, 9° N and Pfu polymerase. Vent and Deep Vent are commercial names used for family B DNA polymerases isolated from the hyperthermophilic archaeon *Thermococcus litoralis*. 9° N polymerase was also identified from *Thermococcus* sp. Pfu polymerase was isolated from *Pyrococcus furiosus*.

In certain embodiments, the family B archael DNA polymerase is from a genus such as, for example those of the genus *Thermococcus*, *Pyrococcus* and *Methanococcus*. Members of the genus *Thermococcus* are well known in the art and include, but are not limited to *Thermococcus 4557*, *Thermococcus barophilus*, *Thermococcus gammatolerans*, *Thermococcus onnurineus*, *Thermococcus sibiricus*, *Thermococcus kodakarensis*, *Thermococcus gorgonarius*. Members of the genus *Pyrococcus* are well known in the art and include, but are not limited to *Pyrococcus NA2*, *Pyrococcus abyssi*, *Pyrococcus furiosus*, *Pyrococcus horikoshii*, *Pyrococcus yayanosii*, *Pyrococcus endeavori*, *Pyrococcus glycovorans*, *Pyrococcus woesei*. Members of the genus *Methanococcus* are well known in the art and include, but are not limited to *M. aeolicus, M. maripaludis, M. vannielii, M. voltae, "M. thermolithotrophicus"* and *"M. jannaschii"*.

For example, the polymerase can be selected from the group consisting of Vent, Deep Vent, 9° N, and Pfu polymerase. In certain embodiments, the family B archael DNA polymerase is 9° N polymerase.

By "functionally equivalent" it is meant that the control polymerase, in the case of studies using a different polymerase entirely, will contain the amino acid substitution that is considered to occur at the amino acid position in the other polymerase that has the same functional role in the enzyme. As an example, the mutation at position 412 from Tyrosine to Valine (Y412V) in the Vent DNA polymerase would be functionally equivalent to a substitution at position 409 from Tyrosine to Valine (Y409V) in the 9° N polymerase.

Generally functionally equivalent substitution mutations in two or more different polymerases occur at homologous amino acid positions in the amino acid sequences of the polymerases. Hence, use herein of the term "functionally equivalent" also encompasses mutations that are "positionally equivalent" or "homologous" to a given mutation, regardless of whether or not the particular function of the mutated amino acid is known. It is possible to identify positionally equivalent or homologous amino acid residues in the amino acid sequences of two or more different polymerases on the basis of sequence alignment and/or molecular modelling. An example of sequence alignment to identify positionally equivalent and/or functionally equivalent residues is set forth in FIGS. 1 and 2. Thus, for example, as shown in FIG. 2, the residues in the semi-conserved domain identified as positions 475-492 of the 9° N DNA polymerase amino acid sequence. The corresponding residues in TGO, KOD1, Pfu, MmS2 and RB69 polymerases are identified in the Figure as vertically aligned and are considered positionally equivalent as well as functionally equivalent to the corresponding residue in the 9° N DNA polymerase amino acid sequence.

The altered polymerases described hereinabove can comprise additional substitution mutations that are known to enhance one or more aspects of polymerase activity in the presence of 3' blocked nucleotides and/or in DNA sequencing applications. For example, in some embodiments, in addition to any of the above mutations, the altered polymerase can further comprise substitution mutations at positions functionally equivalent to Leu408 and/or Tyr409 and/or Pro410 in the 9° N DNA polymerase amino acid sequence. Any of a variety of substitution mutations at one or more of positions at positions functionally equivalent to 408-410 in the 9° N DNA polymerase amino acid sequence which results in increased incorporation of blocked nucleotides can be made, as is known in the art and exemplified by the disclosure of US 2006/0240439 and US 2006/0281109, each of which is incorporated by reference in its entirety. For example, the substitution mutations can comprise substitution mutations homologous to Leu408Ala and/or Tyr409Ala and/or Pro410Ile in the 9° N DNA polymerase amino acid sequence. In certain embodiments, in addition to any of the above mutations, the altered polymerase further comprises substitution mutations at positions functionally equivalent to Ala485 in the 9° N DNA polymerase amino acid sequence. For example, in some embodiments, the polymerase comprises a substitution mutation functionally equivalent to Ala485Leu or Ala485Val in the 9° N polymerase amino acid sequence.

In some embodiments, in addition to any of the above mutations, the altered polymerase can comprise reduced exonuclease activity as compared to a wild type polymerase. Any of a variety of substitution mutations at one or more of positions known to result in reduced exonuclease activity can be made, as is known in the art and exemplified by the incorporated materials of US 2006/0240439 and US 2006/0281109. For example, in some embodiments, in addition to the above mutations, the altered polymerase can further comprise substitution mutations at positions functionally equivalent to Asp141 and/or Glu143 in the 9° N DNA polymerase amino acid sequence.

In certain embodiments, in addition to any of the above mutations, the altered polymerase further comprises a substitution mutation to a different amino acid at the position functionally equivalent to Cys223 in the 9° N DNA polymerase amino acid sequence as is known in the art and exemplified by the incorporated materials of US 2006/0281109. For example, in certain embodiments, the altered polymerase comprises a substitution mutation functionally equivalent to Cys223Ser in the 9° N polymerase amino acid sequence.

In certain embodiments, in addition to any of the above mutations, the altered polymerase can comprise one or more mutation to the positions equivalent to Thr514 and/or Ile521 in the 9° N DNA polymerase amino acid sequence as is known in the art and exemplified by the disclosure of PCT/US2013/031694, which is incorporated by reference in its entirety. For example, in certain embodiments, the altered polymerase comprises a substitution mutation functionally equivalent to Thr514Ala, Thr514Ser and/or Ile521Leu in the 9° N polymerase amino acid sequence.

In certain embodiments, in addition to any of the above mutations, the altered polymerase can comprise one or more mutation to the positions equivalent to Arg713 in the 9° N DNA polymerase amino acid sequence as is known in the art and exemplified by the disclosure of U.S. Pat. No. 8,623,628, which is incorporated by reference in its entirety. For example, in certain embodiments, the altered polymerase comprises a substitution mutation functionally equivalent to Arg713Gly, Arg713Met or Arg713Ala in the 9° N polymerase amino acid sequence.

In certain embodiments, in addition to any of the above mutations, the altered polymerase can comprise one or more mutation to the positions equivalent to Arg743 and/or Lys705 in the 9° N DNA polymerase amino acid sequence, as is known in the art and exemplified by the disclosure of U.S. Pat. No. 8,623,628, which is incorporated by reference in its entirety. For example, in certain embodiments, the altered polymerase comprises a substitution mutation functionally equivalent to Arg743Ala and/or Lys705Ala in the 9° N polymerase amino acid sequence.

In certain embodiments, in addition to any of the above mutations, the altered polymerase can comprise one or more mutation to the positions equivalent to Lys477 in the 9° N DNA polymerase amino acid sequence as is known in the art and exemplified by the disclosure of U.S. Application 62/018,470, filed on Jun. 27, 2014 and entitled "MODIFIED POLYMERASES FOR IMPROVED INCORPORATION OF NUCLEOTIDE ANALOGUES", which is incorporated by reference in its entirety. For example, in certain embodiments, the altered polymerase comprises a substitution mutation functionally equivalent to Lys477Met in the 9° N polymerase amino acid sequence.

In certain embodiments, in addition to any of the above mutations, the altered polymerase can comprise one or more additional substitution mutation to remove an internal methionine. For example, in some embodiments, the altered polymerase comprises a substitution mutation to a different amino acid at the position functionally equivalent to Met129 in the 9° N DNA polymerase amino acid sequence. In certain embodiments, the altered polymerase comprises a substitution mutation functionally equivalent to Met129Ala in the 9° N polymerase amino acid sequence.

Mutating Polymerases

Various types of mutagenesis are optionally used in the present disclosure, e.g., to modify polymerases to produce variants, e.g., in accordance with polymerase models and model predictions as discussed above, or using random or semi-random mutational approaches. In general, any available mutagenesis procedure can be used for making polymerase mutants. Such mutagenesis procedures optionally include selection of mutant nucleic acids and polypeptides for one or more activity of interest (e.g., reduced pyrophosphorolysis, increased turnover e.g., for a given nucleotide analog). Procedures that can be used include, but are not limited to: site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to persons of skill. The starting polymerase for mutation can be any of those noted herein, including available polymerase mutants such as those identified e.g., in US 2006/0240439 and US 2006/0281109, each of which is incorporated by reference in its entirety.

Optionally, mutagenesis can be guided by known information from a naturally occurring polymerase molecule, or of a known altered or mutated polymerase (e.g., using an existing mutant polymerase as noted in the preceding references), e.g., sequence, sequence comparisons, physical properties, crystal structure and/or the like as discussed above. However, in another class of embodiments, modification can be essentially random (e.g., as in classical or "family" DNA shuffling, see, e.g., Crameri et al. (1998) "DNA shuffling of a family of genes from diverse species accelerates directed evolution" Nature 391:288-291).

Additional information on mutation formats is found in: Sambrook et al., Molecular Cloning—A Laboratory Manual (3rd Ed.), Vol. 1-3, Cold Spring Harbor Laboratory, Cold Spring Harbor, N.Y., 2000 ("Sambrook"); Current Protocols in Molecular Biology, F. M. Ausubel et al., eds., Current Protocols, a joint venture between Greene Publishing Associates, Inc. and John Wiley & Sons, Inc., (supplemented through 2011) ("Ausubel")) and PCR Protocols A Guide to Methods and Applications (Innis et al. eds) Academic Press Inc. San Diego, Calif. (1990) ("Innis"). The following publications and references cited within provide additional detail on mutation formats: Arnold, Protein engineering for unusual environments, Current Opinion in Biotechnology 4:450-455 (1993); Bass et al., Mutant Trp repressors with new DNA-binding specificities, Science 242:240-245 (1988); Bordo and Argos (1991) Suggestions for "Safe" Residue Substitutions in Site-directed Mutagenesis 217:721-729; Botstein & Shortle, Strategies and applications of in vitro mutagenesis, Science 229:1193-1201 (1985); Carter et al., Improved oligonucleotide site-directed mutagenesis using M13 vectors, Nucl. Acids Res. 13: 4431-4443 (1985); Carter, Site-directed mutagenesis, Biochem. J. 237:1-7 (1986); Carter, Improved oligonucleotide-directed mutagenesis using M13 vectors, Methods in Enzymol. 154: 382-403 (1987); Dale et al., Oligonucleotide-directed random mutagenesis using the phosphorothioate method, Methods Mol. Biol. 57:369-374 (1996); Eghtedarzadeh & Henikoff, Use of oligonucleotides to generate large deletions, Nucl. Acids Res. 14: 5115 (1986); Fritz et al., Oligonucleotide-directed construction of mutations: a gapped duplex DNA procedure without enzymatic reactions in vitro, Nucl. Acids Res. 16: 6987-6999 (1988); Grundstrom et al., Oligonucleotide-directed mutagenesis by microscale 'shot-gun' gene synthesis, Nucl. Acids Res. 13: 3305-3316 (1985); Hayes (2002) Combining Computational and Experimental Screening for rapid Optimization of Protein Properties PNAS 99(25) 15926-15931; Kunkel, The efficiency of oligonucleotide directed mutagenesis, in Nucleic Acids & Molecular Biology (Eckstein, F. and Lilley, D. M. J. eds., Springer Verlag, Berlin)) (1987); Kunkel, Rapid and efficient site-specific mutagenesis without phenotypic selection, Proc. Natl. Acad. Sci. USA 82:488-492 (1985); Kunkel et al., Rapid and efficient site-specific mutagenesis without phenotypic selection, Methods in Enzymol. 154, 367-382 (1987); Kramer et al., The gapped duplex DNA approach to oligonucleotide-directed mutation construction, Nucl. Acids Res. 12: 9441-9456 (1984); Kramer & Fritz Oligonucleotide-directed construction of mutations via gapped duplex DNA, Methods in Enzymol. 154:350-367 (1987); Kramer et al., Point Mismatch Repair, Cell 38:879-887 (1984); Kramer et al., Improved enzymatic in vitro reactions in the gapped duplex DNA approach to oligonucleotide-directed construction of mutations, Nucl. Acids Res. 16: 7207 (1988); Ling et al., Approaches to DNA mutagenesis: an overview, Anal Biochem. 254(2): 157-178 (1997); Lorimer and Pastan Nucleic Acids Res. 23, 3067-8 (1995); Mandecki, Oligonucleotide-directed double-strand break repair in plasmids of *Escherichia coli*: a method for site-specific mutagenesis, Proc. Natl. Acad. Sci. USA, 83:7177-7181(1986); Nakamaye & Eckstein, Inhibition of restriction endonuclease Nci I cleavage by phosphorothioate groups and its application to oligonucleotide-directed mutagenesis, Nucl. Acids Res. 14: 9679-9698 (1986); Nambiar et al., Total synthesis and cloning of a gene coding for the ribonuclease S protein, Science 223: 1299-1301(1984); Sakamar and Khorana, Total synthesis and expression of a gene for the a-subunit of bovine rod outer segment guanine nucleotide-binding protein (transducin), Nucl. Acids Res. 14: 6361-6372 (1988); Sayers et al., Y-T Exonucleases in phosphorothioate-based oligonucleotide-directed mutagenesis, Nucl. Acids Res. 16:791-802 (1988); Sayers et al., Strand specific cleavage of phosphorothioate-containing DNA by reaction with restriction endonucleases in the presence of ethidium bromide, (1988) Nucl. Acids Res. 16: 803-814; Sieber, et al., Nature Biotechnology, 19:456-460 (2001); Smith, In vitro mutagenesis, Ann. Rev. Genet. 19:423-462 (1985); Methods in Enzymol. 100: 468-500 (1983); Methods in Enzymol. 154: 329-350 (1987); Stemmer, Nature 370, 389-91(1994); Taylor et al., The use of phosphorothioate-modified DNA in restriction enzyme reactions to prepare nicked DNA, Nucl. Acids Res. 13: 8749-8764 (1985); Taylor et al., The rapid generation of oligonucleotide-directed mutations at high frequency using phosphorothioate-modified DNA, Nucl. Acids Res. 13: 8765-8787 (1985); Wells et al., Importance of hydrogen-bond formation in stabilizing the transition state of subtilisin, Phil. Trans. R. Soc. Lond. A 317: 415-423 (1986); Wells et al., Cassette mutagenesis: an efficient method for generation of multiple mutations at defined sites, Gene 34:315-323 (1985); Zoller & Smith, Oligonucleotide-directed mutagenesis using M 13-derived vectors: an efficient and general procedure for the production of point mutations in any DNA fragment, Nucleic Acids Res. 10:6487-6500 (1982); Zoller & Smith, Oligonucleotide-directed mutagenesis of DNA fragments cloned into M13 vectors, Methods in Enzymol. 100:468-500 (1983); Zoller & Smith, Oligonucleotide-directed mutagenesis: a simple method using two oligonucleotide primers and a single-stranded DNA template, Methods in Enzymol. 154:329-350 (1987); Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296. Additional details on many of the above methods can be found in Methods in Enzymology Volume 154, which also describes useful controls for trouble-shooting problems with various mutagenesis methods.

Making and Isolating Recombinant Polymerases

Generally, nucleic acids encoding a polymerase as presented herein can be made by cloning, recombination, in vitro synthesis, in vitro amplification and/or other available methods. A variety of recombinant methods can be used for expressing an expression vector that encodes a polymerase as presented herein. Methods for making recombinant nucleic acids, expression and isolation of expressed products are well known and described in the art. A number of exemplary mutations and combinations of mutations, as well as strategies for design of desirable mutations, are described herein. Methods for making and selecting mutations in the active site of polymerases, including for modifying steric features in or near the active site to permit improved access by nucleotide analogs are found hereinabove and, e.g., in WO 2007/076057 and PCT/US2007/022459, which are incorporated by reference in their entireties.

Additional useful references for mutation, recombinant and in vitro nucleic acid manipulation methods (including cloning, expression, PCR, and the like) include Berger and Kimmel, Guide to Molecular Cloning Techniques, Methods in Enzymology volume 152 Academic Press, Inc., San Diego, Calif. (Berger); Kaufman et al. (2003) Handbook of Molecular and Cellular Methods in Biology and Medicine Second Edition Ceske (ed) CRC Press (Kaufman); and The Nucleic Acid Protocols Handbook Ralph Rapley (ed) (2000) Cold Spring Harbor, Humana Press Inc (Rapley); Chen et al. (ed) PCR Cloning Protocols, Second Edition (Methods in Molecular Biology, volume 192) Humana Press; and in Viljoen et al. (2005) Molecular Diagnostic PCR Handbook Springer, ISBN 1402034032.

In addition, a plethora of kits are commercially available for the purification of plasmids or other relevant nucleic acids from cells, (see, e.g., EasyPrep™, FlexiPrep™ both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both.

Other useful references, e.g. for cell isolation and culture (e.g., for subsequent nucleic acid isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York) and Atlas and Parks (eds) The Handbook of Microbiological Media (1993) CRC Press, Boca Raton, Fla.

Nucleic acids encoding the recombinant polymerases of disclosed herein are also a feature of embodiments presented herein. A particular amino acid can be encoded by multiple codons, and certain translation systems (e.g., prokaryotic or eukaryotic cells) often exhibit codon bias, e.g., different organisms often prefer one of the several synonymous codons that encode the same amino acid. As such, nucleic acids presented herein are optionally "codon optimized," meaning that the nucleic acids are synthesized to include codons that are preferred by the particular translation system being employed to express the polymerase. For example, when it is desirable to express the polymerase in a bacterial cell (or even a particular strain of bacteria), the nucleic acid can be synthesized to include codons most frequently found in the genome of that bacterial cell, for efficient expression of the polymerase. A similar strategy can be employed when it is desirable to express the polymerase in a eukaryotic cell, e.g., the nucleic acid can include codons preferred by that eukaryotic cell.

A variety of protein isolation and detection methods are known and can be used to isolate polymerases, e.g., from recombinant cultures of cells expressing the recombinant polymerases presented herein. A variety of protein isolation and detection methods are well known in the art, including, e.g., those set forth in R. Scopes, Protein Purification, Springer-Verlag, N.Y. (1982); Deutscher, Methods in Enzymology Vol. 182: Guide to Protein Purification, Academic Press, Inc. N.Y. (1990); Sandana (1997) Bioseparation of Proteins, Academic Press, Inc.; Bollag et al. (1996) Protein Methods, 2.sup.nd Edition Wiley-Liss, NY; Walker (1996) The Protein Protocols Handbook Humana Press, NJ, Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice 3.sup.rd Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, NJ; and the references cited therein. Additional details regarding protein purification and detection methods can be found in Satinder Ahuja ed., Handbook of Bioseparations, Academic Press (2000).

Methods of Use

The altered polymerases presented herein can be used in a sequencing procedure, such as a sequencing-by-synthesis (SBS) technique. Briefly, SBS can be initiated by contacting the target nucleic acids with one or more labeled nucleotides, DNA polymerase, etc. Those features where a primer is extended using the target nucleic acid as template will incorporate a labeled nucleotide that can be detected. Optionally, the labeled nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., *Nature* 456: 53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, Genome Res. 11(1), 3-11 (2001); Ronaghi et al. *Science* 281(5375), 363 (1998); U.S. Pat. Nos. 6,210,891; 6,258,568 and 6,274,320, each of which is incorporated herein by reference). In pyrosequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to arrays of the present disclosure are described, for example, in WIPO Pat. App. Ser. No. PCT/US11/57111, US Pat. App. Pub. No. 2005/0191698 A1, U.S. Pat. No. 7,595,883, and U.S. Pat. No. 7,244,559, each of which is incorporated herein by reference.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides. Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US Pat. App. Pub. Nos. 2009/0026082 A1; 2009/0127589 A1; 2010/0137143 A1; or 2010/0282617 A1, each of which is incorporated herein by reference.

Accordingly, presented herein are methods for incorporating nucleotide analogues into DNA comprising allowing the following components to interact: (i) an altered polymerase according to any of the above embodiments, (ii) a DNA template; and (iii) a nucleotide solution. In certain embodiments, the DNA template comprises a clustered array. In certain embodiments, the nucleotides are modified at the 3' sugar hydroxyl, and include modifications at the 3' sugar hydroxyl such that the substituent is larger in size than the naturally occurring 3' hydroxyl group.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a polymerase, or the amino acid sequence of a polymerase) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Current Protocols in Molecular Biology, Ausubel et al., eds., Current Protocols, a joint venture between Greene Publishing Associates, Inc. and John Wiley & Sons, Inc., supplemented through 2004).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Nucleic Acids Encoding Altered Polymerases

Further presented herein are nucleic acid molecules encoding the altered polymerase enzymes presented herein. For any given altered polymerase which is a mutant version of a polymerase for which the amino acid sequence and preferably also the wild type nucleotide sequence encoding the polymerase is known, it is possible to obtain a nucleotide sequence encoding the mutant according to the basic principles of molecular biology. For example, given that the wild type nucleotide sequence encoding 9° N polymerase is known, it is possible to deduce a nucleotide sequence encoding any given mutant version of 9° N having one or more amino acid substitutions using the standard genetic code. Similarly, nucleotide sequences can readily be derived for mutant versions other polymerases such as, for example, Vent™, Pfu, Tsp JDF-3, Taq, etc. Nucleic acid molecules having the required nucleotide sequence may then be constructed using standard molecular biology techniques known in the art.

In accordance with the embodiments presented herein, a defined nucleic acid includes not only the identical nucleic acid but also any minor base variations including, in particular, substitutions in cases which result in a synonymous codon (a different codon specifying the same amino acid residue) due to the degenerate code in conservative amino acid substitutions. The term "nucleic acid sequence" also includes the complementary sequence to any single stranded sequence given regarding base variations.

The nucleic acid molecules described herein may also, advantageously, be included in a suitable expression vector to express the polymerase proteins encoded therefrom in a suitable host. Incorporation of cloned DNA into a suitable expression vector for subsequent transformation of said cell and subsequent selection of the transformed cells is well known to those skilled in the art as provided in Sambrook et al. (1989), Molecular cloning: A Laboratory Manual, Cold Spring Harbor Laboratory, which is incorporated by reference in its entirety.

Such an expression vector includes a vector having a nucleic acid according to the embodiments presented herein operably linked to regulatory sequences, such as promoter regions, that are capable of effecting expression of said DNA fragments. The term "operably linked" refers to a juxtaposition wherein the components described are in a relationship permitting them to function in their intended manner. Such vectors may be transformed into a suitable host cell to provide for the expression of a protein according to the embodiments presented herein.

The nucleic acid molecule may encode a mature protein or a protein having a prosequence, including that encoding a leader sequence on the preprotein which is then cleaved by the host cell to form a mature protein. The vectors may be, for example, plasmid, virus or phage vectors provided with an origin of replication, and optionally a promoter for the expression of said nucleotide and optionally a regulator of the promoter. The vectors may contain one or more selectable markers, such as, for example, an antibiotic resistance gene.

Regulatory elements required for expression include promoter sequences to bind RNA polymerase and to direct an appropriate level of transcription initiation and also translation initiation sequences for ribosome binding. For example, a bacterial expression vector may include a promoter such as the lac promoter and for translation initiation the Shine-Dalgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or be assembled from the sequences described by methods well known in the art.

Transcription of DNA encoding the polymerase by higher eukaryotes may be optimised by including an enhancer sequence in the vector. Enhancers are cis-acting elements of DNA that act on a promoter to increase the level of transcription. Vectors will also generally include origins of replication in addition to the selectable markers.

Example 1

General Assay Methods and Conditions

The following paragraphs describe general assay conditions used in the Examples presented below.
1. Cloning and Expression of Polymerases This section describes the approach used for cloning and expression of the various polymerase mutants used in the Examples below.

Mutagenesis was performed on the gene encoding the backbone gene sequence for the polymerase using standard site-directed mutagenesis methodology. For each mutation made, proper sequence of the mutated genes was confirmed by sequencing the cloned gene sequence.

The polymerase genes were subcloned into a pET11a vector and transformed into BL21 Star (DE3) expression cells from Invitrogen. The transformed cells were cultured at 37° C. in 2.8 L Fernbock flasks until an OD600 of 0.8 was reached. Protein expression was then induced by addition of 1 mM IPTG, followed by 3 hours of additional growth. The cultures were then centrifuged at 7000 rpm for 20 minutes. Cell pellets were stored at −20° C. until purification.

Bacterial cell lysis was performed by resuspending the frozen cultures in 10× w/v lysis buffer (Tris pH 7.5, 500 mM NaCl, 1 mM EDTA, 1 mM DTT). EDTA free protease inhibitor (Roche) was added to the resuspended cell pellet. All lysis and purification steps were performed at 4° C. The resuspended culture was passed through a microfluidizer four times to complete cell lysis. The lysate was then centrifuged at 20,000 rpm for 20 minutes to remove cell debris. Polyethylenimine (final concentration 0.5%) was added to the supernatant slowly with stirring for 45 minutes to precipitate bacterial nucleic acid. The lysate was centrifuged at 20,000 rpm for 20 minutes; the pellet was discarded. The lysate was then ammonium sulfate precipitated using two volumes of cold saturated $(NH_4)_2SO_4$ in sterile $dH_2O$. The precipitated protein was centrifuged at 20,000 rpm for 20 minutes. The protein pellets were resuspended in 250 mL of Buffer A (50 mM Tris pH 7.5, 50 mM KCl, 0.1 mM EDTA, 1 mM DTT). The resuspended lysate was then purified using a 5 mL SP FastFlow column (GE) pre-equilibrated in buffer A. The column was eluted using a 50 mL gradient from 0.1 to 1M KCl. Peak fractions were pooled and diluted with buffer C (Tris pH 7.5, 0.1 mM EDTA, 1 mM DTT) until the conductivity was equal to buffer D (Tris pH 7.5, 50 mM KCl, 0.1 mM EDTA, 1 mM DTT). The pooled fractions were then loaded onto a 5 mL HiTrap Heparin Fastflow column. The polymerase was then eluted using a 100 mL gradient from 50 mM to 1M KCl. Peak fractions were pooled, dialyzed into storage buffer (20 mM Tris pH 7.5, 300 mM KCl, 0.1 mM EDTA, 50% Glycerol) and frozen at −80° C.
2. Phasing/Pre-Phasing Analysis This section describes the approach used for to analyze performance of the polymerase mutants used in the Examples below in a sequencing by synthesis assay.

Sequencing experiments are used to generate phasing and pre-phasing values. The experiments are carried out on a MiSeq system (Illumina, Inc., San Diego, Calif.), according to manufacturer instructions. For example, for each polymerase, a separate incorporation mixes (IMX) was generated and a 150 cycle run was performed using a different flowcell lane for each IMX. Standard V3 MiSeq reagent formulations were used, with the standard polymerase substituted with the polymerase being tested, at a concentration of 30 μg/mL. The standard time for incubation of IMX on the flowcell was shortened to 6 seconds. The DNA library used was made following the standard Nextera™ protocol (Illumina, Inc.) using *E. coli* genomic DNA. Illumina RTA Software was used to evaluate phasing and pre-phasing levels.

Example 2

Identification and Screen of 9° N Polymerase Mutants for Phasing/Pre-Phasing

A saturation mutagenesis screen of residues in the 3' block pocket is performed. Mutations to modified 9° N polymerase backbone sequence (SEQ ID NO: 31) are generated, cloned, expressed and purified as described generally in Example 1.

The purified mutant polymerases are screened for phasing/pre-phasing activity as described above in Example 1. The phasing and pre-phasing activity of the tested mutants is compared to the control polymerase having the sequence set forth in SEQ ID NOs: 31.

Results of the analysis are summarized in the table below. As shown in the table, each of the above mutants shows unexpected and significant improvements in one or more of phasing and pre-phasing when compared to the control polymerases.

| Mutant | SEQ ID NO: | Phasing reduction compared to control? |
|---|---|---|
| Control | 31 | — |
| Mutant 1 | 33 | Yes |
| Mutant 2 | 34 | Yes |
| Mutant 3 | 35 | Yes |
| Mutant 4 | 36 | Yes |
| Mutant 5 | 37 | Yes |
| Mutant 6 | 38 | Yes |
| Mutant 7 | 39 | Yes |
| Mutant 8 | 40 | Yes |

Example 3

Screen of Mutants of 9° N WT Polymerase

Mutations to a *Thermococcus* sp. 9° N-7 (9° N) wild type polymerase backbone sequence (SEQ ID NO: 10) are generated, cloned, expressed and purified as described generally in Example 1, producing polymerase enzymes having the amino acid sequences set forth as SEQ ID NOs: 11-12, as described in the table below.

The purified mutant polymerases are screened for phasing/pre-phasing activity as generally described above in Example 1 and compared to the control polymerase having the sequence set forth in SEQ ID NO: 10. Those polymerases having the following mutations are shown to have improved phasing and/or pre-phasing activity compared to the control:

| Mutant | SEQ ID NO: |
|---|---|
| T144A | 11 |
| T144G | 11 |
| T144L | 11 |
| G153D | 11 |
| K476W | 11 |
| L478S | 11 |
| L478R | 11 |
| L478T | 11 |
| T590I | 11 |
| T590G | 11 |
| A639V | 11 |
| A639F | 11 |
| D718N | 11 |
| T144A G153D K476W L478S T590I A639V D718N | 11 |
| T144A G153D T590I A639V D718N | 11 |
| K476W L478S T590I | 11 |
| K476W T590I | 11 |
| T144A L408A Y409A P410I | 12 |
| G153D L408A Y409A P410I | 12 |
| K476W L408A Y409A P410I | 12 |
| L478S L408A Y409A P410I | 12 |
| T590I L408A Y409A P410I | 12 |
| A639V L408A Y409A P410I | 12 |
| D718N L408A Y409A P410I | 12 |
| T144A G153D K476W L478S T590I A639V D718N L408A Y409A P410I | 12 |
| T144A G153D T590I A639V D718N L408A Y409A P410I | 12 |
| K476W L478S T590I L408A Y409A P410I | 12 |
| K476W T590I L408A Y409A P410I | 12 |
| T144A L408A Y409A P410I A485V | 12 |
| G153D L408A Y409A P410I A485V | 12 |
| K476W L408A Y409A P410I A485V | 12 |

| Mutant | SEQ ID NO: |
|---|---|
| L478S | 12 |
| L408A | |
| Y409A | |
| P410I | |
| A485V | |
| T590I | 12 |
| L408A | |
| Y409A | |
| P410I | |
| A485V | |
| A639V | 12 |
| L408A | |
| Y409A | |
| P410I | |
| A485V | |
| D718N | 12 |
| L408A | |
| Y409A | |
| P410I | |
| A485V | |
| T144A | 12 |
| G153D | |
| K476W | |
| L478S | |
| T590I | |
| A639V | |
| D718N | |
| L408A | |
| Y409A | |
| P410I | |
| A485V | |
| T144A | 12 |
| G153D | |
| T590I | |
| A639V | |
| D718N | |
| L408A | |
| Y409A | |
| P410I | |
| A485V | |
| K476W | 12 |
| L478S | |
| T590I | |
| L408A | |
| Y409A | |
| P410I | |
| A485V | |
| K476W | 12 |
| T590I | |
| L408A | |
| Y409A | |
| P410I | |
| A485V | |

Example 4

Screen of Mutants of 9° N Exo⁻ Polymerase

Mutations to 9° N Exo⁻ polymerase backbone sequence (SEQ ID NO: 13) are generated, cloned, expressed and purified as described generally in Example 1, producing polymerase enzymes having the amino acid sequences set forth as SEQ ID NOs: 14-15.

The purified mutant polymerases are screened for phasing/pre-phasing activity as generally described above in Example 1 and compared to the control polymerase having the sequence set forth in SEQ ID NO: 13. Those polymerases having the following mutations are shown to have improved phasing and/or pre-phasing activity compared to the control:

| Mutant | SEQ ID NO: |
|---|---|
| T144A | 14 |
| G153D | 14 |
| K476W | 14 |
| L478S | 14 |
| T590I | 14 |
| A639V | 14 |
| D718N | 14 |
| T144A | 14 |
| G153D | |
| K476W | |
| L478S | |
| T590I | |
| A639V | |
| D718N | |
| T144A | 14 |
| G153D | |
| T590I | |
| A639V | |
| D718N | |
| K476W | 14 |
| L478S | |
| T590I | |
| K476W | 14 |
| T590I | |
| T144A | 15 |
| L408A | |
| Y409A | |
| P410I | |
| G153D | 15 |
| L408A | |
| Y409A | |
| P410I | |
| K476W | 15 |
| L408A | |
| Y409A | |
| P410I | |
| L478S | 15 |
| L408A | |
| Y409A | |
| P410I | |
| T590I | 15 |
| L408A | |
| Y409A | |
| P410I | |
| A639V | 15 |
| L408A | |
| Y409A | |
| P410I | |
| D718N | 15 |
| L408A | |
| Y409A | |
| P410I | |
| T144A | 15 |
| G153D | |
| K476W | |
| L478S | |
| T590I | |
| A639V | |
| D718N | |
| L408A | |
| Y409A | |
| P410I | |
| T144A | 15 |
| G153D | |
| T590I | |
| A639V | |
| D718N | |
| L408A | |
| Y409A | |
| P410I | |
| K476W | 15 |
| L478S | |
| T590I | |
| L408A | |
| Y409A | |
| P410I | |

-continued

| Mutant | SEQ ID NO: |
|---|---|
| K476W<br>T590I<br>L408A<br>Y409A<br>P410I | 15 |
| T144A<br>L408A<br>Y409A<br>P410I<br>A485V | 15 |
| G153D<br>L408A<br>Y409A<br>P410I<br>A485V | 15 |
| K476W<br>L408A<br>Y409A<br>P410I<br>A485V<br>L478S | 15 |
| L408A<br>Y409A<br>P410I<br>A485V<br>T590I | 15 |
| L408A<br>Y409A<br>P410I<br>A485V<br>A639V | 15 |
| L408A<br>Y409A<br>P410I<br>A485V<br>D718N | 15 |
| L408A<br>Y409A<br>P410I<br>A485V<br>T144A<br>G153D<br>K476W<br>L478S<br>T590I<br>A639V<br>D718N<br>L408A<br>Y409A<br>P410I<br>A485V | 15 |
| T144A<br>G153D<br>T590I<br>A639V<br>D718N<br>L408A<br>Y409A<br>P410I<br>A485V | 15 |
| K476W<br>L478S<br>T590I<br>L408A<br>Y409A<br>P410I<br>A485V | 15 |
| K476W<br>T590I<br>L408A<br>Y409A<br>P410I<br>A485V | 15 |

Example 5

Screen of Mutants of Altered 9° N Polymerase

Mutations to an altered 9° N polymerase backbone sequence (backbone selected from SEQ ID NO: 16, 27, 29 and 31) are generated, cloned, expressed and purified as described generally in Example 1, producing polymerase enzymes having the amino acid sequences set forth as SEQ ID NOs: 17, 28, 30 and 32-40.

The purified mutant polymerases are screened for phasing/pre-phasing activity as generally described above in Example 1 and compared to the control polymerases having the sequence set forth in SEQ ID NO: 16, 27, 29 and 31. Those polymerases having the following mutations are shown to have improved phasing and/or pre-phasing activity compared to the control:

| Mutant | SEQ ID NOs: |
|---|---|
| T144A | 17, 28, 30, 32 |
| G153D | 17, 28, 30, 32 |
| K476W | 17, 28, 30, 32, 35 |
| L478S | 17, 28, 30, 32, 36 |
| T590I | 17, 28, 30, 32, 39 |
| A639V | 17, 28, 30, 32 |
| D718N | 17, 28, 30, 32 |
| T144A<br>G153D<br>K476W<br>L478S<br>T590I<br>A639V<br>D718N | 17, 28, 30, 32, 33, 34 |
| T144A<br>G153D<br>T590I<br>A639V<br>D718N | 17, 28, 30, 32 |
| K476W<br>L478S<br>T590I | 17, 28, 30, 32, 37 |
| K476W<br>T590I | 17, 28, 30, 32, 38 |
| K476W<br>L478S | 17, 28, 30, 32, 40 |

Example 6

Screen of Mutants of Pfu Exo⁻ Polymerase

Based upon analysis of sequence alignment to the 9° N polymerase backbone sequence (see FIG. 1), specific mutations to *Pyrococcus furiosus* (Pfu) Exo⁻ polymerase backbone sequence (SEQ ID NO: 18) are generated, cloned, expressed and purified as described generally in Example 1, producing polymerase enzymes having the amino acid sequences set forth as SEQ ID NOs: 19-20.

The purified mutant polymerases are screened for phasing/pre-phasing activity as generally described above in Example 1 and compared to the control polymerase having the sequence set forth in SEQ ID NO: 18. Those polymerases having the following mutations are shown to have improved phasing and/or pre-phasing activity compared to the control:

| Mutant | SEQ ID NO: |
|---|---|
| T144A | 19 |
| G153D | 19 |
| K477W | 19 |
| L479S | 19 |
| T591I | 19 |
| A640V | 19 |
| D719N | 19 |
| T144A | 19 |
| G153D | |
| K477W | |
| L479S | |
| T591I | |
| A640V | |
| D719N | |
| T144A | 19 |
| G153D | |
| T591I | |
| A640V | |
| D719N | |
| K477W | 19 |
| L479S | |
| T591I | |
| K477W | 19 |
| T591I | |
| T144A | 20 |
| L409A | |
| Y410A | |
| P411I | |
| G153D | 20 |
| L409A | |
| Y410A | |
| P411I | |
| K477W | 20 |
| L409A | |
| Y410A | |
| P411I | |
| L479S | 20 |
| L409A | |
| Y410A | |
| P411I | |
| T591I | 20 |
| L409A | |
| Y410A | |
| P411I | |
| A640V | 20 |
| L409A | |
| Y410A | |
| P411I | |
| D719N | 20 |
| L409A | |
| Y410A | |
| P411I | |
| T144A | 20 |
| G153D | |
| K477W | |
| L479S | |
| T591I | |
| A640V | |
| D719N | |
| L409A | |
| Y410A | |
| P411I | |
| T144A | 20 |
| G153D | |
| T591I | |
| A640V | |
| D719N | |
| L409A | |
| Y410A | |
| P411I | |
| K477W | 20 |
| L479S | |
| T591I | |
| L409A | |
| Y410A | |
| P411I | |
| K477W | 20 |
| T591I | |
| L409A | |
| Y410A | |
| P411I | |

Example 7

Screen of Mutants of KOD1 Exo⁻ Polymerase

Based upon analysis of sequence alignment to the 9° N polymerase backbone sequence (see FIG. 1), specific mutations to *Thermococcus kodakaraensis* (KOD1) Exo⁻ polymerase backbone sequence (SEQ ID NO: 21) are generated, cloned, expressed and purified as described generally in Example 1, producing polymerase enzymes having the amino acid sequences set forth as SEQ ID NOs: 22-23.

The purified mutant polymerases are screened for phasing/pre-phasing activity as generally described above in Example 1 and compared to the control polymerase having the sequence set forth in SEQ ID NO: 21. Those polymerases having the following mutations are shown to have improved phasing and/or pre-phasing activity compared to the control:

| Mutant | SEQ ID NO: |
|---|---|
| T144A | 22 |
| G153D | 22 |
| K476W | 22 |
| L478S | 22 |
| T590I | 22 |
| A639V | 22 |
| D718N | 22 |
| T144A | 22 |
| G153D | |
| K476W | |
| L478S | |
| T590I | |
| A639V | |
| D718N | |
| T144A | 22 |
| G153D | |
| T590I | |
| A639V | |
| D718N | |
| K476W | 22 |
| L478S | |
| T590I | |
| K476W | 22 |
| T590I | |
| T144A | 23 |
| L408A | |
| Y409A | |
| P410I | |
| G153D | 23 |
| L408A | |
| Y409A | |
| P410I | |
| K476W | 23 |
| L408A | |
| Y409A | |
| P410I | |
| L478S | 23 |
| L408A | |
| Y409A | |
| P410I | |

| Mutant | SEQ ID NO: |
|---|---|
| T590I | 23 |
| L408A | |
| Y409A | |
| P410I | |
| A639V | 23 |
| L408A | |
| Y409A | |
| P410I | |
| D718N | 23 |
| L408A | |
| Y409A | |
| P410I | |
| T144A | 23 |
| G153D | |
| K476W | |
| L478S | |
| T590I | |
| A639V | |
| D718N | |
| L408A | |
| Y409A | |
| P410I | |
| T144A | 23 |
| G153D | |
| T590I | |
| A639V | |
| D718N | |
| L408A | |
| Y409A | |
| P410I | |
| K476W | 23 |
| L478S | |
| T590I | |
| L408A | |
| Y409A | |
| P410I | |
| K476W | 23 |
| T590I | |
| L408A | |
| Y409A | |
| P410I | |

Example 8

Screen of Mutants of MMS2 Exo⁻ Polymerase

Based upon analysis of sequence alignment to the 9° N polymerase backbone sequence (see FIG. 1), specific mutations to *Methanococcus maripaludis* (MMS2) Exo⁻ polymerase backbone sequence (SEQ ID NO: 24) are identified based upon homology in an alignment with 9° N polymerase (see FIG. 2). The mutants are generated, cloned, expressed and purified as described generally in Example 1, producing polymerase enzymes having the amino acid sequences set forth as SEQ ID NOs: 25-26.

The purified mutant polymerases are screened for phasing/pre-phasing activity as generally described above in Example 1 and compared to the control polymerase having the sequence set forth in SEQ ID NO: 24. Those polymerases having the following mutations are shown to have improved phasing and/or pre-phasing activity compared to the control:

| Mutant | SEQ ID NO: |
|---|---|
| V156A | 25 |
| K165D | 25 |
| Y492W | 25 |
| I494S | 25 |

| Mutant | SEQ ID NO: |
|---|---|
| T609I | 25 |
| A658V | 25 |
| V156A | 25 |
| G153D | |
| Y492W | |
| I494S | |
| T609I | |
| A658V | |
| V156A | 25 |
| G153D | |
| T609I | |
| A658V | |
| Y492W | 25 |
| I494S | |
| T609I | |
| Y492W | 25 |
| T609I | |
| V156A | 26 |
| L417A | |
| Y418A | |
| P419I | |
| G153D | 26 |
| L417A | |
| Y418A | |
| P419I | |
| Y492W | 26 |
| L417A | |
| Y418A | |
| P419I | |
| I494S | 26 |
| L417A | |
| Y418A | |
| P419I | |
| T609I | 26 |
| L417A | |
| Y418A | |
| P419I | |
| A658V | 26 |
| L417A | |
| Y418A | |
| P419I | |
| V156A | 26 |
| G153D | |
| Y492W | |
| I494S | |
| T609I | |
| A658V | |
| L417A | |
| Y418A | |
| P419I | |
| V156A | 26 |
| G153D | |
| T609I | |
| A658V | |
| L417A | |
| Y418A | |
| P419I | |
| Y492W | 26 |
| I494S | |
| T609I | |
| L417A | |
| Y418A | |
| P419I | |
| Y492W | 26 |
| T609I | |
| L417A | |
| Y418A | |
| P419I | |

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:

1. A recombinant DNA polymerase comprising an amino acid sequence that is at least 80% identical to SEQ ID NO:10, which recombinant DNA polymerase comprises at least one amino acid substitution mutation at one or more positions functionally equivalent to Thr144, Gly153, Lys476, Leu478, Thr590, Ala639 or Asp718 in the 9° N DNA polymerase amino acid sequence, wherein the mutation at the position functionally equivalent to Gly153 comprises a mutation to a polar amino acid, wherein the mutation at the position functionally equivalent to Lys476 comprises a mutation to a hydrophobic amino acid, wherein the mutation at the position functionally equivalent to Leu478 comprises a mutation to a polar amino acid, wherein the mutation at the position functionally equivalent to Asp718 comprises a mutation homologous to Asp718Asn, and wherein the DNA polymerase is a family B DNA polymerase.

2. The altered polymerase of claim 1, wherein said substitution mutation at position Thr144 comprises a mutation to a nonpolar amino acid.

3. The altered polymerase of claim 1, wherein said substitution mutation at position Thr144 comprises a mutation homologous to Thr144Ala, Thr144Gly, or Thr144Leu.

4. The altered polymerase of claim 1, wherein said substitution mutation at position Gly153 comprises a mutation homologous to Gly153Asp.

5. The altered polymerase of claim 1, wherein said substitution mutation at position Lys476 comprises a mutation homologous to Lys476Trp.

6. The altered polymerase of claim 1, wherein said substitution mutation at position Leu478 comprises a mutation homologous to Leu478Ser, Leu478Arg, or Leu478Thr.

7. The altered polymerase of claim 1, wherein said substitution mutation at position Thr590 comprises a mutation to a non-polar amino acid.

8. The altered polymerase of claim 1, wherein said substitution mutation at position Thr590 comprises a mutation homologous to Thr590Ile, or Thr590Gly.

9. The altered polymerase of claim 1, wherein said substitution mutation at position Ala639 comprises a mutation homologous to Ala639Val, or Ala639Phe.

10. The altered polymerase of claim 1, wherein the altered polymerase further comprises substitution mutations at positions functionally equivalent to Leu408, Tyr409, Pro410, or a combination thereof, in the 9° N DNA polymerase amino acid sequence.

11. The altered polymerase of claim 1, wherein the altered polymerase comprises substitution mutations at positions functionally equivalent to Asp141, Glu143, or a combination thereof, in the 9° N DNA polymerase amino acid sequence.

12. The altered polymerase of claim 1, wherein the altered polymerase further comprises substitution mutations at positions functionally equivalent to Ala485 in the 9° N DNA polymerase amino acid sequence.

13. The recombinant DNA polymerase of claim 1, wherein said substitution mutation comprises a mutation homologous to Thr144Ala, Thr144Gly, Thr144Leu, Gly153Asp, Lys476Trp, Leu478Ser, Leu478Arg, Leu478Thr, Thr590Ile, Thr590Gly, Ala639Val, Ala639Phe or Asp718Asn, relative to SEQ ID NO: 10.

14. The altered polymerase of claim 1, wherein amino acid sequence is at least 90% identical to SEQ ID NO: 10.

15. The altered polymerase of claim 1, wherein amino acid sequence is at least 95% identical to SEQ ID NO: 10.

16. The altered polymerase of claim 1, wherein amino acid sequence is at least 99% identical to SEQ ID NO: 10.

* * * * *

UNITED STATES PATENT AND TRADEMARK OFFICE
CERTIFICATE OF CORRECTION

PATENT NO. : 9,677,057 B2
APPLICATION NO. : 14/869792
DATED : June 13, 2017
INVENTOR(S) : Bomati et al.

It is certified that error appears in the above-identified patent and that said Letters Patent is hereby corrected as shown below:

On the Title Page

Under Other Publications in Line 31, at Rodriquez et al., delete "Archeaon" and insert --Archaeon--.

In the Claims

Column 184, Claim 11, insert --further-- prior to comprises;

Column 184, Claim 14, insert --the-- prior to amino;

Column 184, Claim 15, insert --the-- prior to amino;

Column 184, Claim 16, insert --the-- prior to amino.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*